United States Patent
Zhan

(10) Patent No.: US 11,912,663 B2
(45) Date of Patent: *Feb. 27, 2024

(54) MULTI-TARGETED TYROSINE KINASE INHIBITORS AND THEIR PHARMACEUTICAL USES

(71) Applicant: Shanghai AB PharmaTech Ltd., Shanghai (CN)

(72) Inventor: Zheng-Yun James Zhan, Shanghai (CN)

(73) Assignee: Shanghai AB PharmaTech Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,930

(22) Filed: Aug. 12, 2022

(65) Prior Publication Data
US 2023/0124784 A1  Apr. 20, 2023

(30) Foreign Application Priority Data
Aug. 12, 2021  (CN) .......................... 202110924393.5

(51) Int. Cl.
| | |
|---|---|
| C07D 215/233 | (2006.01) |
| A61K 45/06 | (2006.01) |
| C07D 401/12 | (2006.01) |
| C07D 405/12 | (2006.01) |
| A61P 35/02 | (2006.01) |
| A61P 11/00 | (2006.01) |
| A61P 35/00 | (2006.01) |
| A61K 31/44 | (2006.01) |
| A61K 31/47 | (2006.01) |
| A61K 31/4709 | (2006.01) |
| A61K 31/496 | (2006.01) |
| A61K 31/506 | (2006.01) |
| A61K 31/513 | (2006.01) |
| C07D 215/48 | (2006.01) |
| C07D 401/06 | (2006.01) |

(52) U.S. Cl.
CPC .......... *C07D 215/233* (2013.01); *A61K 31/44* (2013.01); *A61K 31/47* (2013.01); *A61K 31/4709* (2013.01); *A61K 31/496* (2013.01); *A61K 31/506* (2013.01); *A61K 31/513* (2013.01); *A61K 45/06* (2013.01); *A61P 11/00* (2018.01); *A61P 35/00* (2018.01); *A61P 35/02* (2018.01); *C07D 215/48* (2013.01); *C07D 401/06* (2013.01); *C07D 401/12* (2013.01); *C07D 405/12* (2013.01); *C07B 2200/05* (2013.01)

(58) Field of Classification Search
None
See application file for complete search history.

(56) References Cited

U.S. PATENT DOCUMENTS

2019/0375714 A1    12/2019  Si et al.
2020/0262791 A1*   8/2020  Zhang ..................... A61P 35/00

FOREIGN PATENT DOCUMENTS

CN          113480479 A      10/2021

OTHER PUBLICATIONS

International Search Report dated Oct. 24, 2022 in International Application No. PCT/CN2022/112014.
International Search Report dated Oct. 24, 2022 in International Application No. PCT/CN2022/112011.
Sadineni et al., "Novel method for the synthesis of lenvatinib using 4-nitrophenyl cyclopropylcarbamate and their pharmaceutical salts", Chemical Papers, 2021, vol. 75, pp. 1475-1483 (9 pages total).

* cited by examiner

*Primary Examiner* — Zinna Northington Davis
(74) *Attorney, Agent, or Firm* — Sughrue Mion, PLLC

(57) ABSTRACT

Disclosed are compounds of Formula IIIb, their stereoisomers, tautomers, deuterates, pharmacologically acceptable salts, or hydrates thereof, methods of their preparation and pharmaceutical compositions and uses comprising such compounds. The Formula IIIb compounds are useful and highly effective as multi-targeted tyrosine kinase inhibitors in treating several kinds of cancers such as pancreatic cancer, lung cancer, renal cancer, liver cancer, gastric cancer, cervical cancer, leukemia, prostatic cancer, and other antitumor uses.

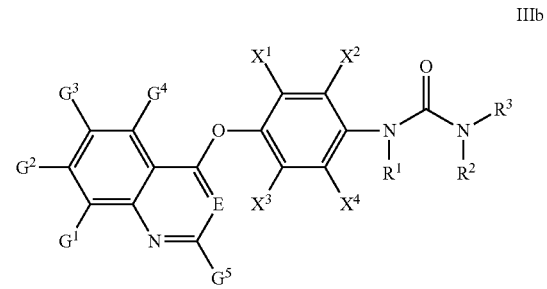

8 Claims, No Drawings

MULTI-TARGETED TYROSINE KINASE INHIBITORS AND THEIR PHARMACEUTICAL USES

CROSS-REFERENCE TO RELATED APPLICATIONS

The present application claims priority to Chinese patent application No. CN202110924393.5, filed on Aug. 12, 2021, the contents of which are incorporated herein by reference.

FIELD OF THE INVENTION

The present invention relates to a novel class of antitumor compounds, and their uses as multi-targeted tyrosine kinase inhibitors (TKI) in treating different kinds of cancers such as liver cancer, bladder cancer, thyroid cancer, cervical cancer, and leukemia.

BACKGROUND OF THE INVENTION

Protein tyrosine kinases (PTKs) are the largest known protein superfamily, and they are important hubs for extracellular signaling into the cell. The protein tyrosine kinases play an important role in the regulation of cell proliferation and differentiation. Abnormal expression of PTKs activates a series of downstream signaling pathways, causing a cascade response, resulting in disruption of cell proliferation regulation and ultimately leading to tumor formation. Tyrosine kinases can be divided into receptor-type tyrosine kinases (RTK) and non-receptor-type tyrosine kinases (nRTK). RTKs include Vascular Endothelial Growth Factor Receptor (VEGFR), Fibroblast Growth Factor Receptor (FGFR), Epidermal Growth Factor Receptor [abb. as EGFR, HER1, or ErbB-1, is a member of the epidermal growth factor receptor (HER) family], tyrosine kinase membrane receptor (c-Met), platelet-derived growth factor receptor α (PDGFRα), and RET (RE arranged during Transfection, a transmembrane receptor tyrosine kinase) etc., these RTKs are closely associated with oncological diseases and their targeted therapies.

So far, more than 80% of kinases have been used as targets for therapeutic drug development. It has been reported that pathological increases in vascular endothelial formation are associated with the pathogenesis or progression of various diseases, and that the proliferation of solid tumors is dependent on angiogenesis. Therefore, drugs that effectively inhibit the tyrosine kinases VEGFR1-3, FGFR1-4, EGFR, C-MET, RET, PDGFRα and other tyrosine kinase (RTK) targets mentioned above have become the main targeted therapies for refractory solid tumors. For example, FGFR4 is highly expressed in cancers such as liver cancer, bladder cancer, renal cancer, thyroid, gastric cancer, colon cancer and esophageal cancers.

Currently, most of the molecularly targeted antitumor drugs marketed are protein tyrosine kinase inhibitors (PTKI) targeting PTK, for example, the small molecule urea structure based compounds that have better inhibitory effect on tyrosine kinase VEGFR1-3 and are clinically used for the treatment of hepatocellular carcinoma include Sorafenib, Regorafenib, and Lenvatinib (which has better inhibitory effect on both tyrosine kinase VEGFR1-3 and FGFR1-4) (Ref-1), which has a better antitumor effect in clinical treatment.

The purpose of the present invention is to develop a novel multi-targeted tyrosine kinase inhibitor (TKI) with higher tyrosine kinase inhibiting activity and lower toxicity and side effects through the innovative design of small molecule structures and their functional groups, which can be more effective used for the treatment of various tumors such as liver cancer, bladder cancer, renal cancer, thyroid cancer, gastric cancer, colon cancer, esophageal cancer, lung cancer, uterine cancer, skin cancer and other related cancer diseases.

The present invention relates to a class of formula IIIb multi-substituted anilino-urea compounds as multi-target tyrosine kinase inhibitors (TKI), with novel multi-substituted aniline building block as the focus of innovation. These compounds efficiently inhibit not only vascular endothelial growth factor receptors (VEGFR1, VEGFR2, VEGFR3) and fibroblast growth factor receptors (FGFR1-4), but also multiple important receptor tyrosine kinases (RTK) that may contribute to angiogenesis and tumor growth pathogenesis in addition to their normal cellular functions. For example, including but not limited to C-MET, RET, PDGFRα and other tyrosine kinases, which can produce relatively strong inhibition of angiogenesis and have better applications in more effective prevention and treatment of various tumors with abnormal proliferation of angiogenesis and other diseases.

The structure of the urea structure based compounds containing multi-substituted aniline groups disclosed in the present invention is based on the structural characteristics of tyrosine kinase targets, and structural modification innovation and optimization by introducing more substituents in aniline, thus developing a multi-target tyrosine kinase inhibitor (TKI) with better inhibition effect, which can treat many types of tumors more effectively.

SUMMARY OF THE INVENTION

The present invention relates to a class of novel antitumor compounds of the following formulas IIIb with the urea based structure formed with both multi-substituted arylamines and alkyl-amines groups, which has been evaluated to be highly potent and effective for inhibiting more than ten kinds of tyrosine kinases such as VEGFR1-3, FGFR1-4, C-MET, RET, PDGFRα, etc. The experimental results show better inhibitory effect, better application prospect, and better safety. This invention further relates to pharmaceutical compositions comprising one or more of newly developed compounds (in a pure form or mixture of stereo-isomers, solvates, hydrates, tautomers, prodrugs, or pharmaceutically acceptable salts thereof) and another agent(s) developed as therapeutic drugs for cancer treatment.

In the first aspect, the present invention provides a compound represented by the formula IIIB, or a stereoisomer, tautomer, deuterates, or pharmacologically acceptable salts, or hydrate thereof:

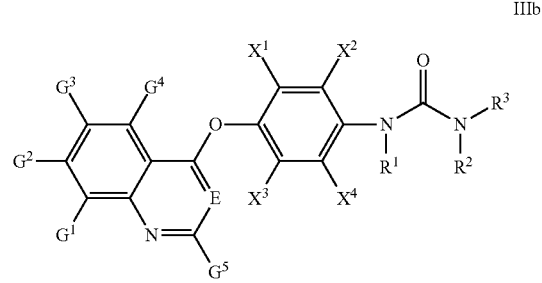

IIIb wherein:

E is a nitrogen (N) or CH;

$G^1$ is independently selected from H, deuterium (D), halogen, cyano, $C_{1-6}$ alkyl, $C_{1-6}$ alkoxy, or $C_{1-6}$ alkylamino group;

$G^2$ is independently selected from halogen, cyano, $C_{1-6}$ alkylamino, $C_{2-6}$ hydroxyalkylideneamino, $C_{3-6}$ hydroxycloalalkylideneamino, $C_{1-6}$ cyanoalkylideneamino, $C_{4-6}$ cyanocycloalalkylideneamino, $C_{1-6}$ aminoalkylideneamino, $C_{3-6}$ aminocycloalkylideneamino, $C_{1-6}$ carboxyalkylideneamino, $C_{3-6}$ carboxycycloalalkylideneamino, 3-6 members heterocyclic-amino group, or —$OR^6$, wherein $R^6$ is independently selected from H, deuterium (D), $C_{1-6}$ alkyl, $C_{1-6}$ haloalkyl, $C_{1-6}$ cyanoalkyl, $C_{3-6}$ cyanocycloalalkylidene, $C_{2-6}$ hydroxyalkylidene, $C_{3-6}$ hydroxycycloalkylidene, $C_{1-6}$ aminoalkylidene, $C_{3-6}$ aminocycloalkylidene, $C_{3-6}$ aminocycloalkylidene, $C_{2-6}$ carboxyalkylidene, $C_{3-6}$ carboxycycloalalkylidene, $C_{3-6}$ cycloalkylidene, $C_{3-6}$ aminocycloalkylidene, $C_{1-6}$ amino($C_{3-6}$cycloalkyl)alkylidene, 3~6 members heterocycloalkyl, or 3~6 members heterocycloalkylidene group.

$G^3$ is independently selected from cyano, —C(O)OR, —C(O)NH$_2$, —C(O)ND$_2$, $C_{1-6}$ alkoxy, $C_{1-6}$ alkylamino, or a —C(O)NR$^4$R$^5$ group: wherein R is H, or $C_{1-6}$ alkyl, $R^4$ and $R^5$ are each independently selected from H, deuterium (D), $C_{1-6}$ alkyl, $C_{1-6}$ haloalkyl, $C_{1-6}$ cyanoalkylidene, $C_{3-6}$ cyanocycloalalkylidene $C_{2-6}$ hydroxyalkylidene, $C_{3-6}$ hydroxycycloalkylidene, $C_{2-6}$ aminoalkylidene, $C_{3-6}$ aminocycloalkylidene, $C_{2-6}$ carboxyalkylidene, $C_{3-6}$ carboxycycloalalkylidene, $C_{3-6}$ cycloalkenyl, $C_{3-6}$ cycloalkyl, 3~6 members heterocyclic, 3~6 members heterocyclic alkylidene, $C_{6-10}$ aryl, $C_{3-6}$ heterocyclic aryl, $C_{1-6}$ alkyl sulfonyl, $C_{3-6}$ cycloalkyl sulfonyl, or $C_{2-6}$ heterocycloalkyl sulfonyl group; or $R^4$ and $R^5$ may be linked each other to form a $C_{2-6}$ heterocyclic group or a $C_{3-6}$ heterocyclic aryl group containing 3-8 members of 1-3 heteroatoms; or may be linked each other to form $C_9$-$C_{20}$ fused alkylaryl or $C_5$-$C_{20}$ aryl group, $G^4$ and $G^5$ are each independently selected from H, deuterium (D), halogen, cyano, $C_{1-6}$ alkyl, $C_{1-6}$ alkoxy, or $C_{1-6}$ alkylamino goup;

$R^1$ is each independently selected from H, deuterium (D), $C_{1-6}$ alkyl, $C_{3-6}$ cycloalkyl, or $C_{3-6}$ deuterated cycloalkyl group;

$R^2$ and $R^3$ are each independently selected from H, deuterium (D), $C_{1-6}$ alkyl, $C_{3-6}$ cycloalkyl, $C_{3-6}$ deuterated cycloalkyl, or a 3-6 membered heterocyclic group;

$X^1$, $X^2$ and $X^3$ are each independently selected from halogen, cyano, amino, $C_{1-6}$ alkoxy, or $C_{1-6}$ alkyl amino group;

$X^4$ is each independently selected from H, deuterium (D), halogen, cyano, amino, $C_{1-6}$ alkoxy, or $C_{1-6}$ alkylamino group.

In another preferred embodiment of the invention, wherein

E is CH;

$G^1$, $G^4$ and $G^5$ are each independently selected from H;

$G^2$ is —$OR^6$, wherein $R^6$ is independently selected from the group consisting of H, deuterium (D), $C_{1-6}$ alkyl, $C_{1-6}$ haloalkyl, $C_{1-6}$ cyanoalkylidene, $C_{2-6}$ hydroxyalkylidene, $C_{2-6}$ aminoalkylidene, $C_{2-6}$ carboxyalkylidene, $C_{3-6}$ cycloalkyl, $C_{3-6}$ aminocycloalkylidene, $C_{1-6}$ amino($C_{3-6}$cycloalkyl) alkylidene, 3~6 members heterocycloalkyl, or 3~6 members heterocycloalkylidene group;

$G^3$ is independently selected from the group consisting of C(O)OR, C(O)NH$_2$, or a C(O)NR$^4$R$^5$ group: where in, R is H, or $C_{1-6}$ alkyl, $R^4$ and $R^5$ are each independently selected from the group consisting of H, $C_{1-6}$ alkyl, $C_{1-6}$ haloalkyl, $C_{1-6}$ cyanoalkylidene, $C_{2-6}$ hydroxyalkylidene, $C_{2-6}$ aminoalkylidene, $C_{3-6}$ cycloalkyl, 3~6 members heterocyclic, 3~6 members heterocyclic alkylidene, $C_{3-6}$ heterocyclic aryl, $C_{1-6}$ alkyl sulfonyl, $C_{3-6}$ cycloalkyl sulfonyl, or $C_{2-6}$ heterocycloalkyl sulfonyl group; or $R^4$ and $R^5$ are interconnected into a heterocyclic group or a heterocyclic aryl, of 3-8 members containing 1-3 heteroatoms;

$R^1$ is H;

$R^2$ is H;

$R^3$ is independently selected from $C_{3-6}$ cycloalkyl group;

$X^1$, $X^2$ and $X^3$ are each independently selected from halogen;

$X^4$ is H.

In the second aspect, the present invention provides a method of preparing the formula IIIb compounds.

In the third aspect, the present invention provides a method of preparing two intermediate compounds RM1 and RM1b-01.

In the fourth aspect, the present invention provides a method of preparing the new multi-substituted functional compound SM2-01.

In the fifth aspect, the present invention provides a pharmaceutical composition and uses comprising one or more compounds selected from the structure IIIb.

The sixth aspect of the present invention provides a pharmaceutical composition comprising at least one compound according to claim 1 and at least one compound selected from the group consisting of a tyrosine kinase (RTK) inhibitor.

The seventh aspect of the present invention provides a method of treating several kinds of cancers effectively with the formula IIIb compounds, wherein the treated cancers are selected from pancreatic cancer, lung cancer, renal cancer, liver cancer, gastric cancer, cervical cancer, leukemia.

The eighth aspect of the present invention provides a method for treating several kinds of cancers effectively by using one or more compounds of the structure IIIb and in combination with any or combined one or more of (1) an immunomodulator, (2) PD-1 inhibitor; (3) PD-L1 inhibitor; or (4) another active ingredient that does not fall under (1)-(3) above.

Overall, all prepared new formula IIIb compounds have been evaluated for their potency and toxicity. The present invention explores the relationship between the structures of new multi-substituted functional aryl amino group incorporated in the formula IIIb compounds and potency of RTK inhibition, and finally to provide valuable clue and potential effective and safe antitumor RTK inhibitors.

The present invention not only relates to design and synthesize the novel antitumor formula IIIb compounds, but also explores the relation between different novel multi-substituted functional compounds (SM1-01~SM1-16 in Table 1, and other chemical reagents listed in Table 4) and their activity of RTK inhibition, and finally to optimize the inhibitor structure and develop some effective urea-based multi-targeted tyrosine kinase inhibitors.

DETAILED DESCRIPTION OF THE INVENTION

Details of the present invention are set forth in the following description for preparation and biological activity study of new RTK inhibitors IIIb. The advantages of the present invention will be significantly observed from the following detailed description.

As used herein, the term "alkyl" refers to any linear or branched chain alkyl group having a number of carbon atoms and/or "alkylene" in the specified range, wherein one or more hydrogens could be replaced by one or more halogens.

The term "alkoxy" refers to an "alkyl-O—" group.

The term "cycloalkyl" refers to any cyclic ring of an alkane or alkene having a number of carbon atoms and/or "alkylene" in the specified range, wherein one or more hydrogens could be replaced by one or more halogens.

The term "cycloalkyl-oxy" refers to a "cycloalkyl-O—".

The term "cycloalkyl-amino" refers to a "cycloalkyl-N (Ra)—", wherein Ra is alkyl or alkylcarbonyl group.

The term "halogen" (or "halo") refers to fluorine, chlorine, bromine and iodine atoms (or referred as fluoro, chloro, bromo, and iodo).

The term "carbonyl" refers to a "—C(O)—" group.

The term "alkylcarbonyl" refers to an "alkyl-C(O)—" group.

The term "alkoxy carbonyl" refers to an "alkyl-O—C(O)—" group.

The term "alkylamino carbonyl" refers to an "alkyl-NH—C(O)—" or "dialkyl-N—C(O)—" group.

The term "sulfonamido" refers to a "—S(O)2NH—" or "—S(O)2N(Ra)—" group, wherein Ra is alkyl or alkylcarbonyl group.

The term "alkyl sulfonamido" refers to an "alkyl-S(O)2NH—" or "alkyl-S(O)2N(Ra)—" group, wherein Ra is alkyl or alkylcarbonyl group.

The term "alkoxy sulfonamido" refers to an "alkyl-O—S(O)2NH—" or "alkyl-O—S(O)2N(Ra)—" group, wherein Ra is alkyl or alkylcarbonyl group.

The term "heteroaryl" refers to an aryl group with 1-3 hetero atoms including 0, N, and/or S atoms.

The term "fused heteroaryl" refers to a bi-cyclic, tri-cyclic or tetra-cyclic heteroaryl group with 1-5 hetero atoms such as O, N, and/or S atoms.

The term "poly-heteroaryl" refers to a bi-, tri- or tetra-heteroaryl functional group with 1-5 hetero atoms (e.g., O, N, S, and P) in one or more fused rings.

The term "poly-heterocyclic" refers to a bi-cyclic, tri-cyclic or tetra-cyclic functional group with 1-5 hetero atoms (e.g., O, N, S, and P) in one or more fused rings.

The term "composition" is intended to encompass a product comprising the specified ingredients, as well as any product which results, directly or indirectly, from combining the specified ingredients.

The term "pharmaceutically acceptable" means that the ingredients of the pharmaceutical composition must be compatible with each other and not deleterious to the recipient thereof. The term "effective amount" means that amount of active compound or pharmaceutical agent that elicits the biological or medicinal response in a tissue, system, animal or human that is being sought by a researcher, veterinarian, medical doctor or other clinician. The term also includes herein the amount of active compound sufficient to inhibit RTK for treating several kinds of cancers and thereby elicit the response being sought (i.e., an "inhibition effective amount"). When the active compound (i.e., active ingredient) is administered as the salt, references to the amount of active ingredient are to the free acid or free base form of the compound.

The present invention provides a class of novel antitumor RTK inhibitor compounds IIIb, and pharmaceutically acceptable salts, and/or hydrates as RTK inhibitors with high potency. Moreover, toxicity study for MTD is determined to be 300 mg/kg for IIIb-01.

The present invention also provides pharmaceutically acceptable salt forms of compounds of Formula IIIb. The scope of the present invention covers acid addition salts, which are formed by bringing a pharmaceutically suitable acid into contact with a compound of the present invention.

"Pharmaceutically acceptable acid complex salts" means those salts that retain biological validity and free base properties, are not undesirable biologically or otherwise, and are formed using inorganic acids, such as, but not limited to, hydrochloric acid, hydrobromic acid, sulfuric acid, phosphoric acid, nitric acid, carbonic acid, etc.; and organic acids, such as, but not limited to: Acetic acid, benzoic acid, methanesulfonic acid, toluenesulfonic acid, or valeric acid, etc.

Synthesis of New Antitumor Compounds with General Structure IIIb:

Some of reagents and raw materials used in the present invention are commercially available, but some of reagents and raw materials were not commercially available, e.g., new SM2-01 compound was finally designed and prepared by ourselves at AB PharmaTech Lab.

Abbreviations of chemical materials, reagents, and solvents related to the synthesis of antiviral compounds in the present invention are listed in the parts of examples.

The compounds in the present invention could be synthesized by normal raw materials through several synthetic methods after designing the structure of different compounds in the present invention.

The present disclosure relates to the following key innovations:

1) The present invention optimizes the RTK inhibition activity of the formula IIIb compounds, and many of formula IIIb compounds (such as IIIb-08, IIIb-09, IIIb-45, IIIb-50, IIIb-55, IIIb-56, IIIb-57, IIIb-58, IIIb-60, IIIb-61, IIIb-65) are highly potent to inhibit several important RTK targets (e.g., VEGFR1, VEGFR2, VEGFR3, FGFR2, and RET, etc.).

2) The formula IIIb compounds "IIIb-08, IIIb-09, IIIb-45, IIIb-50, IIIb-55, IIIb-56, IIIb-57, IIIb-58, IIIb-60, IIIb-61, IIIb-65" of the present invention have much better inhibitory effects on a variety of tumor cell lines [e.g., pancreatic cancer (BXPC3), lung cancer (A549), renal cancer (Caki-1), liver cancer (Hep3B 2.1-7), gastric cancer (SNU16), cervical cancer (Hela) and leukemia (K562), etc.] and can be used as targeted drugs effectively to treat several kinds of tumors or related cancers arising from RTK kinase mediated and have much better RTK targeting selectivity and safety.

3) The formula IIIb compounds "IIIb-08, IIIb-09, IIIb-45, IIIb-50, IIIb-55, IIIb-56, IIIb-57, IIIb-58, IIIb-60, IIIb-61, IIIb-65" of the present invention have much better safety profile, for example: compounds IIIb-01 has not only an MTD toxicity dose of >150 mg/kg in rats, but also has the parameter of potassium channel safety hERG>30 uM (for Lenvatinib antitumor drug, its MTD is 40 mg/kg in rats, and its hERG=11.9 uM).

The present invention also provides the following two synthetic methods of the formula IIIb compounds, and two synthetic methods have been optimized for scale-up production.

Synthetic Method 1
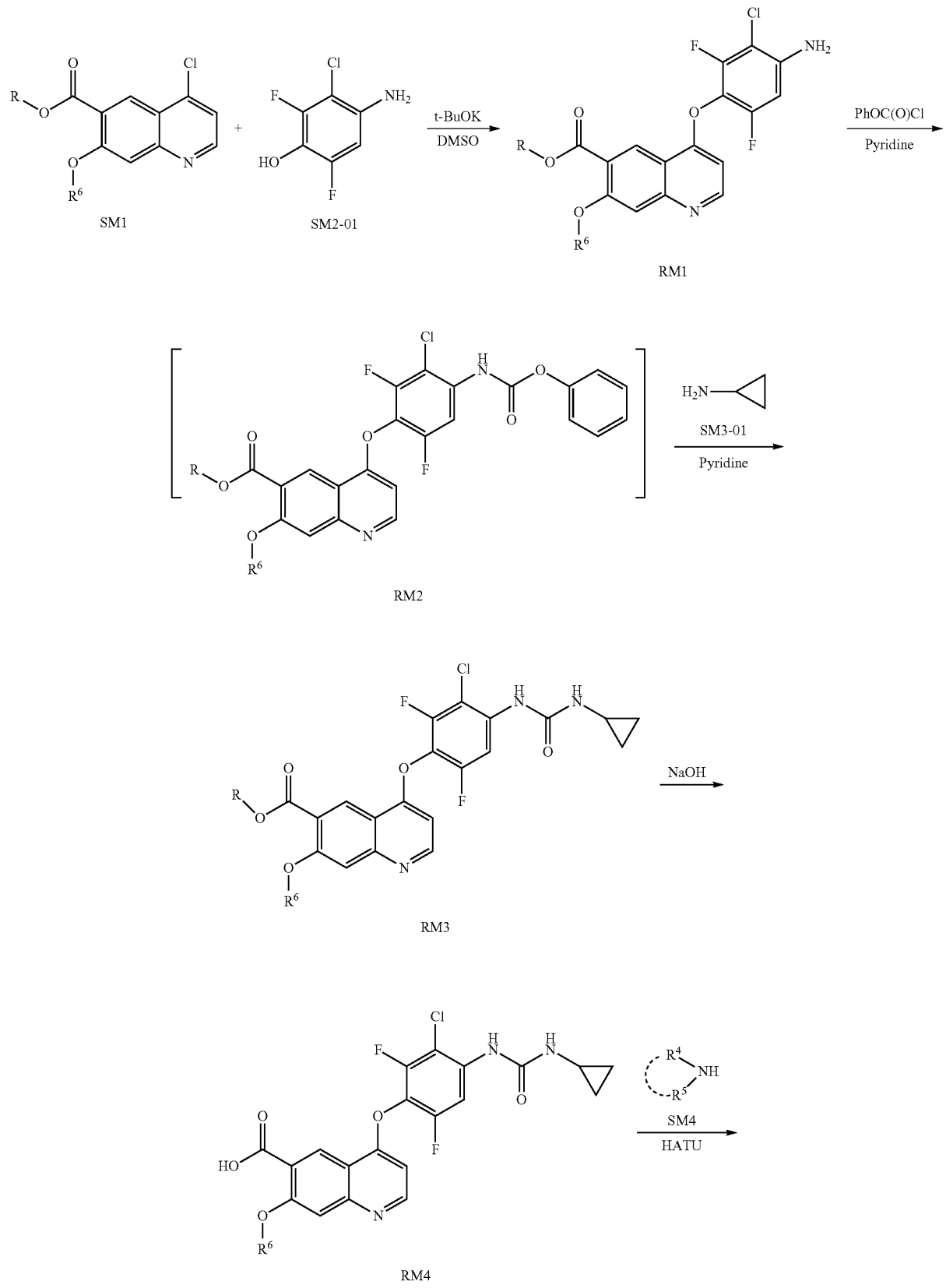

-continued

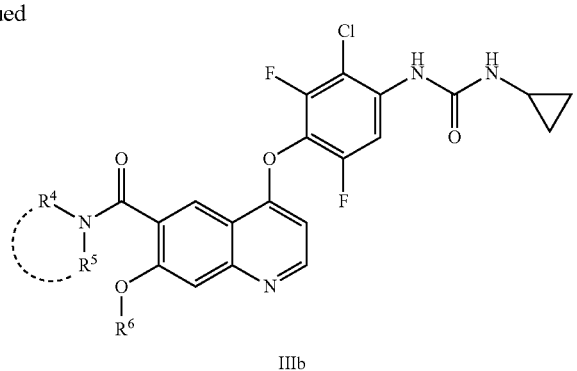

IIIb

In the above synthetic method 1, R, $R^4$, $R^5$ and $R^6$ each have the same definition as R, $R^4$, $R^5$ and $R^6$ in claim 1, respectively.

The synthetic method 1 for each reaction step is as follows:

1.1 Synthesis of Intermediate RM1

In a round bottom flask, a mixture of SM1 (1.0 eq), SM2 (1.0~1.5 eq), potassium tert-butoxide, (t-BuOK, 1.0~1.5 eq) and DMSO (6~10×) was heat to 50~100° C. under nitrogen. HPLC tracking detection until reach the end point, the reaction solution was post treated, purified by column chromatography and dried to obtain the intermediate RM1.

1.2 Synthesis of Intermediate RM2

The intermediate RM1 (1.0 eq) and pyridine (2.0~5.0 eq) were charged to DMF (5~8×) in a round bottom flask, and phenyl chloroformate (1.0~4.0 eq) was added dropwise below 10° C. The reaction was carried out at room temperature after the dropwise addition was completed. HPLC tracking detection until reach the end point, the reaction solution was post treated, purified by column chromatography and dried to obtain the intermediate RM2.

1.3 Synthesis of Intermediate RM3

In a round bottom flask, a mixture of RM2 (1.0 eq), SM3 (1.0~5.0 eg), pyridine (1.0~1.5 eq) and DMF (5~10×) was heat to 20~80° C. HPLC tracking detection until reach the end point, the reaction solution was post treated, purified by column chromatography and dried to obtain the intermediate RM3.

1.4 Synthesis of Intermediate RM4

A mixture of RM3-01 (1.0 eq), THF (2~10×), MeOH (2~10×) and sodium hydroxide (2.0~10.0 eq) was stirred at 20~80° C. in a round bottom flask. HPLC tracking detection until reach the end point, pH was adjusted to about 6 by 3N—HCl. The appeared precipitate was filtered, washed and dried to obtain intermediate RM4.

1.5 Synthesis of Formula IIIb Product

To a mixture of RM4 (1.0 eq), DMF (2~10×), HATU (1.0~2.0 eq) and SM4-01 (1.0~2.0 eq), DIEA (1.0~2.0 eq) was added dropwise at 20~40° C. HPLC tracking detection until reach the end point, the reaction solution was post treated, purified by column chromatography and dried to obtain IIIb.

Synthetic Method 2

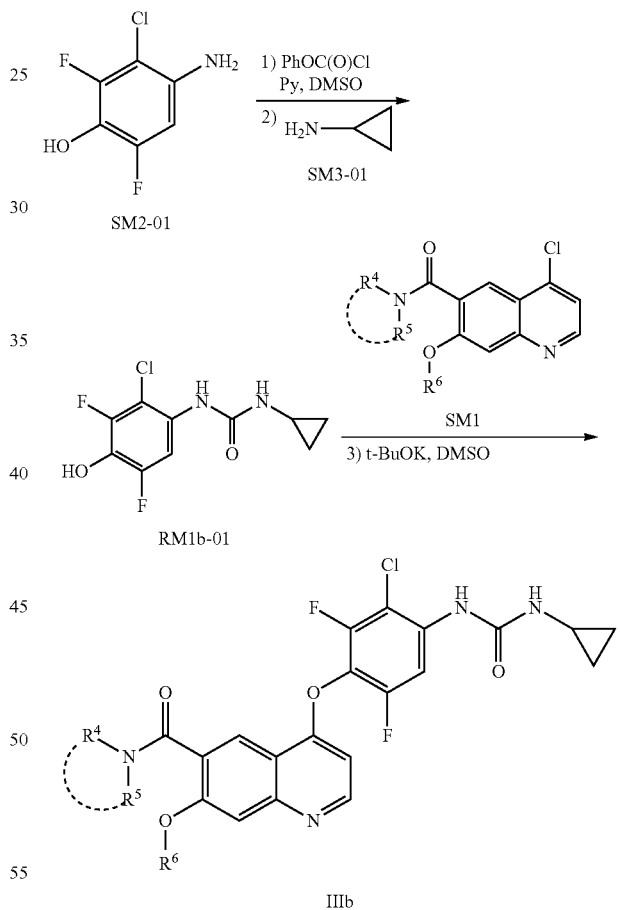

IIIb

In the above synthetic method 1, $R^4$, $R^5$ and $R^6$ each have the same definition as $R^4$, $R^5$ and $R^6$ in claim 1, respectively.

2.1 Synthesis of Intermediate RM1b-01

2.1-1 A mixture of SM2-01 (1.0 eq), Py (1.3 eq) and DMF (10×) was stirred in the ice bath. Phenyl chloroformate (1.1 eq) was added dropwise below 10° C. After the reaction was completed (IPC by HPLC), the reaction was worked up to get the RM2b or to the next step directly.

2.1-2 Cyclopropylamine (4.0 eq) was added dropwise below 10° C. Then the mixture was stirred at room temperature untill the reaction was completed (IPC by HPLC). Acetonitrile (15~20×) was added to the mixture, and the appeared precipitate was filtered. 6N—HCl was added dropwise to a mixture of the precipitate (1×) and MeOH (4×). The mixture was stirred until fully soluble, and then water (12×) was added. Then the appeared precipitate was filtered, washed with water (4×) and dried to obtain intermediate RM1b-01.

2.2 Synthesis of the Target Product of 11b

A mixture of SM1 (1.0 eq), SM1b-01 (1.0 eq~1.5 eq), DMSO (60 mL) and potassium t-butoxide (t-BuOK, 1.0~1.5 eq) was stirred at 40~100° C. After the reaction was completed (IPC by HPLC), the cooled mixture was dropped into ice water (100×). The appeared precipitate was filtered, washed by water and dried to obtain the target formula IIIb product.

Based on the preparation process described above, different kinds of the formula IIIb products were prepared with different kinds of starting materials SM1, SM2 and SM3 as listed in Tables 1, 2, 4, and different kinds of intermediates RM1, RM2, RM3, RM4, and IIIb compounds were prepared and listed in Table 5, and final formula IIIb products are listed in Table 5, respectively, as follows:

TABLE 1

Starting Materials SM1

| Structure | ID |
|---|---|
| (methyl 4-chloro-7-methoxyquinoline-6-carboxylate) | SM1-01 |
| (4-chloro-7-(fluoromethoxy)quinoline-6-carboxamide) | SM1-02 |
| (4-chloro-7-(difluoromethoxy)quinoline-6-carboxamide) | SM1-03 |
| (4-chloro-7-(2,2,2-trifluoroethoxy)quinoline-6-carboxamide) | SM1-04 |
| (4-chloro-7-(cyanomethoxy)quinoline-6-carboxamide) | SM1-05 |
| (4-chloro-7-(2-(dimethylamino)ethoxy)quinoline-6-carboxamide) | SM1-06 |
| (4-chloro-7-(2-hydroxyethoxy)quinoline-6-carboxamide) | SM1-07 |
| (4-chloro-7-((1-(Boc-amino)cyclopropyl)methoxy)quinoline-6-carboxamide) | SM1-08 |
| (4-chloro-7-((tetrahydrofuran-3-yl)oxy)quinoline-6-carboxamide, (S)) | SM1-09 |
| (4-chloro-7-((tetrahydrofuran-3-yl)oxy)quinoline-6-carboxamide, (R)) | SM1-10 |

TABLE 1-continued

Starting Materials SM1

| | |
|---|---|
| SM1-11 | 4-chloro-7-(cyclopentyloxy)quinoline-6-carboxamide |
| SM1-12 | 4-chloro-7-methoxyquinoline-6-carbonitrile |
| SM1-13 | 4-chloro-N-(2,2-difluoroethyl)-7-methoxyquinoline-6-carboxamide |
| SM1-14 | 4-chloro-N-(2-cyanoethyl)-7-methoxyquinoline-6-carboxamide |
| SM1-15 | 4-chloro-N-(cyanomethyl)-7-methoxyquinoline-6-carboxamide |
| SM1-16 | 4-chloro-7-(2-cyanoethoxy)quinoline-6-carboxamide |

TABLE 2

Starting Materials SM2

| | |
|---|---|
| SM2-01 | 3-amino-2-chloro-6-fluoro-phenol derivative |
| SM2-02 | 4-amino-2,6-difluoro-3-hydroxy aniline derivative |

TABLE 3a

"RM1" Structure in the First Step of Synthetic Method I

| | |
|---|---|
| RM1-01 | 4-(4-amino-3-chloro-2-fluoro-6-fluoro-phenoxy)-7-methoxyquinoline-6-carboxamide |
| RM1-02 | 4-(4-amino-2,3,6-trifluorophenoxy)-7-methoxyquinoline-6-carboxamide |
| RM1-03 | 4-(4-amino-3-bromo-2,6-difluoro-phenoxy)-7-methoxyquinoline-6-carboxamide |

TABLE 3a-continued
"RM1" Structure in the First Step of Synthetic Method I
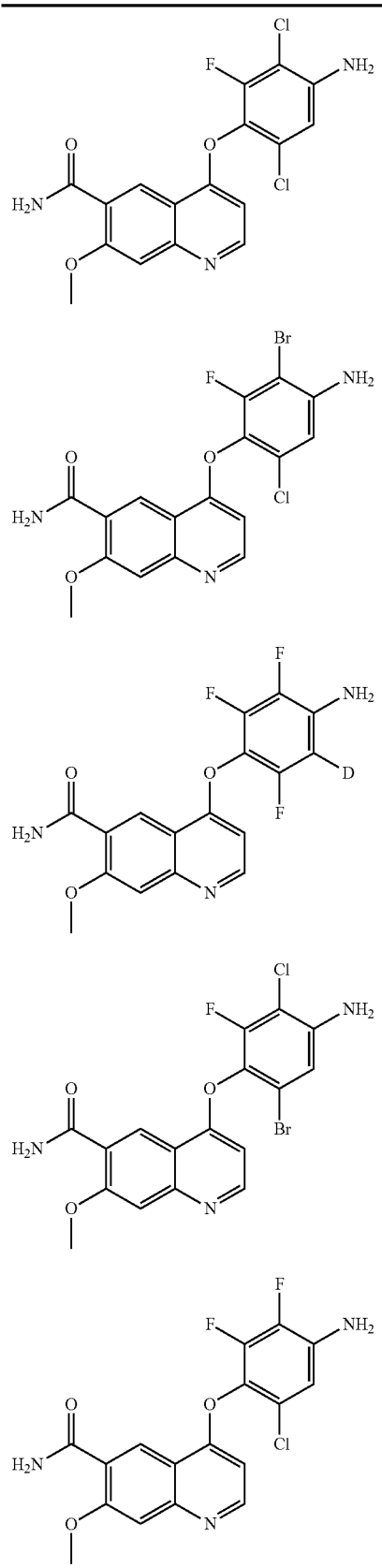
RM1-04
RM1-05
RM1-06
RM1-07
RM1-08
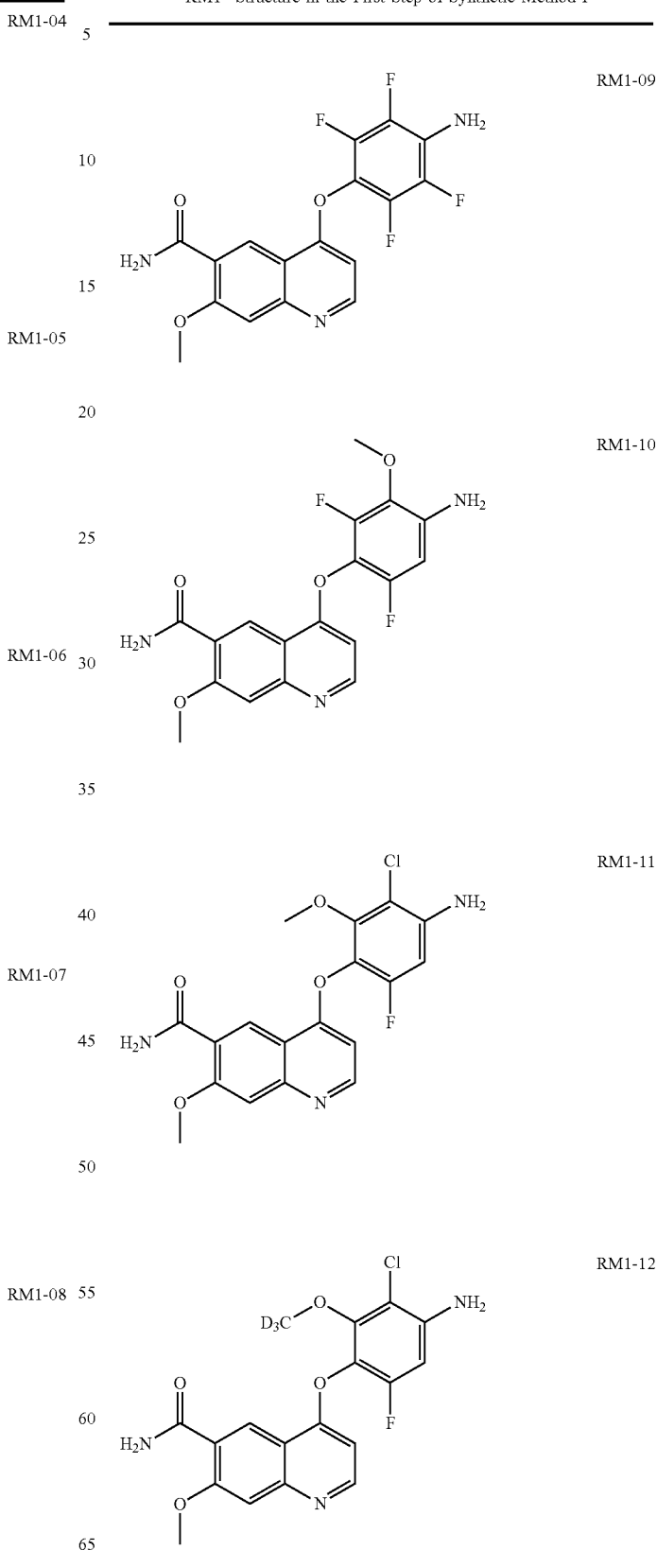
RM1-09
RM1-10
RM1-11
RM1-12

TABLE 3a-continued
"RM1" Structure in the First Step of Synthetic Method I
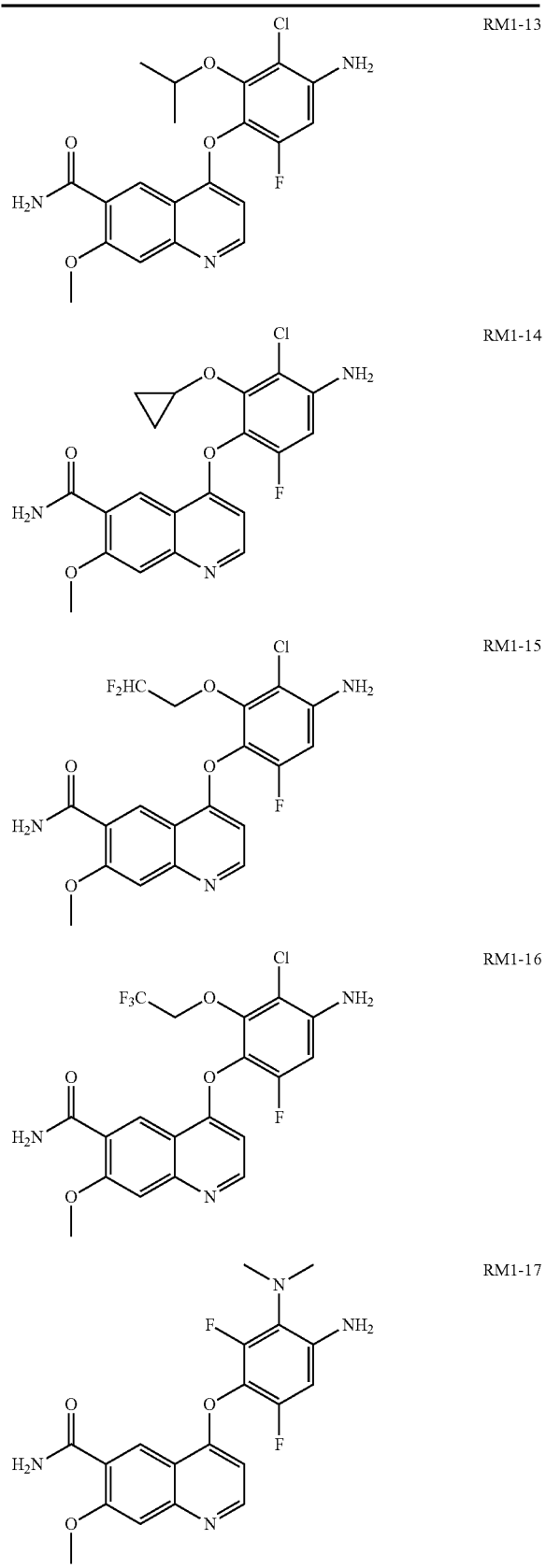
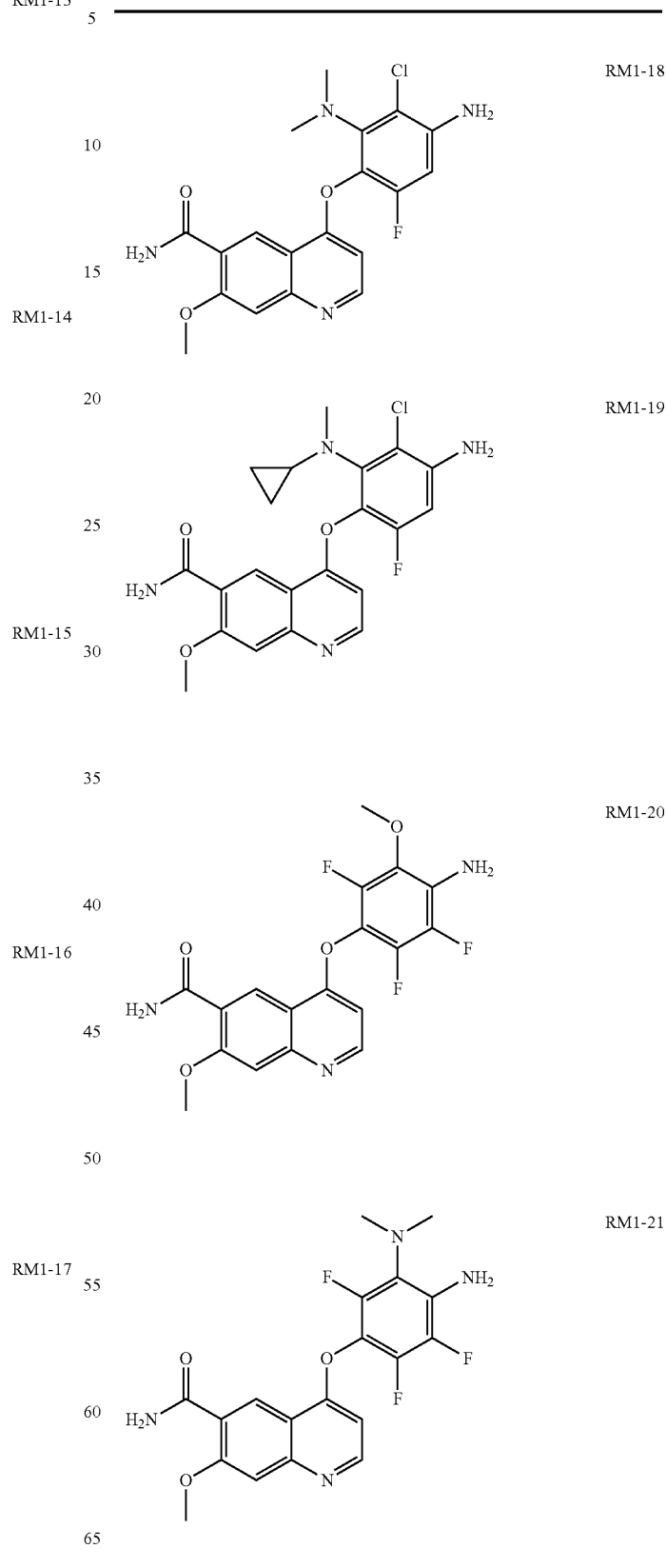

TABLE 3a-continued
"RM1" Structure in the First Step of Synthetic Method I
RM1-22
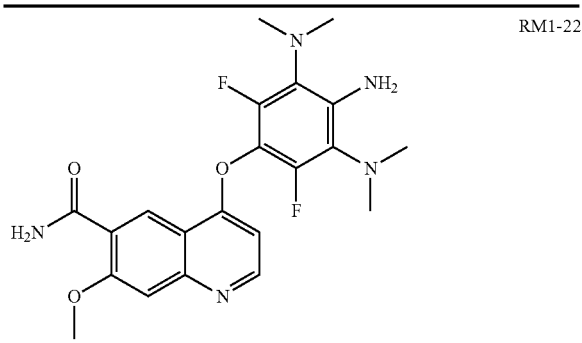
RM1-23
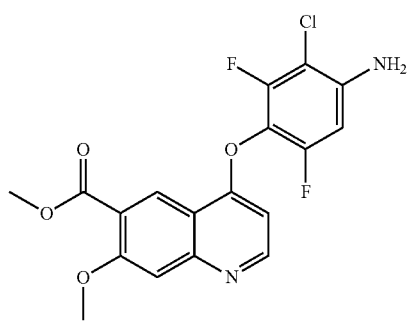
RM1-24
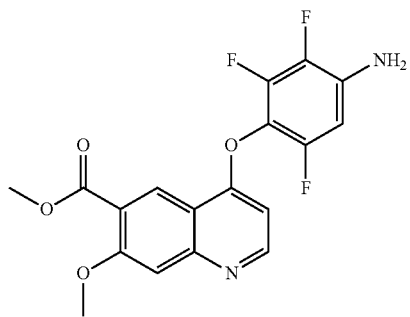 [SMILES: COC(=O)c1cc2c(Oc3c(F)cc(N)c(Cl)c3F)ccnc2cc1OC]
TABLE 3a-continued
"RM1" Structure in the First Step of Synthetic Method I
RM1-25
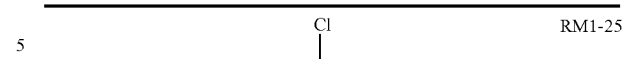
RM1-26
TABLE 3b
"RM2" Structure in the Second Step of Synthetic Method 1
RM2-01
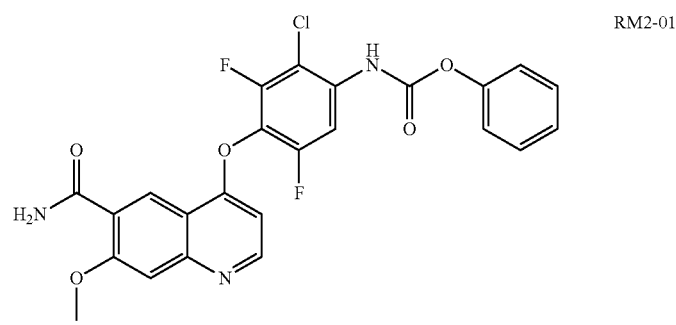

TABLE 3b-continued
"RM2" Structure in the Second Step of Synthetic Method 1
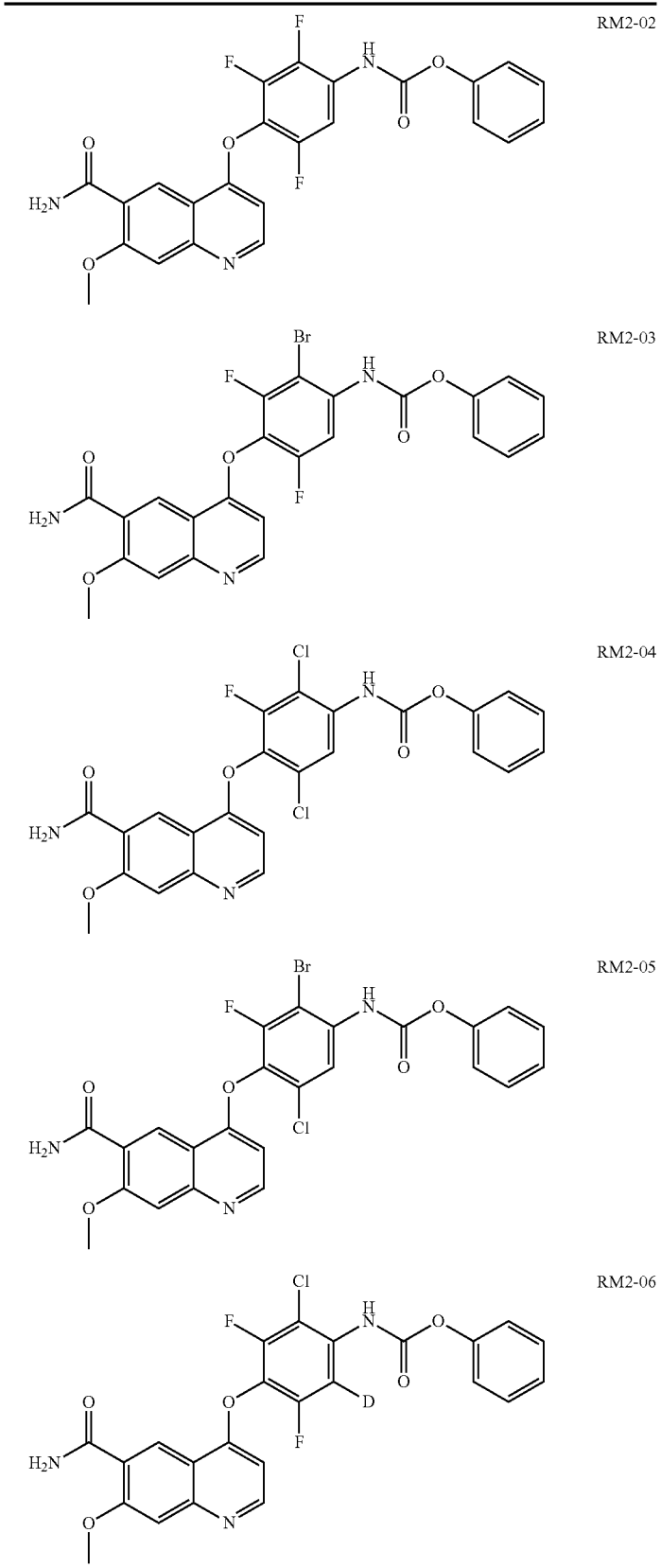
RM2-02
RM2-03
RM2-04
RM2-05
RM2-06

TABLE 3b-continued
"RM2" Structure in the Second Step of Synthetic Method 1
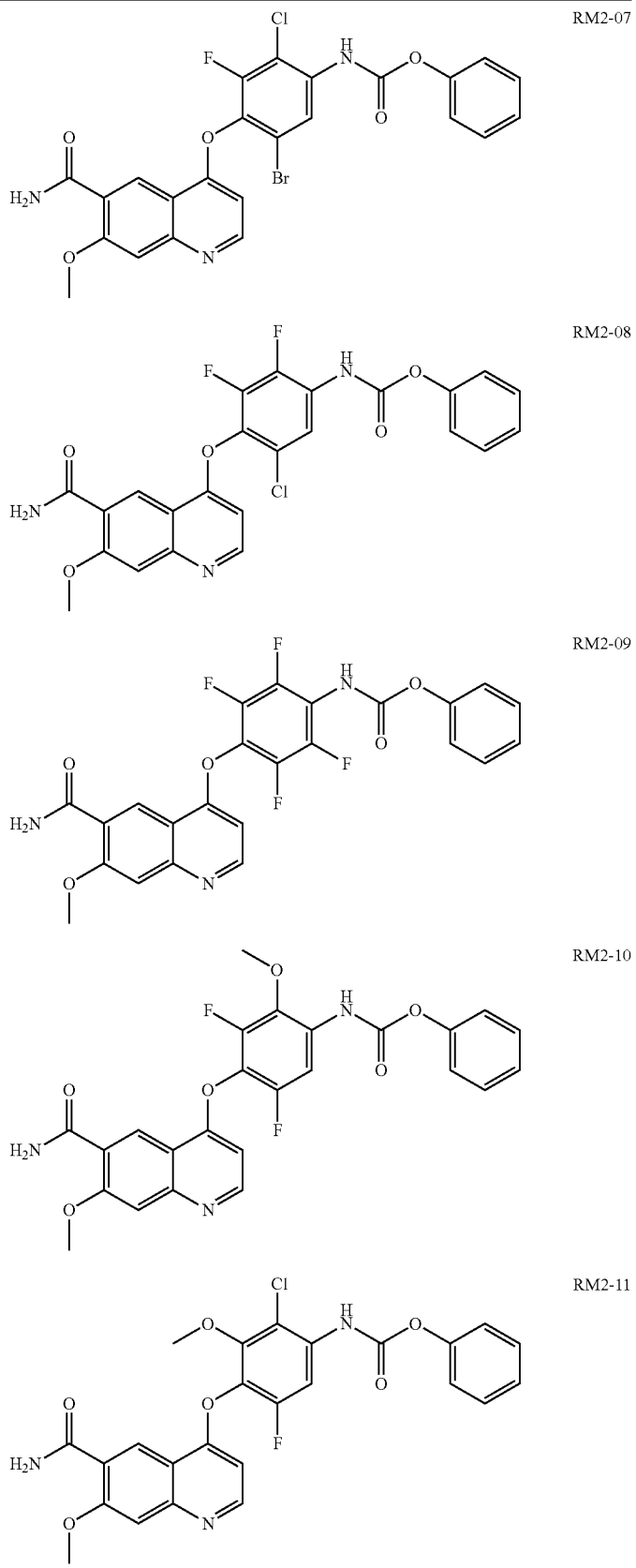
RM2-07
RM2-08
RM2-09
RM2-10
RM2-11

TABLE 3b-continued
"RM2" Structure in the Second Step of Synthetic Method 1
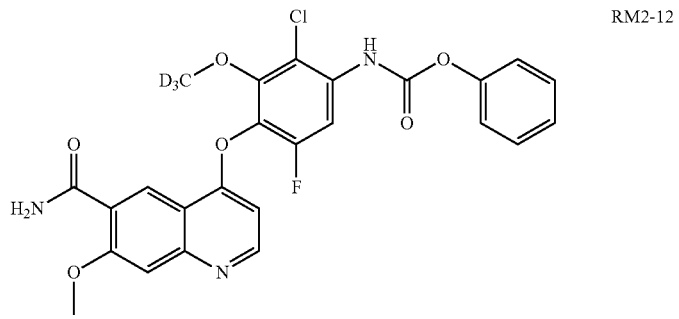
RM2-12
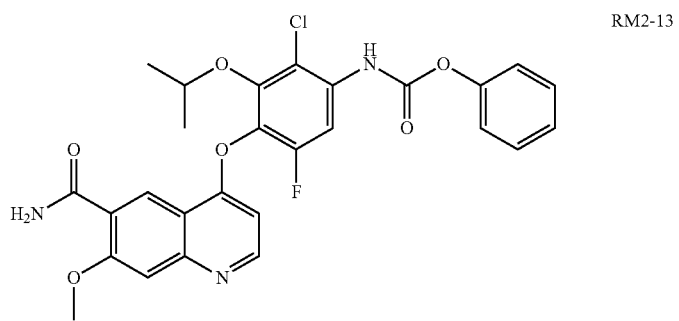
RM2-13
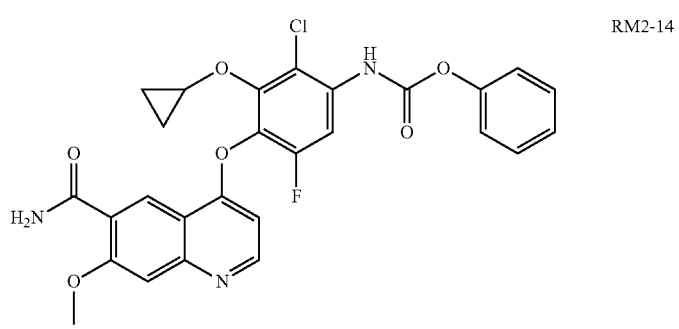
RM2-14
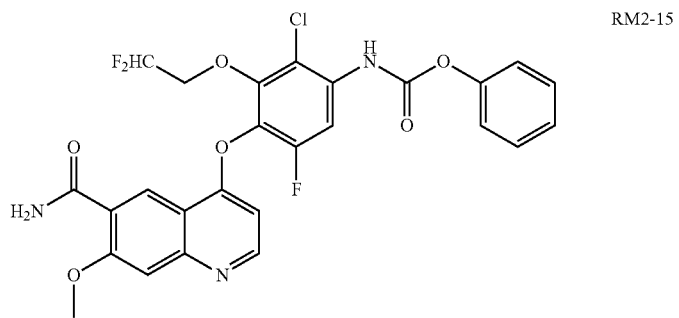
RM2-15

TABLE 3b-continued
"RM2" Structure in the Second Step of Synthetic Method 1
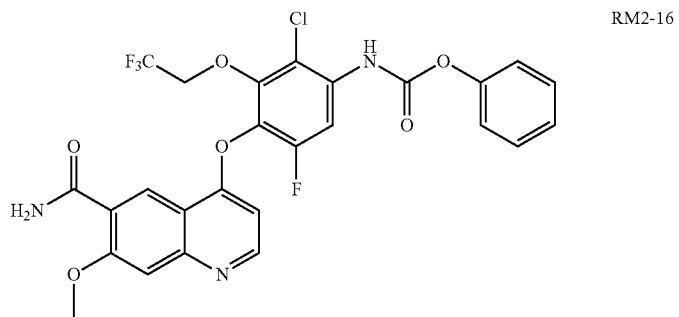
RM2-16
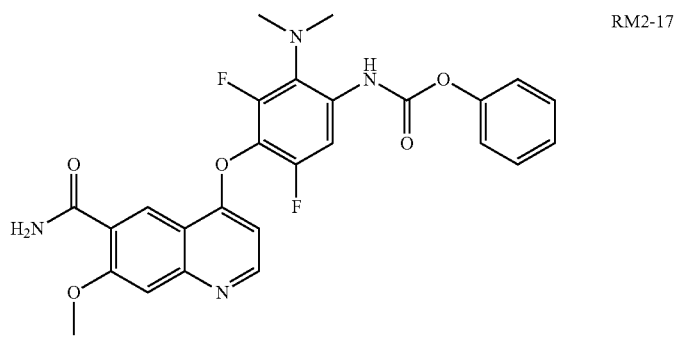
RM2-17
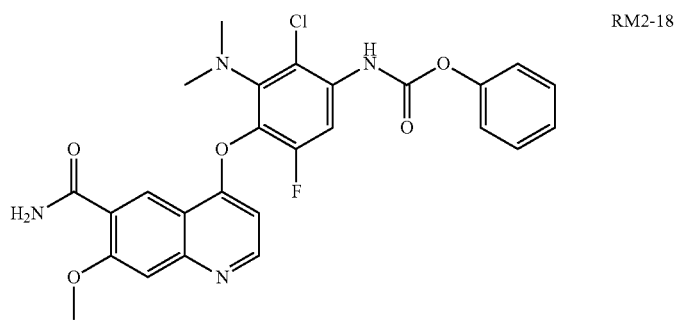
RM2-18
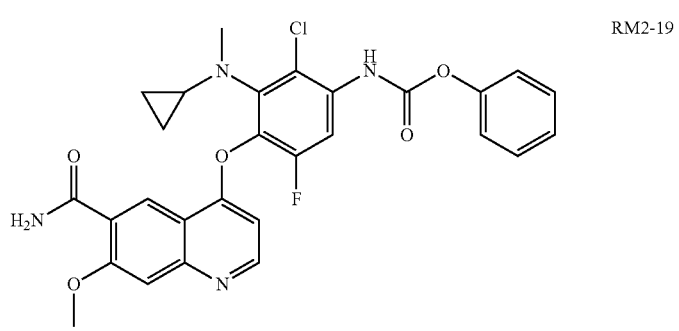
RM2-19

TABLE 3b-continued
"RM2" Structure in the Second Step of Synthetic Method 1
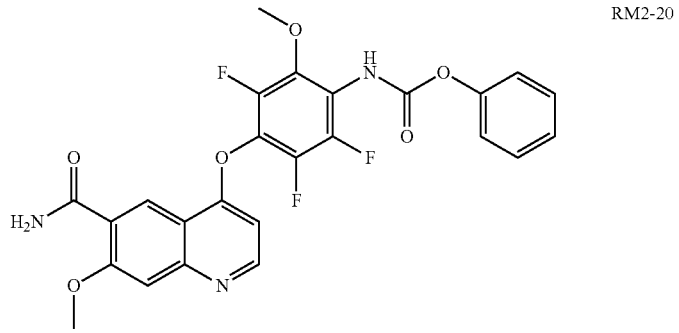
RM2-20
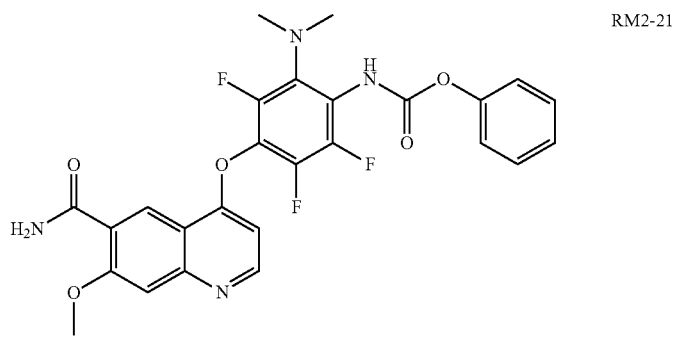
RM2-21
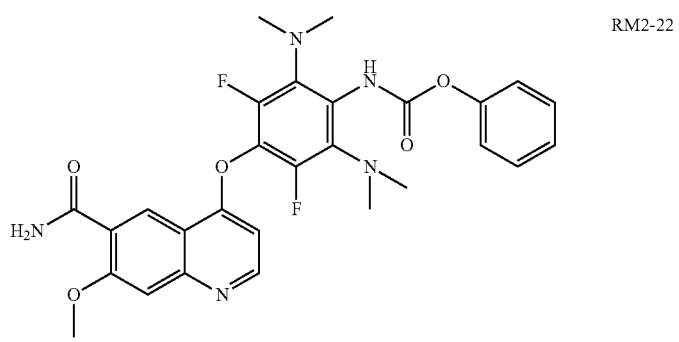
RM2-22
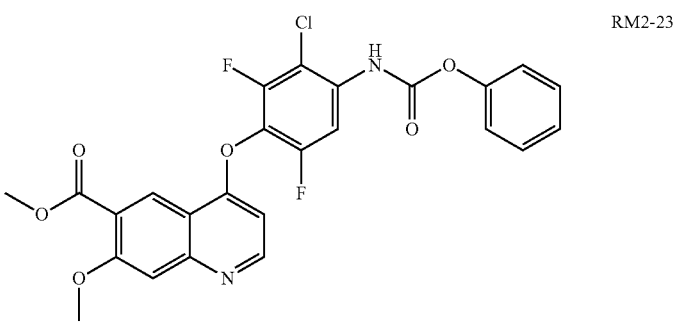
RM2-23

TABLE 3b-continued
"RM2" Structure in the Second Step of Synthetic Method 1
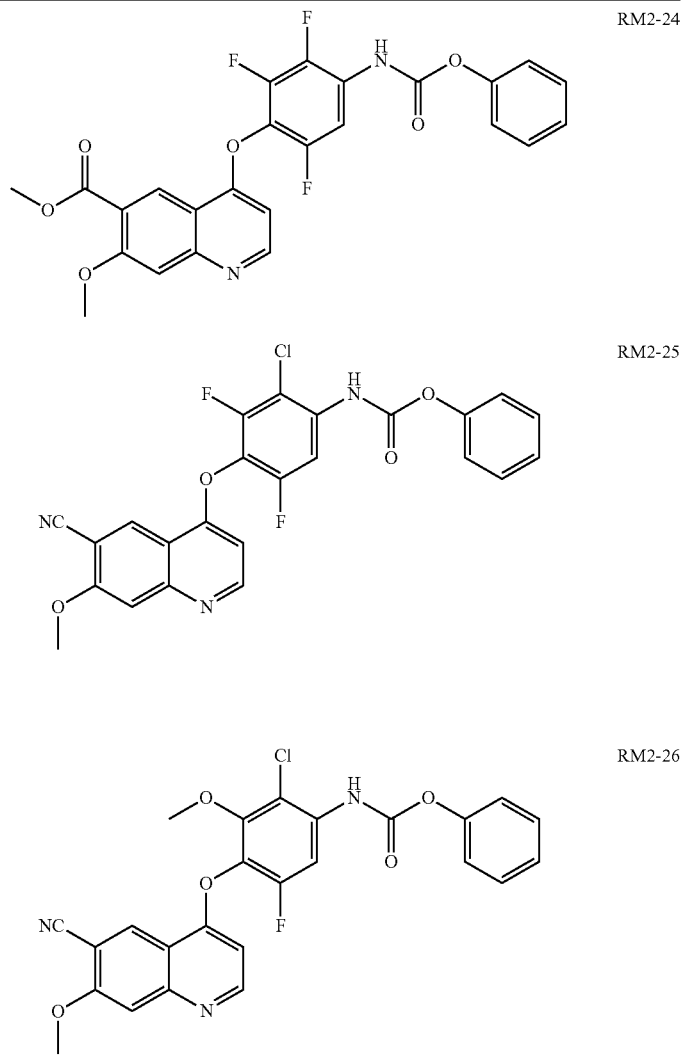
RM2-24
RM2-25
RM2-26
TABLE 3c
"RM3" Structure in the third Step of Synthetic Method 1
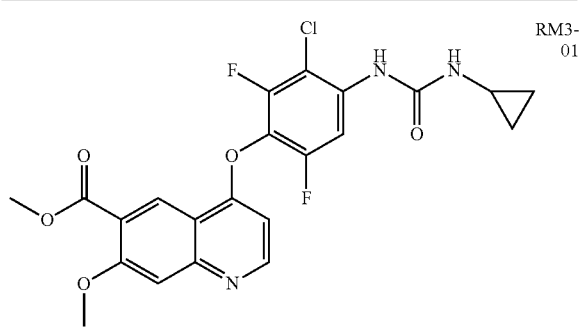
RM3-01
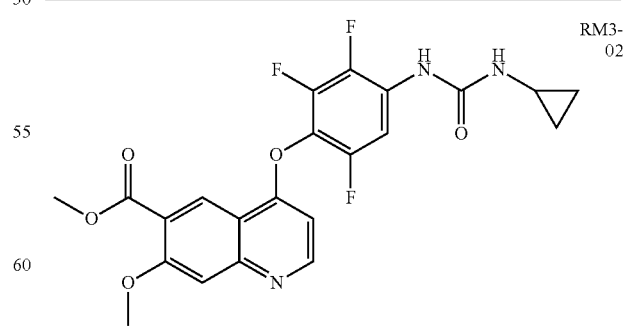
RM3-02

TABLE 3d
"RM4" Structure in the fourth Step of Synthetic Method 1
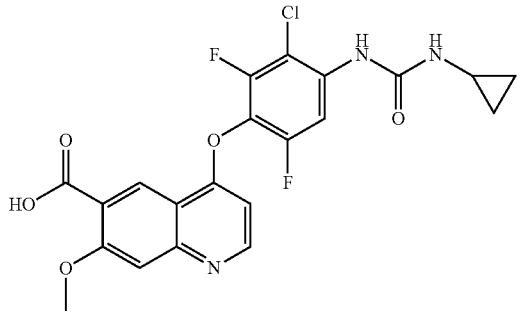
RM4-01
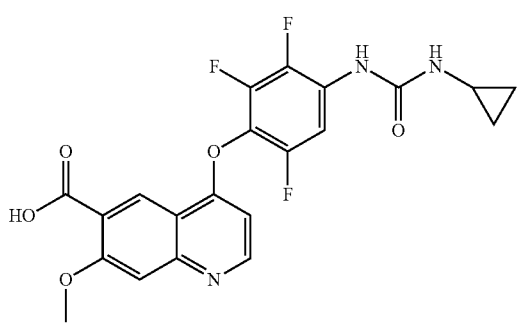 [SMILES: COc1cc2nccc(Oc3c(F)cc(NC(=O)NC4CC4)c(Cl)c3F)c2cc1C(=O)O]
RM4-02
TABLE 3e
"RM1b" Structure in the Synthetic Method 2
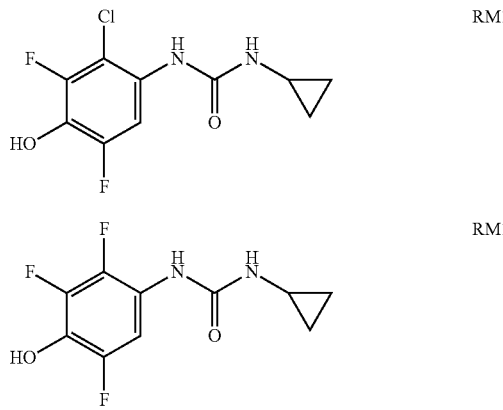
RM1b-01
RM1b-02
TABLE 4a
Starting Materials SM3
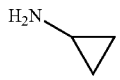
SM3-01
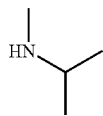
SM3-02
TABLE 4a-continued
Starting Materials SM3
| | |
|---|---|
| 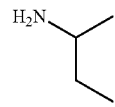 | SM3-03 |
| 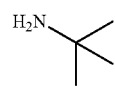 | SM3-04 |
| 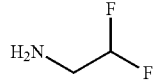 | SM3-05 |
| 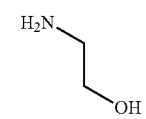 | SM3-06 |
| 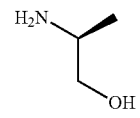 | SM3-07 |
| 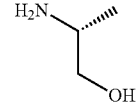 | SM3-08 |
| 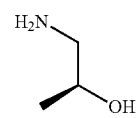 | SM3-09 |
| 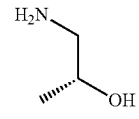 | SM3-10 |
| 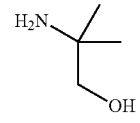 | SM3-11 |
| 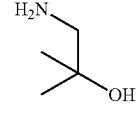 | SM3-12 |
| 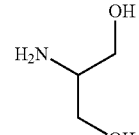 | SM3-13 |
| 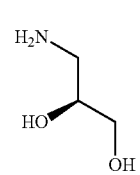 | SM3-14 |

TABLE 4a-continued

Starting Materials SM3

| Structure | ID |
|---|---|
| H2N-CH2-CH(OH)-CH2-OH (S) | SM3-15 |
| (CH3)2CH-NH2 | SM3-16 |
| 1-methylcyclopropylamine | SM3-17 |
| 2,2-difluorocyclopropylamine | SM3-18 |
| cyclopropylmethylamine | SM3-19 |
| cyclobutylamine | SM3-20 |
| 3-aminooxetane | SM3-21 |
| 4-aminotetrahydropyran | SM3-22 |
| cis-3-aminocyclobutanol | SM3-23 |
| trans-3-aminocyclobutanol | SM3-24 |
| (S)-3-hydroxypyrrolidine | SM3-25 |
| (R)-3-hydroxypyrrolidine | SM3-26 |
| 1-methylpiperazine | SM3-27 |
| 2-fluoroethylamine | SM3-28 |
| 1-amino-N-cyclopropyl-2-vinylcyclopropanecarboxamide | SM3-29 |
| 1,1,1-trifluoro-2-aminopropane | SM3-30 |
| 1-(trifluoromethyl)cyclopropylamine | SM3-31 |

TABLE 4b

Starting Materials SM4

| Structure | ID |
|---|---|
| CH3NH2·HCl | SM4-01 |
| (CH3)2NH | SM4-02 |
| isopropylamine | SM4-03 |
| 2-fluoroethylamine | SM4-04 |
| 2,2-difluoroethylamine | SM4-05 |
| 2,2,2-trifluoroethylamine | SM4-06 |
| N,N-dimethylethylenediamine | SM4-07 |
| cyclopropylamine | SM4-08 |
| dicyclopropylamine | SM4-09 |
| azetidine | SM4-10 |
| 2-methoxyethylamine | SM4-11 |
| 2-aminoethanol | SM4-12 |

TABLE 4b-continued

Starting Materials SM4

| Structure | ID |
|---|---|
| (R)-2-aminopropan-1-ol | SM4-13 |
| (S)-2-aminopropan-1-ol | SM4-14 |
| 2-amino-2-methylpropan-1-ol | SM4-15 |
| 2-aminopropane-1,3-diol | SM4-16 |
| (R)-3-aminopropane-1,2-diol | SM4-17 |
| (S)-3-aminopropane-1,2-diol | SM4-18 |
| (1-aminocyclopropyl)methanol | SM4-19 |
| azetidin-3-ol | SM4-20 |
| (R)-pyrrolidin-3-ol | SM4-21 |
| (S)-pyrrolidin-3-ol | SM4-22 |
| 1-methylpiperazine | SM4-23 |
| 1-methylpiperidin-4-amine | SM4-24 |
| methyl 1-aminocyclopropane-1-carboxylate | SM4-25 |
| 2,2-difluorocyclopropan-1-amine·HCl | SM4-26 |
| methanesulfonamide | SM4-27 |
| cyclopropanesulfonamide | SM4-28 |
| (R)-5-(aminomethyl)pyrrolidin-2-one | SM4-29 |
| (S)-5-(aminomethyl)pyrrolidin-2-one | SM4-30 |
| 6-aminopyrimidine-2,4(1H,3H)-dione | SM4-31 |
| 2-chloropyrimidin-4-amine | SM4-32 |
| 1,1,1-trifluoropropan-2-amine | SM4-33 |
| 1,1,1-trifluoro-2-methylpropan-2-amine | SM4-34 |
| 1-(trifluoromethyl)cyclopropan-1-amine | SM4-35 |

TABLE 4b-continued
Starting Materials SM4
| | |
|---|---|
| 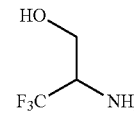 | SM4-36 |
| 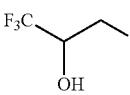 | SM4-37 |
| NC—NH$_2$ | SM4-38 |
| 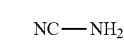 | SM4-39 |
|  | SM4-40 |
|  | SM4-41 |
| 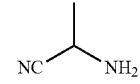 | SM4-42 |
|  | SM4-43 |
|  | SM4-44 |
| 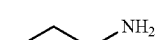 | SM4-45 |
| 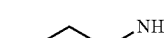 | SM4-46 |
| 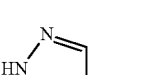 | SM4-47 |
| 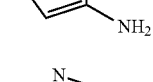 | SM4-48 |
TABLE 5
Formula IIIb Product Structure Obtained by Synthetic Method 1 or 2
Structure of Formula IIIb Products
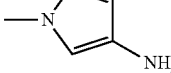
IIIb-01
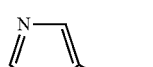
IIIb-02

TABLE 5-continued
Formula IIIb Product Structure Obtained by Synthetic Method 1 or 2
Structure of Formula IIIb Products
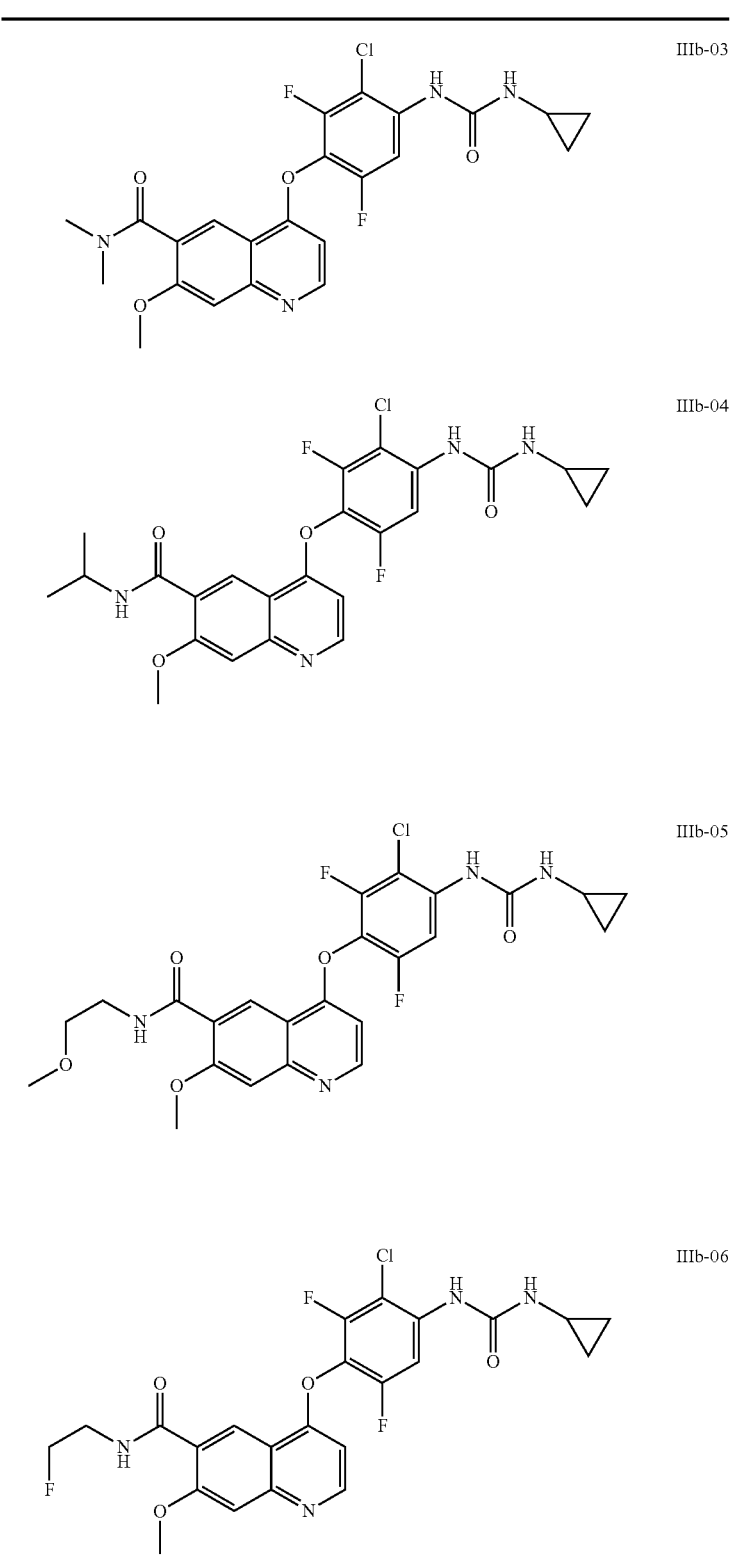

TABLE 5-continued
Formula IIIb Product Structure Obtained by Synthetic Method 1 or 2
Structure of Formula IIIb Products
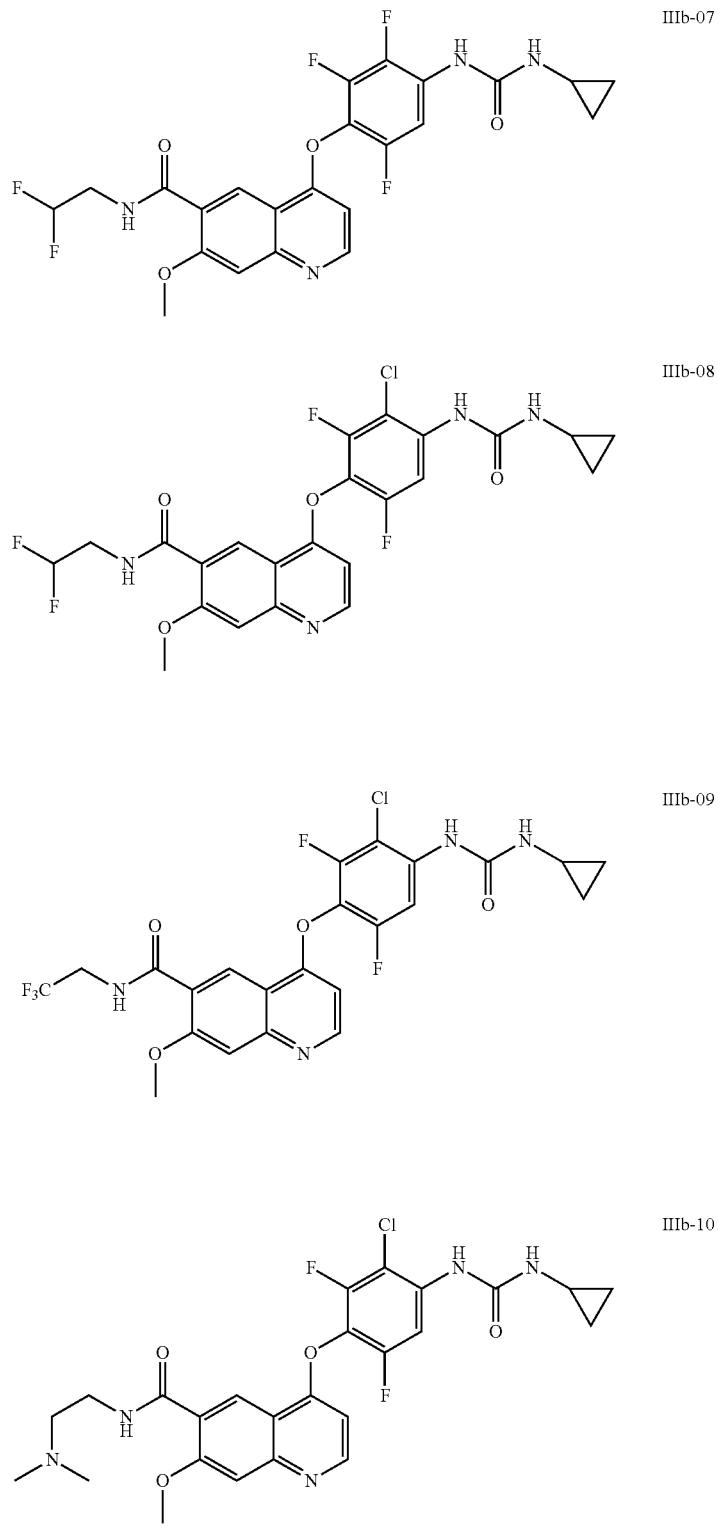

TABLE 5-continued
Formula IIIb Product Structure Obtained by Synthetic Method 1 or 2
Structure of Formula IIIb Products
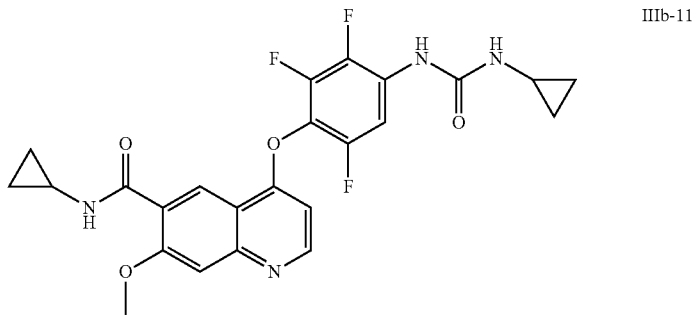
IIIb-11
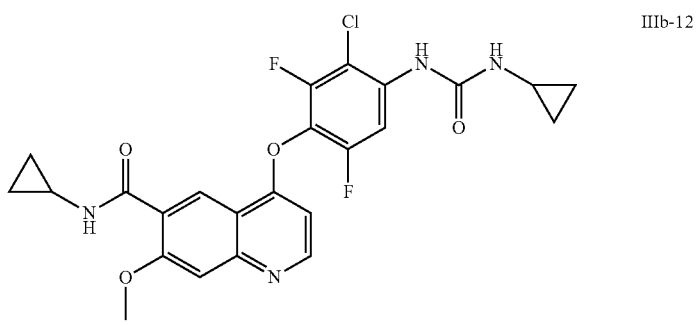
IIIb-12
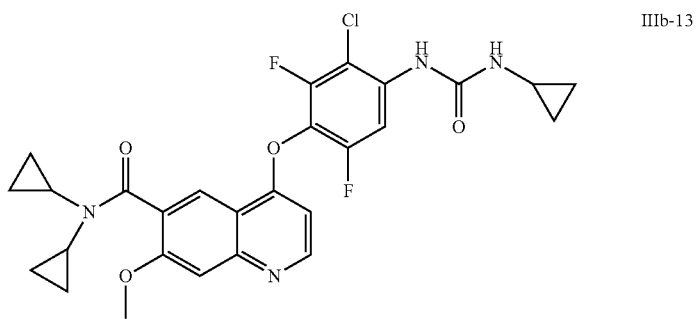
IIIb-13
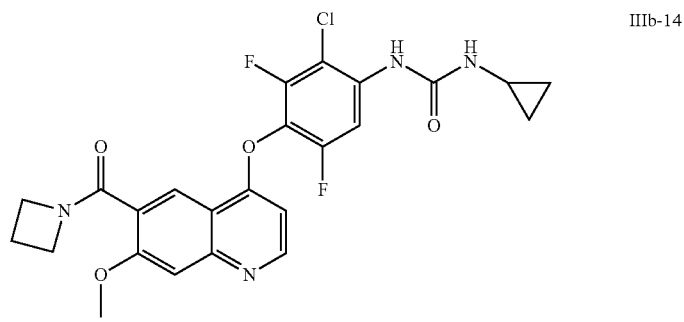
IIIb-14

TABLE 5-continued
Formula IIIb Product Structure Obtained by Synthetic Method 1 or 2
Structure of Formula IIIb Products
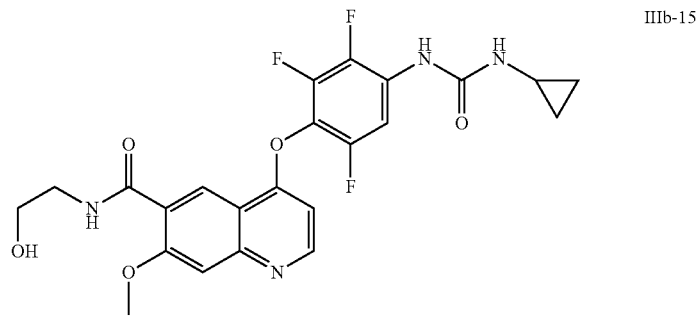
IIIb-15
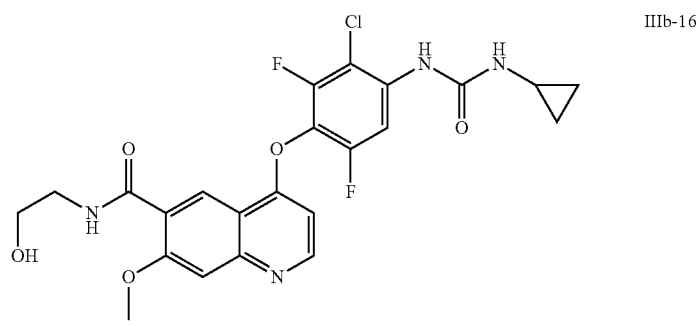
IIIb-16
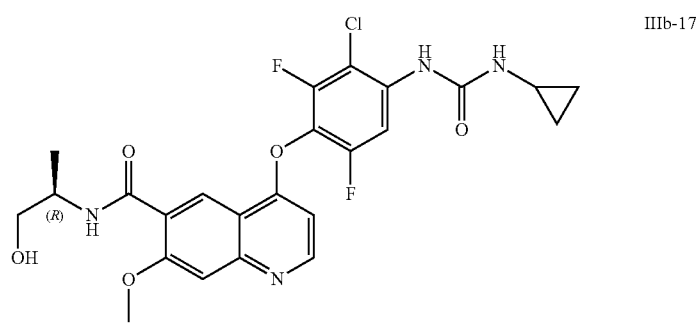
IIIb-17
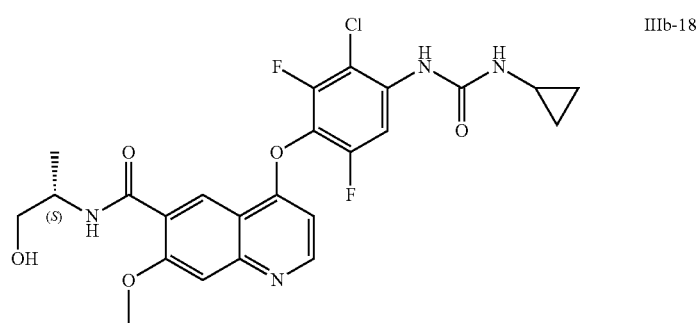
IIIb-18

TABLE 5-continued
Formula IIIb Product Structure Obtained by Synthetic Method 1 or 2
Structure of Formula IIIb Products
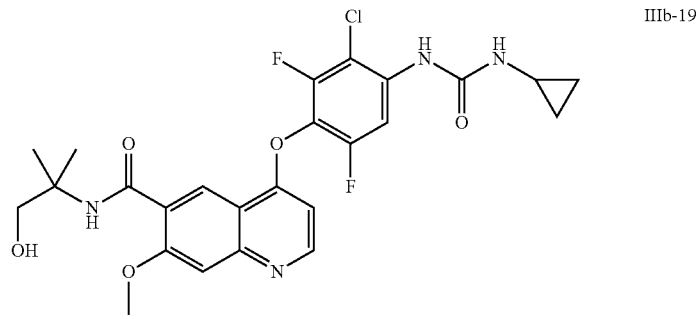
IIIb-19
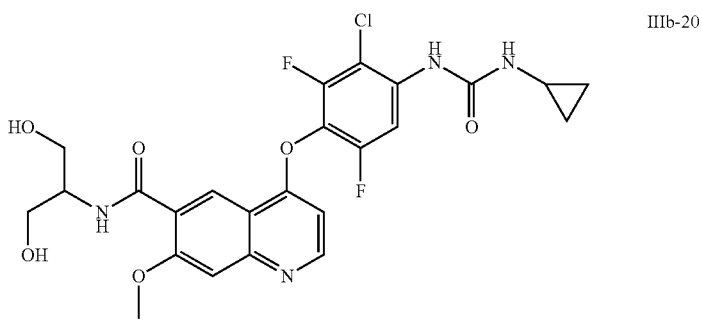
IIIb-20
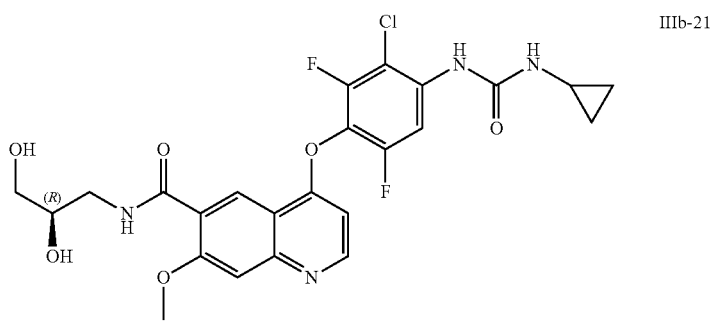
IIIb-21
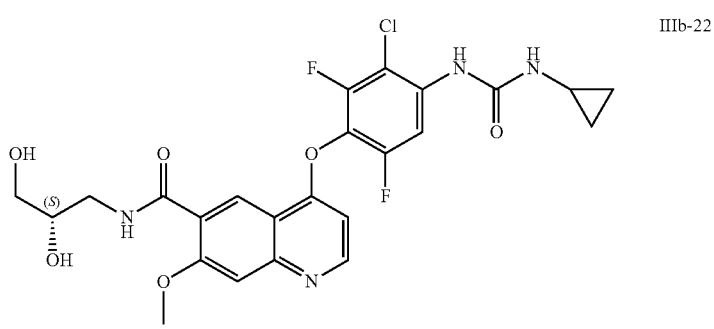
IIIb-22

TABLE 5-continued
Formula IIIb Product Structure Obtained by Synthetic Method 1 or 2
Structure of Formula IIIb Products
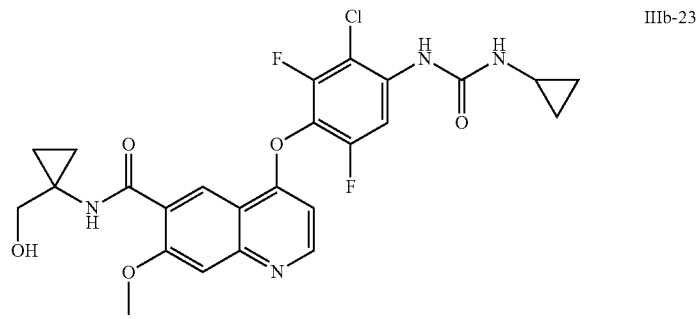
IIIb-23
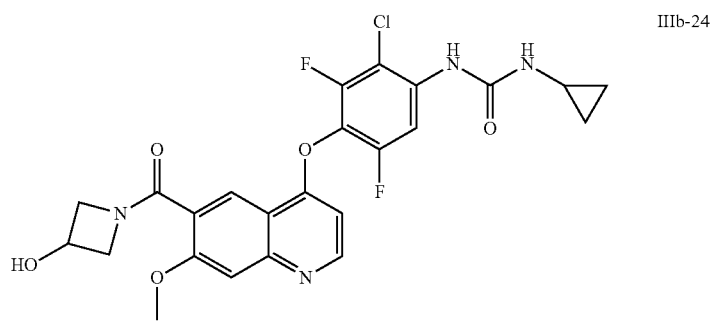
IIIb-24
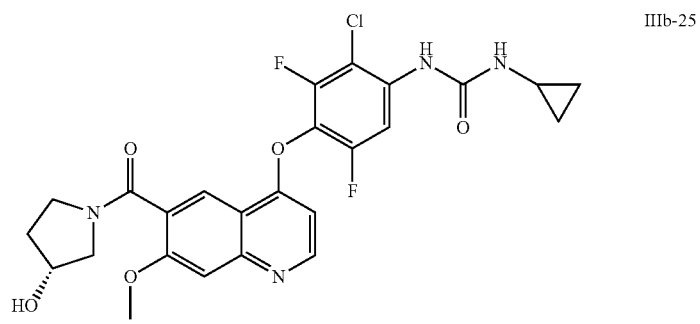
IIIb-25
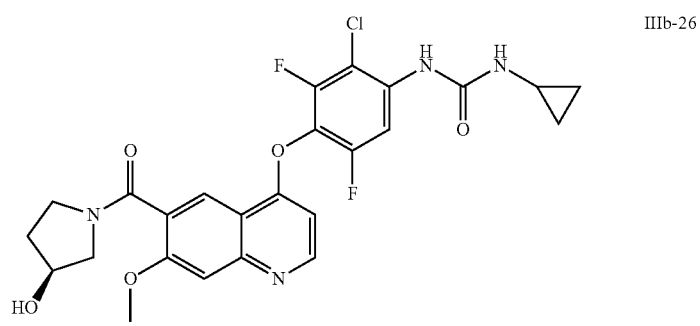
IIIb-26

TABLE 5-continued
Formula IIIb Product Structure Obtained by Synthetic Method 1 or 2
Structure of Formula IIIb Products
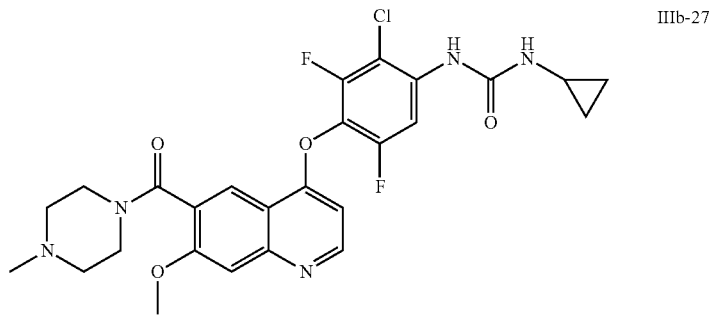
IIIb-27
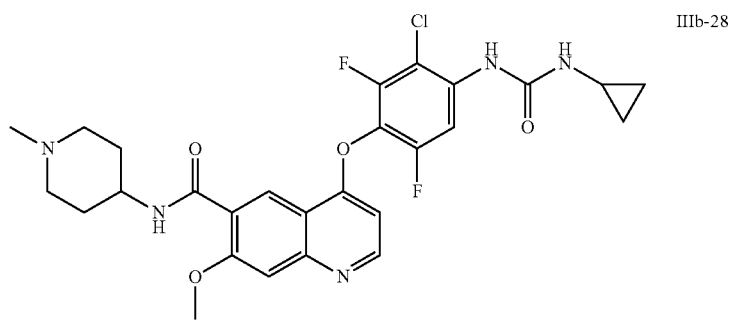
IIIb-28
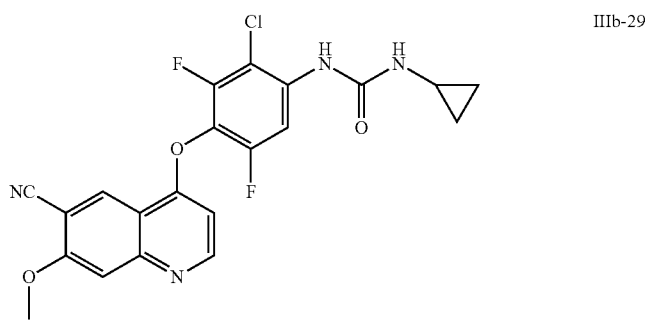
IIIb-29
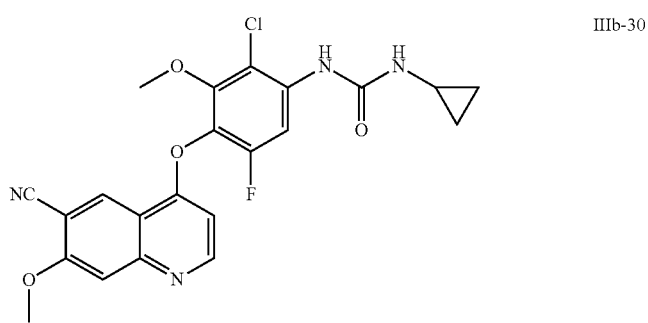
IIIb-30

TABLE 5-continued
Formula IIIb Product Structure Obtained by Synthetic Method 1 or 2
Structure of Formula IIIb Products
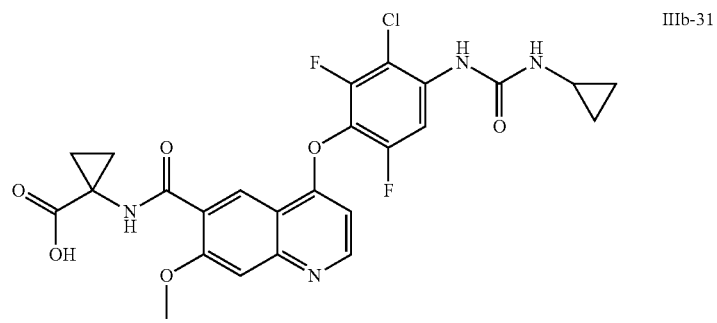
IIIb-31
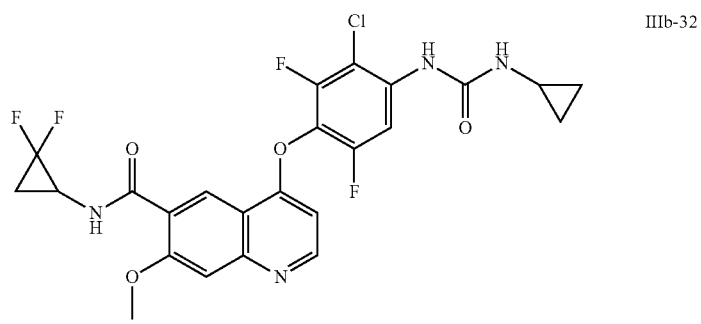
IIIb-32
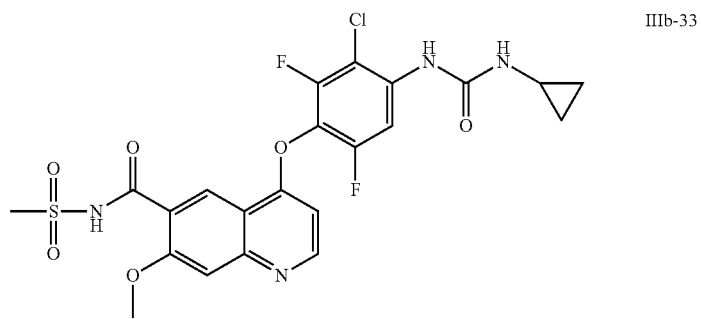
IIIb-33
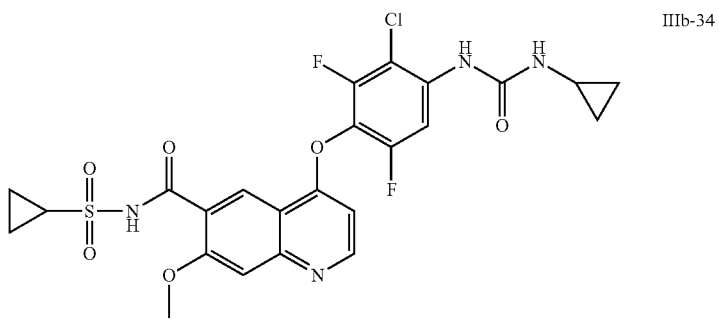
IIIb-34

TABLE 5-continued
Formula IIIb Product Structure Obtained by Synthetic Method 1 or 2
Structure of Formula IIIb Products
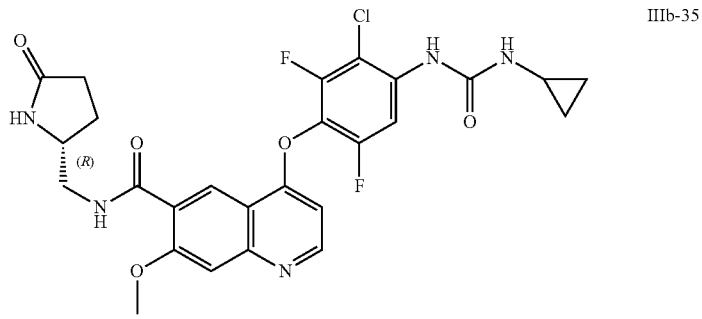
IIIb-35
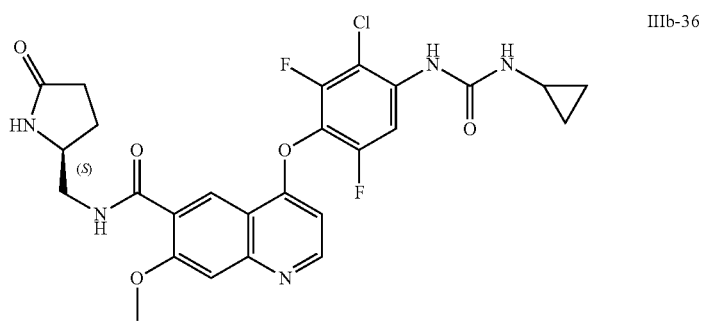
IIIb-36
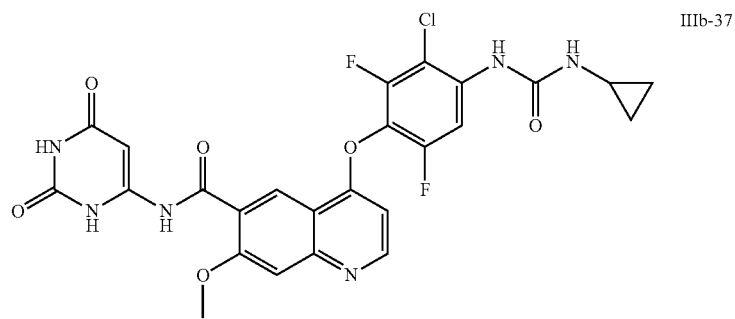
IIIb-37
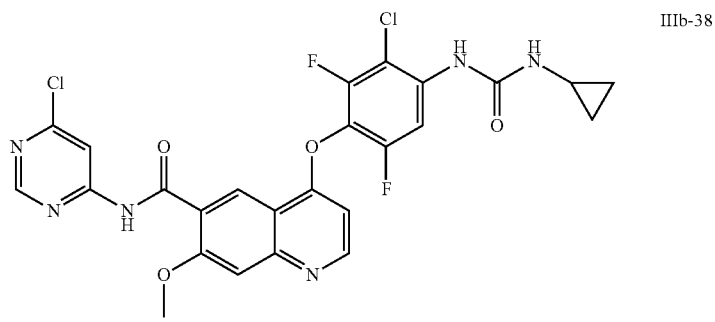
IIIb-38

TABLE 5-continued
Formula IIIb Product Structure Obtained by Synthetic Method 1 or 2
Structure of Formula IIIb Products
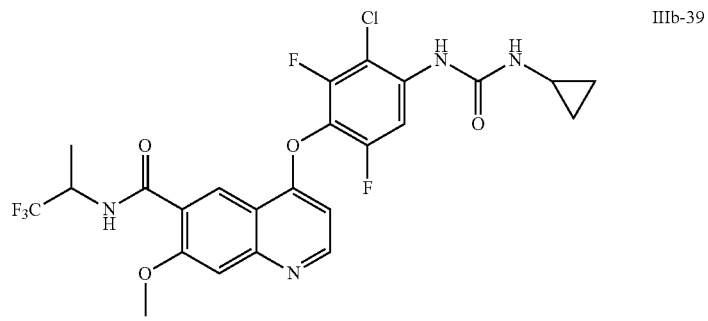
IIIb-39
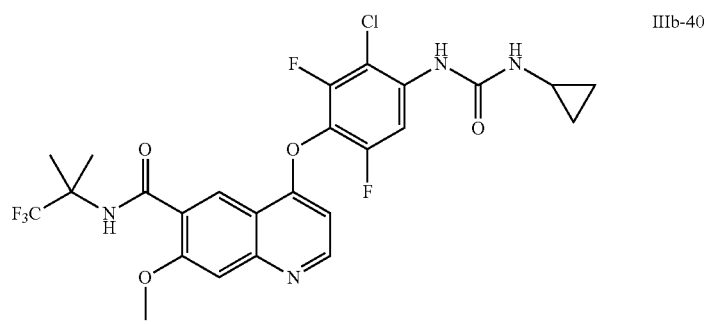
IIIb-40
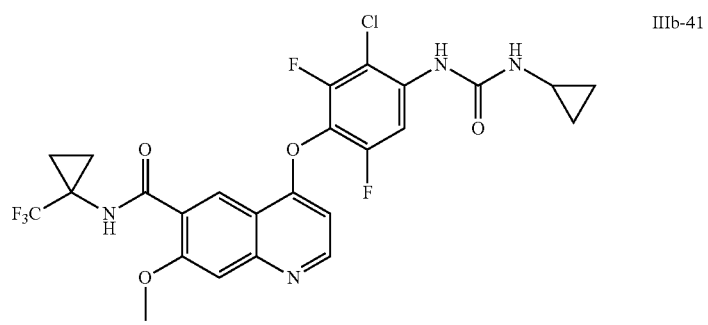
IIIb-41
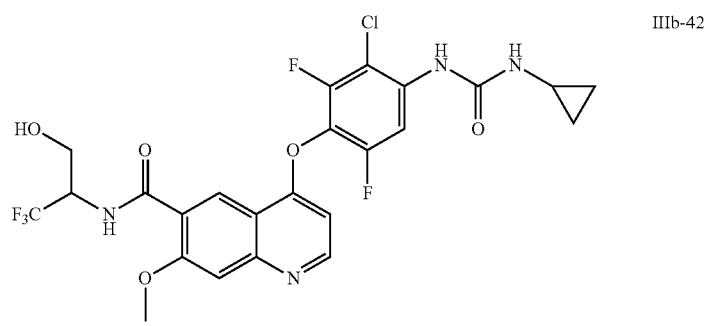
IIIb-42

TABLE 5-continued
Formula IIIb Product Structure Obtained by Synthetic Method 1 or 2
Structure of Formula IIIb Products
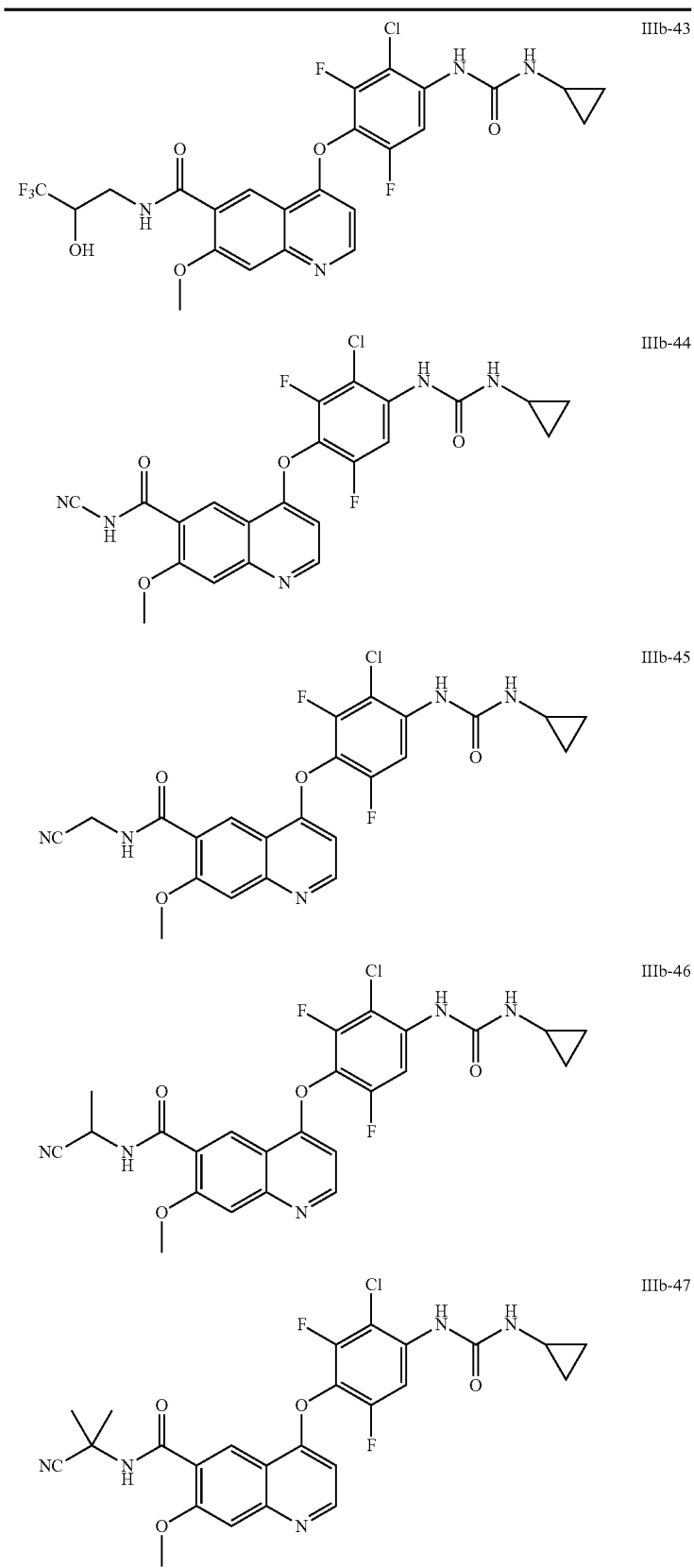

TABLE 5-continued
Formula IIIb Product Structure Obtained by Synthetic Method 1 or 2
Structure of Formula IIIb Products
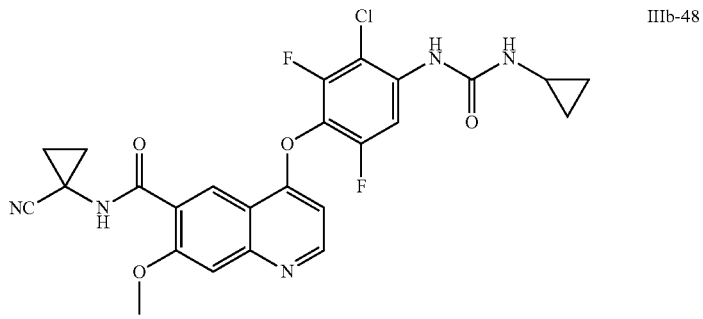
IIIb-48
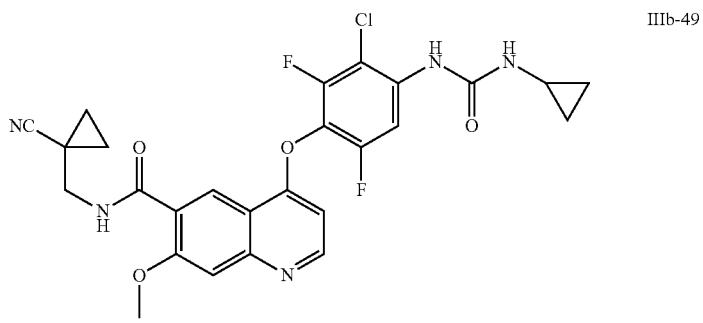
IIIb-49
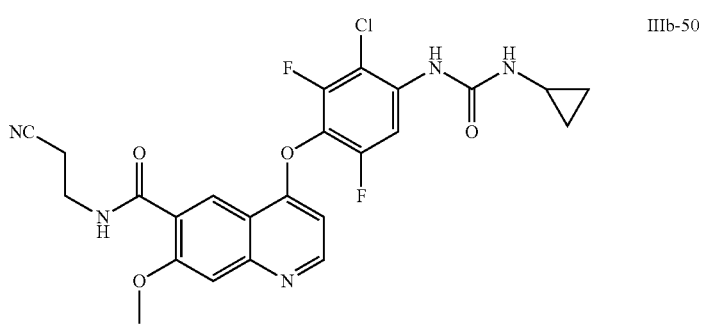
IIIb-50
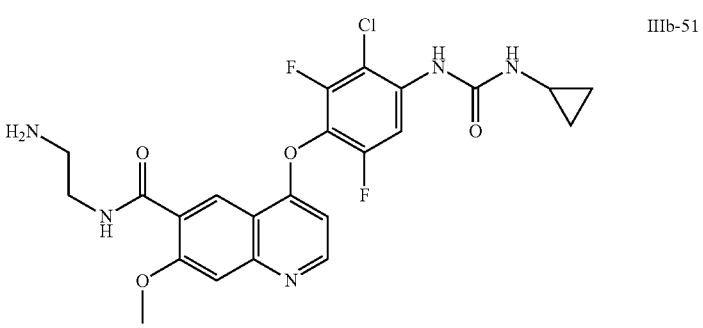
IIIb-51

TABLE 5-continued
Formula IIIb Product Structure Obtained by Synthetic Method 1 or 2
Structure of Formula IIIb Products
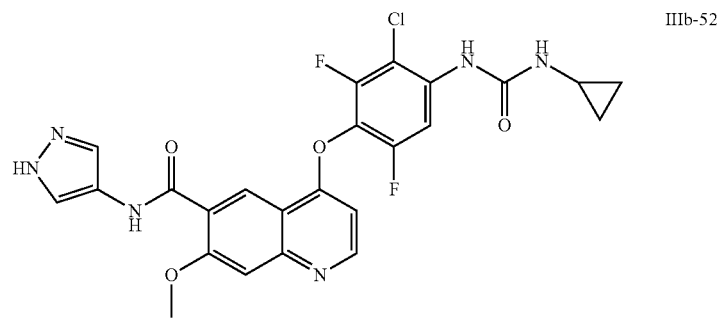
IIIb-52
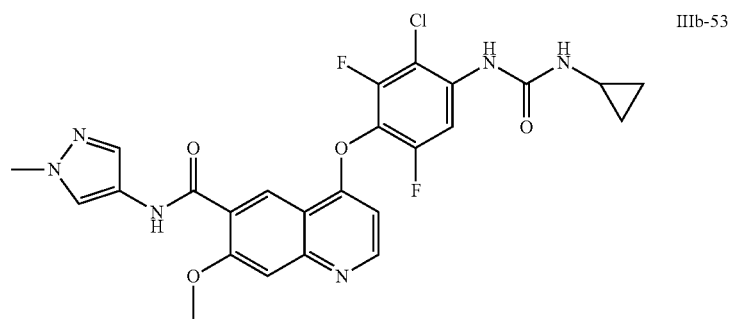
IIIb-53
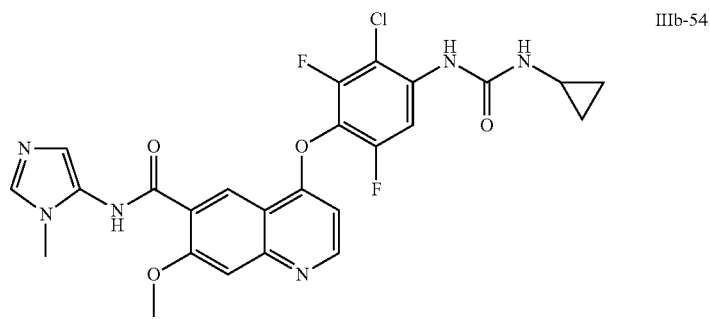
IIIb-54
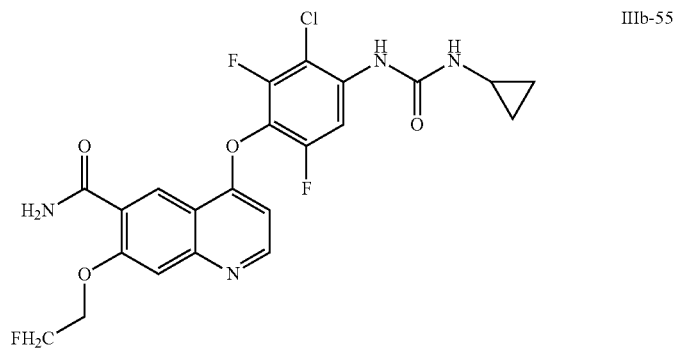
IIIb-55

TABLE 5-continued
Formula IIIb Product Structure Obtained by Synthetic Method 1 or 2
Structure of Formula IIIb Products
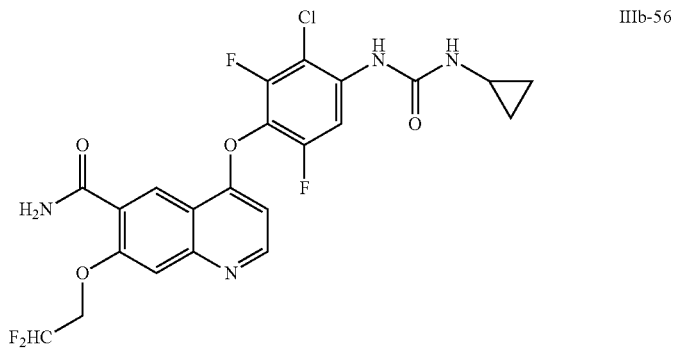
IIIb-56
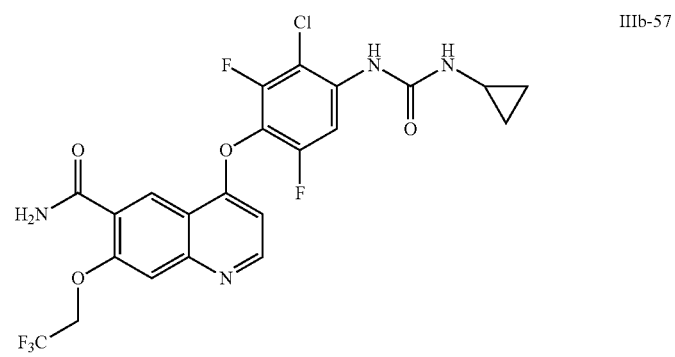
IIIb-57
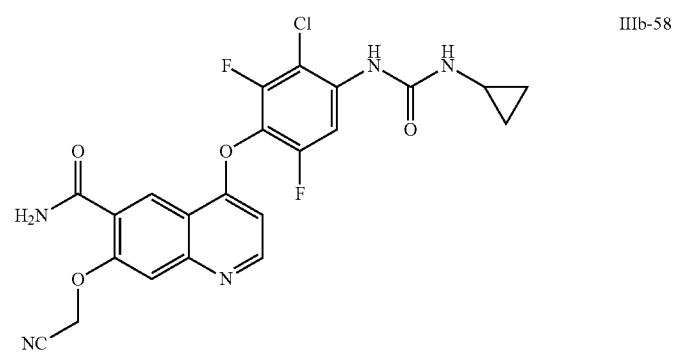
IIIb-58
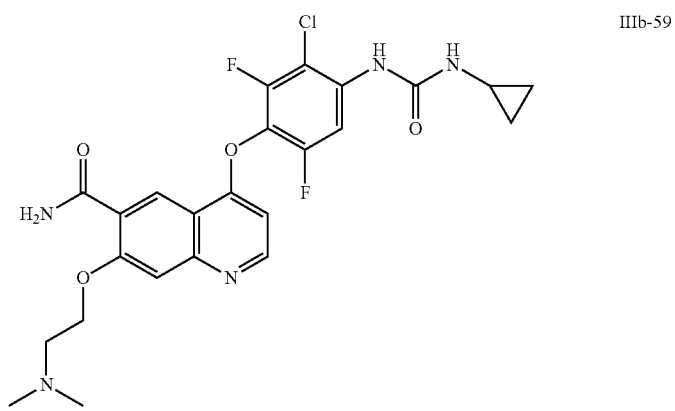
IIIb-59

TABLE 5-continued
Formula IIIb Product Structure Obtained by Synthetic Method 1 or 2
Structure of Formula IIIb Products
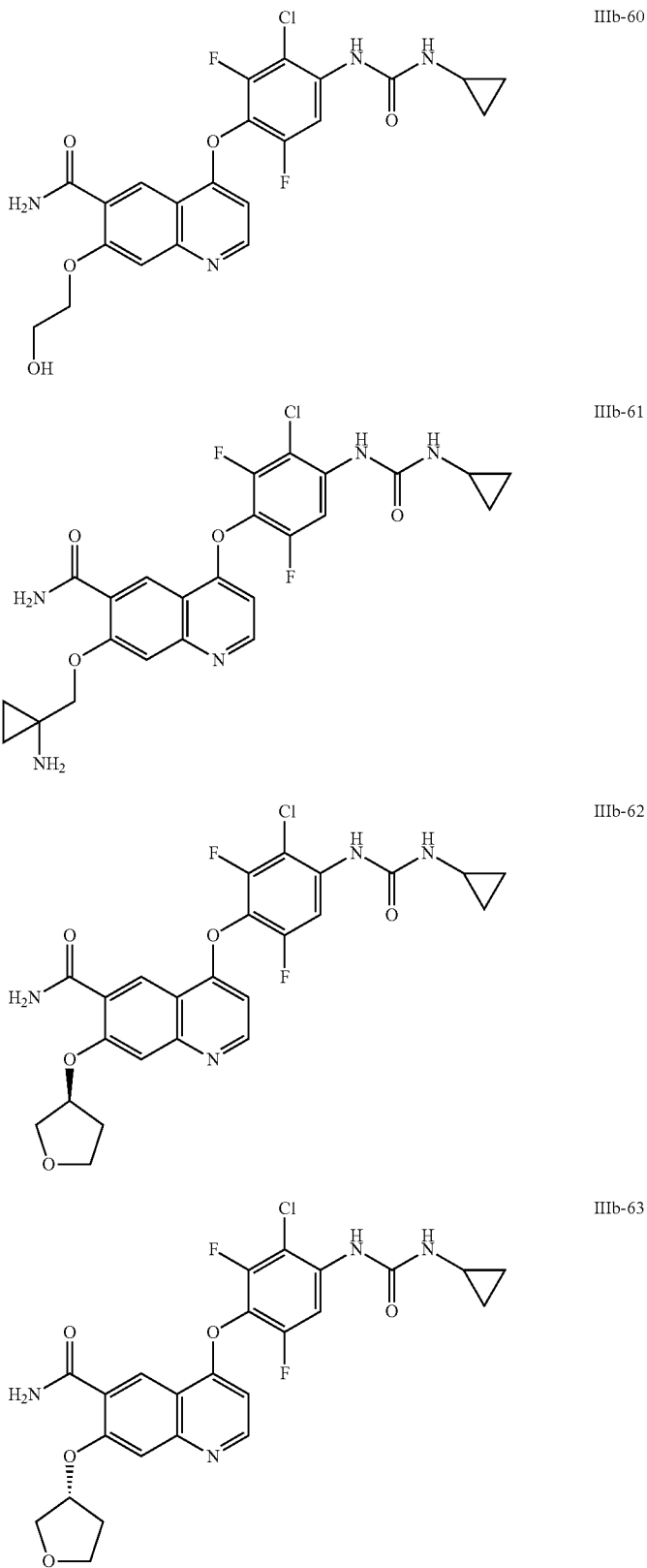
IIIb-60
IIIb-61
IIIb-62
IIIb-63

TABLE 5-continued

Formula IIIb Product Structure Obtained by Synthetic Method 1 or 2
Structure of Formula IIIb Products

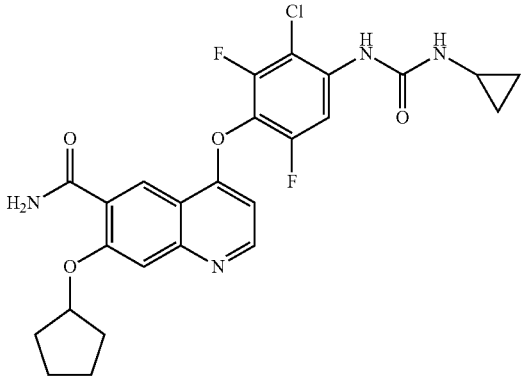

IIIb-64

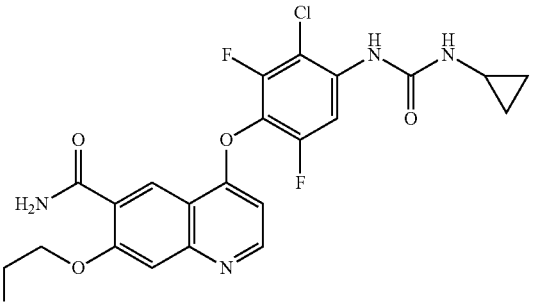

IIIb-65

In the present invention, in addition to the synthesis of compounds IIIb-01 to IIIb-65 prepared in the corresponding Examples 1 to 52 by the above synthetic methods, it is also possible to synthesize some of the deuterated compounds listed in Table 6 below, which are prepared by using some deuterated reagents in which one or more of the hydrogens in SM1, SM2 and SM3 are replaced by deuterium isotopes, respectively, under the protection of a safety device. The compounds listed in Table 6 below can be synthesized under the protection of a safety device with one or several of the "H" of the IIIb compounds specified in claims 1~5 replaced by deuterium (D) isotopes (e.g., IIIb-66, IIIb-67, IIIb-68, IIIb-69, IIIb-70, IIIb-71, IIIb-72, IIIb-73, IIIb-74, IIIb-75, IIIb-76, IIIb-77, IIIb-78, IIIb-79, IIIb-80, IIIb-81, IIIb-82, IIIb-83, IIIb-84, IIIb-85, IIIb-86, IIIb-87, IIIb-88 and IIIb-89 etc.) or all hydrogen (H) of the formula IIIb compounds are replaced by the deuterium (D) isotope.

TABLE 6

Structure of Some Easily Deuterated Isotopic Formula IIIb Compounds

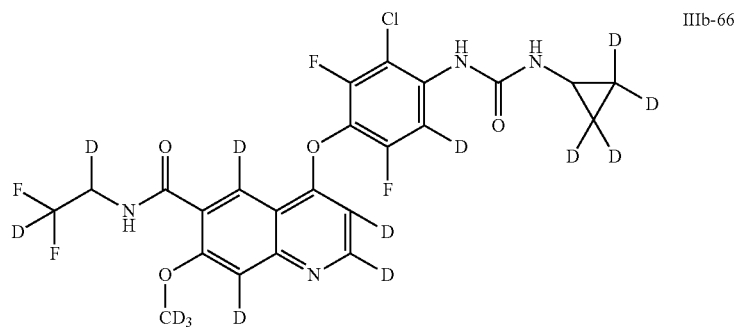

IIIb-66

TABLE 6-continued
Structure of Some Easily Deuterated Isotopic Formula IIIb Compounds
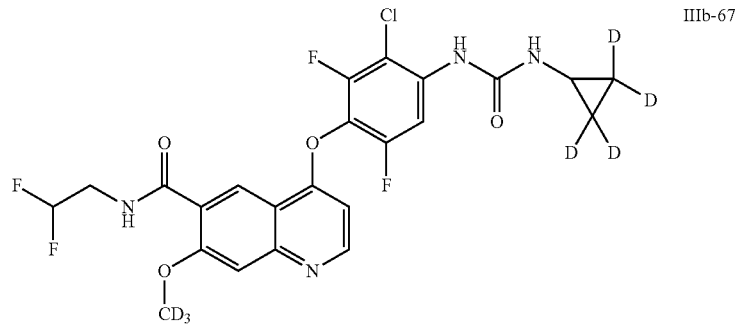
IIIb-67
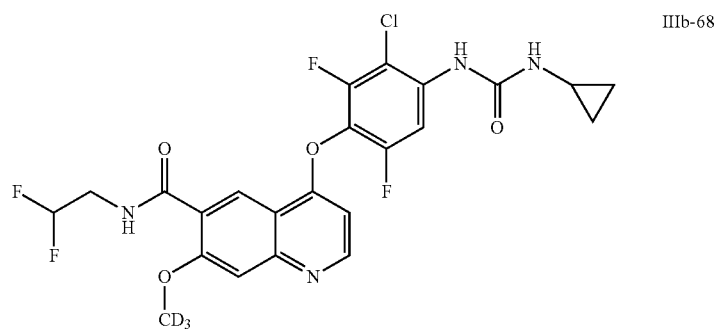
IIIb-68
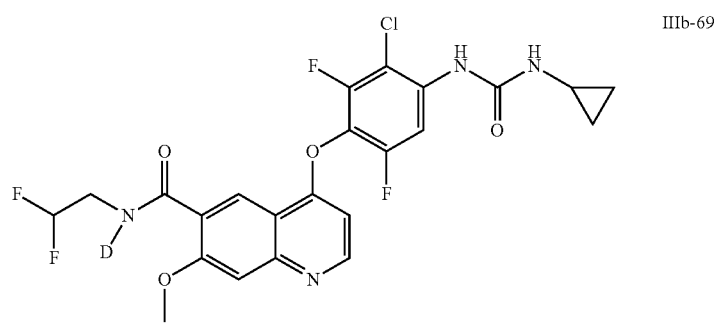
IIIb-69
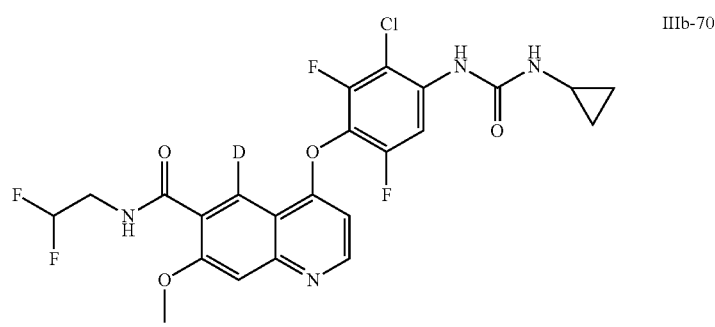
IIIb-70

TABLE 6-continued
Structure of Some Easily Deuterated Isotopic Formula IIIb Compounds
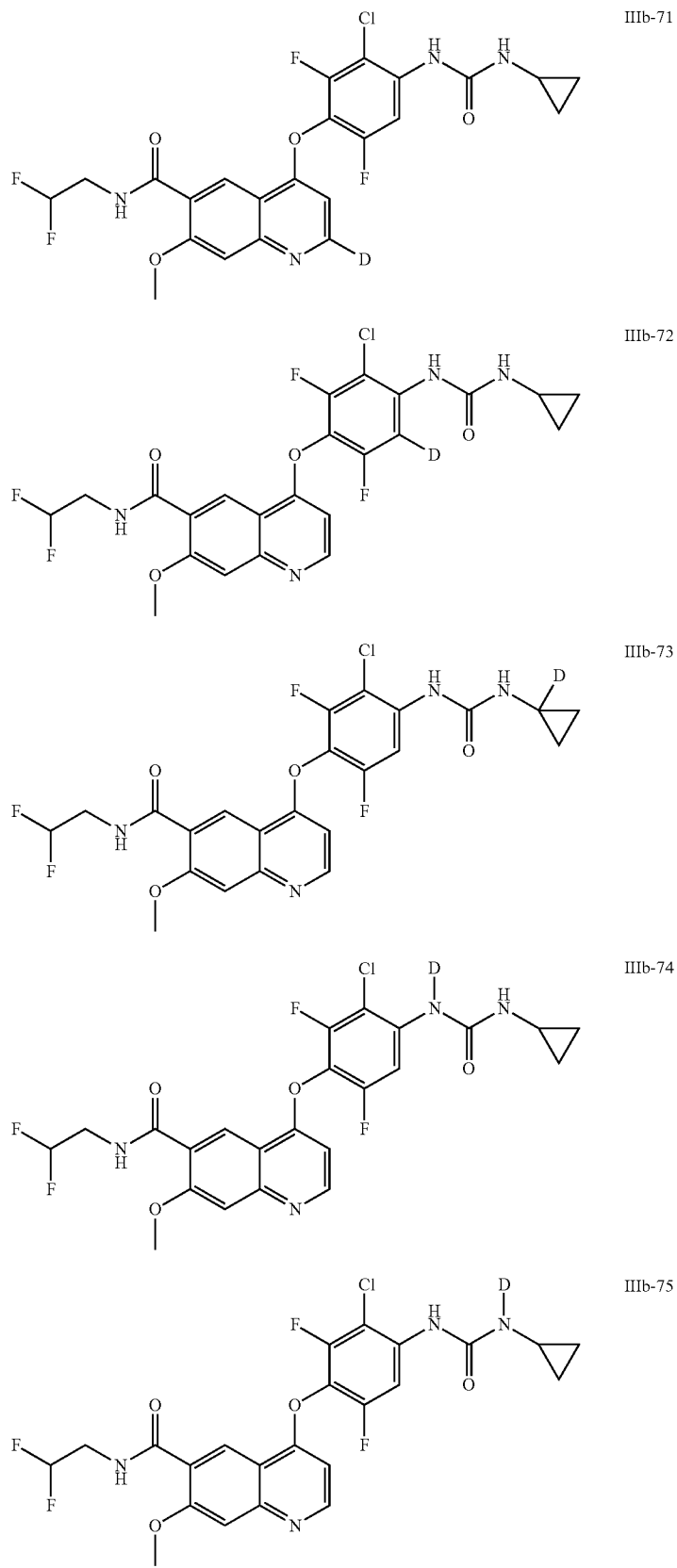
IIIb-71
IIIb-72
IIIb-73
IIIb-74
IIIb-75

TABLE 6-continued
Structure of Some Easily Deuterated Isotopic Formula IIIb Compounds
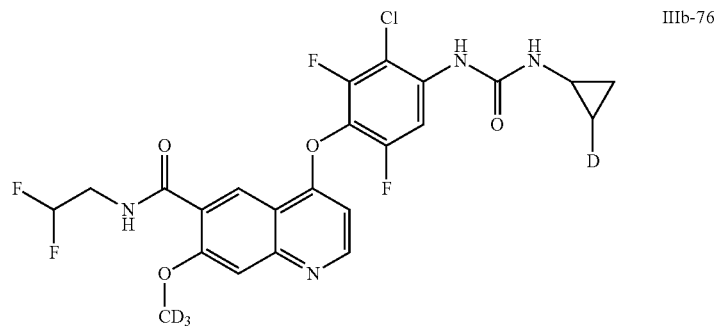
IIIb-76
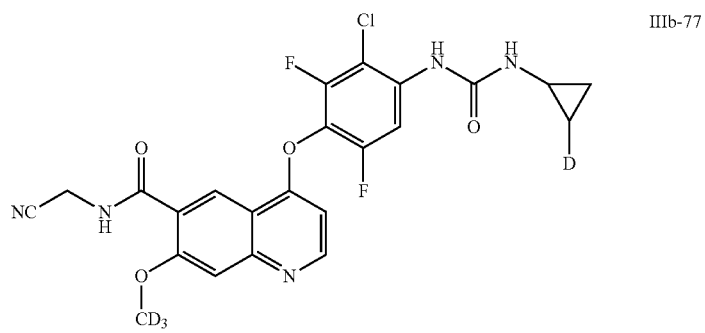
IIIb-77
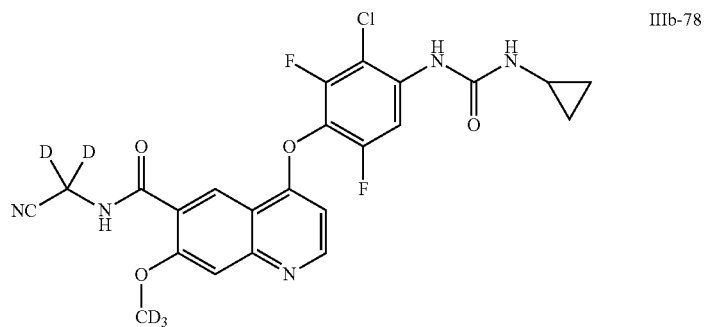
IIIb-78
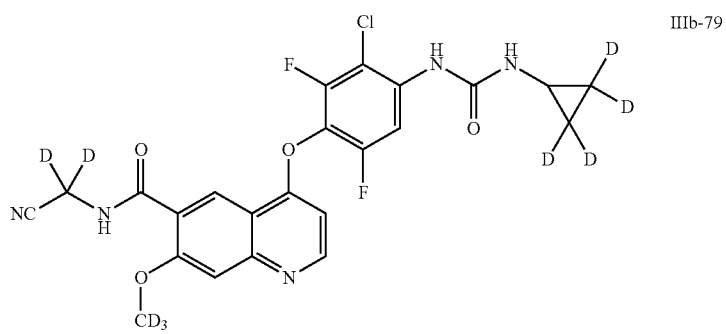
IIIb-79

TABLE 6-continued
Structure of Some Easily Deuterated Isotopic Formula IIIb Compounds
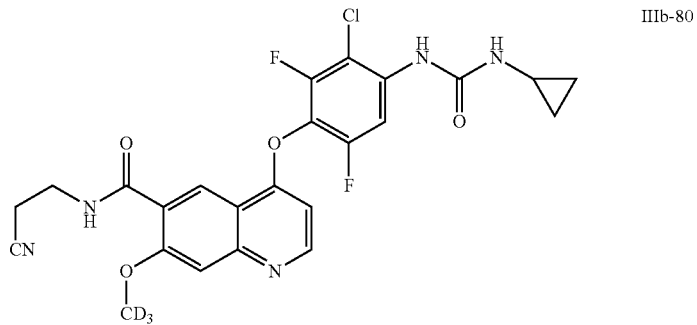
IIIb-80
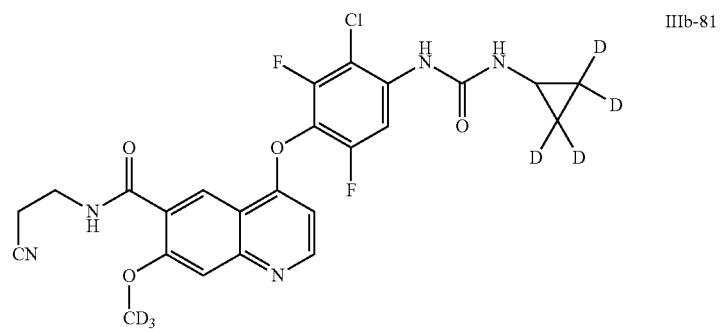
IIIb-81
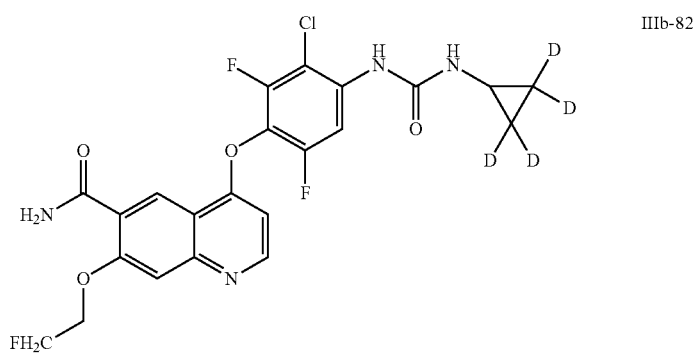
IIIb-82
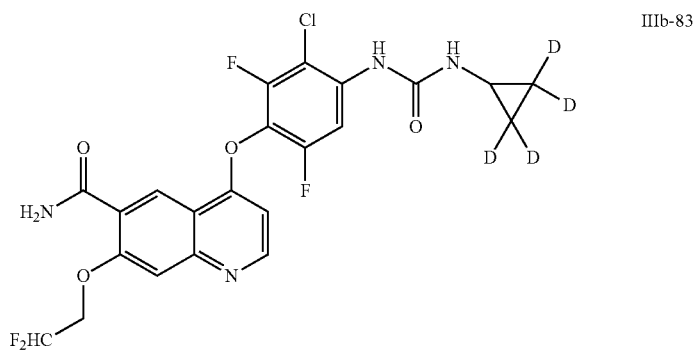
IIIb-83

TABLE 6-continued
Structure of Some Easily Deuterated Isotopic Formula IIIb Compounds
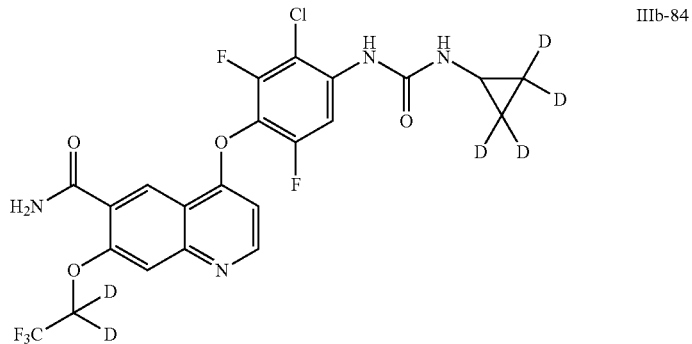
IIIb-84
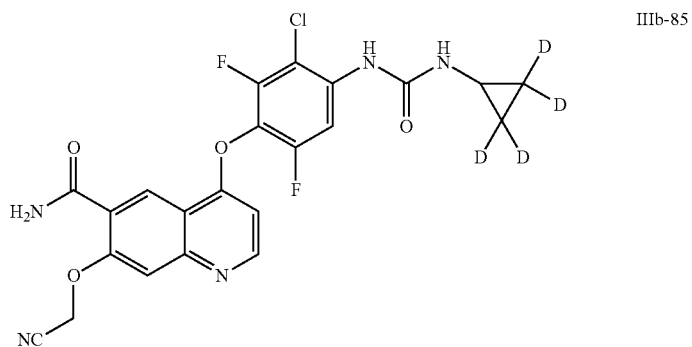
IIIb-85
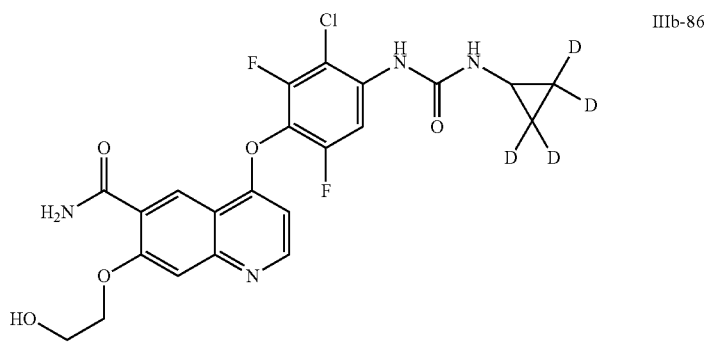
IIIb-86
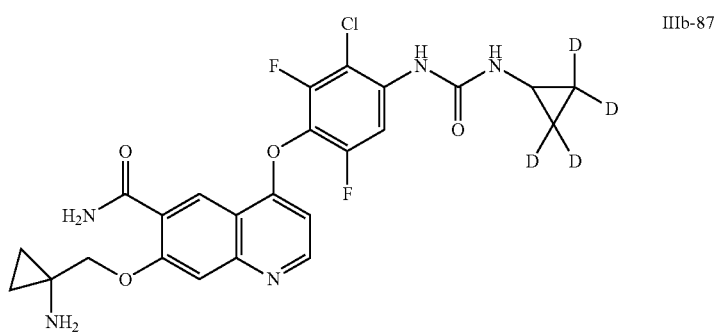
IIIb-87

TABLE 6-continued

Structure of Some Easily Deuterated Isotopic Formula IIIb Compounds

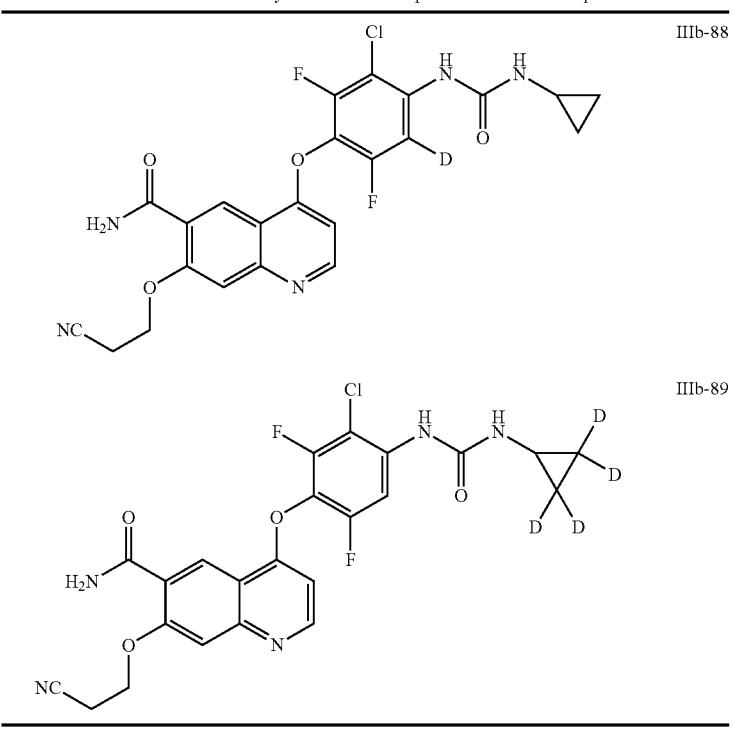

IIIb-88

IIIb-89

Specific results concerning the synthesis and analysis of the novel compounds of formula IIIb described above are detailed in the final embodiment of the present invention, and the structural characterization of each compound was determined by LC-MS and/or NMR ($^1$H-NMR, $^{13}$C-NMR and/or $^{19}$F-NMR) analysis, respectively.

In the following section were the detailed examples of the synthesis and biological activities of different kinds of compounds and their intermediates.

Instruments and Materials Related to Examples are as Follows

NMR ($^1$H-NMR, $^{13}$C-NMR and $^{19}$F-NMR spectra) were obtained from the analysis of an Ascend 400 m NMR instrument manufactured by Bruker. The chemical shifts were recorded with tetramethylsilane as internal standard, and the NMR analyses were all performed using deuterated DMSO, MeOH and other solvents, expressed in ppm (CHCl3: δ=7.26 ppm). The following data information was recorded: chemical shifts and their cleavage and coupling constants (s: single peak; d: double peak; t: triple peak; q: quadruple peak; br: broad peak; m: multiple peak).

The mass spectrometry data were analyzed using a liquid phase 1260 and mass spectrometry 6120 coupled by Agilent. The molecular weights of the compounds of formula IIIb in the present invention were mainly in cationic mode ESI-MS [(M+H)$^+$].

The special raw materials and intermediates involved in this invention are provided by Shanghai Zannan Technology Co., Ltd. and other custom processing, and all other chemical reagents are purchased from Shanghai Reagent Company, Aldrich Company, Acros Company and other reagent suppliers. If the intermediates or products required for the reaction during the synthesis are not enough for the next step and other tests, the synthesis is repeated several times until sufficient quantities are available. The activity tests of the compounds prepared by the invention as well as pharmacological and toxicological tests were done by CRO service companies in Shanghai and Beijing according to industry regulations.

The abbreviations of the relevant chemical raw materials, reagents and solvents involved in the present invention and its embodiments are annotated as follows.

Boc: tert-Butoxycarbonyl
(Boc)$_2$O: Di-tert-butyl dicarbonate
CDI: N'-carbonyl diimidazole
DBU: 1,8-diazabicyclo[5.4.0]undec-7-ene
EDCI: N-ethyl-N'-(3-dimethylaminopropyl)carbodiimide hydrochloride
HATU: 2-(7-azobenzotriazole)-N,N,N',N'-tetramethyluronium hexafluorophos phate
NBS: N-bromosuccinimide
NCS: N-chlorosuccinimide
SOCl$_2$: Sulfoxide chloride
Pd/C: Palladium carbon
DIEA: N,N-diisopropylethylamine
DMAP: 4-Dimethylaminopyridine
HMTA: Hexamethylenetetramine
Py: Pyridine
HBr: Hydrobromic acid
HCl: Hydrochloric acid
HOAc: Glacial acetic acid
TFA: Trifluoroacetic acid
MsOH: Methanesulfonic acid
TsOH: p-toluenesulfonic acid
Cs2CO3: Cesium carbonate
tBuOK: Potassium tert-butoxide
KOH: Potassium hydroxide
NaOH: Sodium hydroxide LiOH: Lithium hydroxide
ACN/MeCN: Acetonitrile
DCM: Dichloromethane
DCE: Dichloroethane
DMF: N,N-dimethylformamide
DMSO: Dimethyl sulfoxide
Et2O: Diethyl ether
EA: Ethyl acetate
PE: Petroleum ether
THF: Tetrahydrofuran
TBME: methyl tert-butyl ether
Me: Methyl
Et: Ethyl
Pr: Propyl
iPr: Isopropyl
cPr: Cyclopropyl
Ph: Phenyl The new multi-substituted functional compound SM2-01 and series of formula IIIb compounds IIIb-01 to IIIB-65 were synthesized according to the relevant synthetic methods shown above, respectively.

Example 1

Synthesis of Compound SM2-01

Method 1 for Synthesis of Compound SM2-01

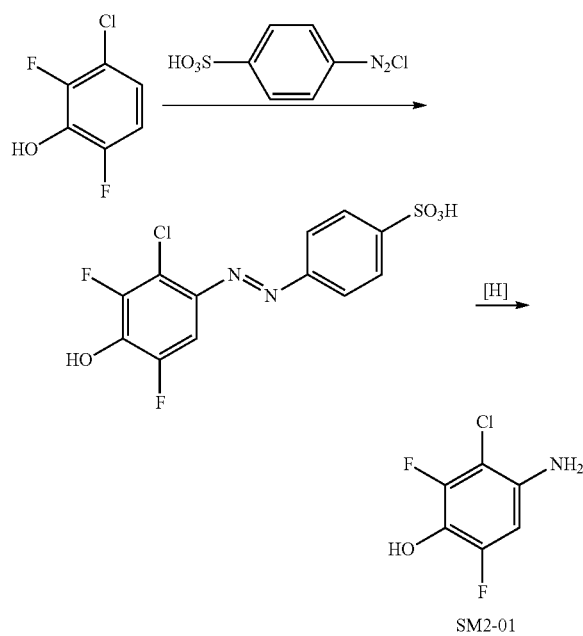

The solution of NaNO$_2$ (25 g in water 75 mL) was added dropwise to a mixture of p-aminobenzenesulfonic acid (60 g), water (500 mL) and Na$_2$CO$_3$ (20 g) in a 1 L three-mouth flask below 5° C. After the completion of adding the solution of NaNO$_2$, 12N—HCl was added dropwise to the mixture below 5° C. The mixture was stirred for 40 minutes for preparation of diazo salt of p-aminobenzenesulfonic acid.

The solution of diazo salt of p-aminobenzenesulfonic acid was added dropwise to a mixture of 3-Chloro-2,6-difluorophenol (44 g), water (516 g), 5N—NaOH (70 mL) and Na$_2$CO$_3$ (28 g) below 5° C. After the reaction was completed, pH was adjusted to 5.0 by adding 12N—HCl. Then ammonium formate (108 g) and Zn powder (65 g) was added the reaction mixture slowly. After the reaction was completed, the filtration was extracted with EA (500 mL×2) and the combined organic phase was washed with water and dried with anhydrous sodium sulfate. The solvent was removed and DCM (120 mL) was added to the slurry. After stirring, the appeared precipitate was filtered, washed and dried to give SM2-01 (40 g), yield: 83%.

$^1$H-NMR for the SM2-01 hydrochloride (400 MHz, CD$_3$OD) δ:7.30/7.273 (m, 1H);

$^{13}$C-NMR for the SM2-01 hydrochloride (100 MHz, CD$_3$OD) δ: 153.51 (m), 151.95 (m), 137.45 (m), 120.98 (m), 113.68 (m), 109.00 (m);

$^{19}$F-NMR for the SM2-01 hydrochloride (377 MHz, CD$_3$OD) δ: −132.36, −132.40, −133.09, −133.13.

ESI-MS (M+H$^+$): m/z calculated: 180.0, founded: 180.1.

Method 2 for Synthesis of Compound SM2-01

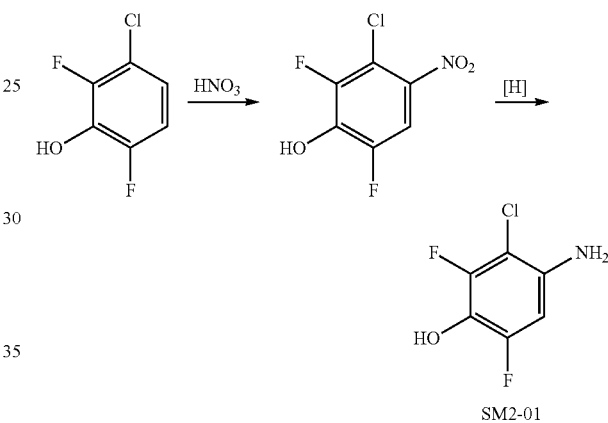

Concentrated nitric acid (300 g) was added dropwise to a mixture of 3-Chloro-2,6-difluorophenol (500 g) and DCM (2 L) below 10° C. After the reaction was completed, the mixture was extracted with DCM (1 L×2) and the combined organic phase was washed with water. and concentrated. The solvent was removed to give 3-chloro-2,6-difluoro-4-nitrophenol (675 g).

The powder of Fe (500 g) was added to a mixture of 3-chloro-2,6-difluoro-4-nitrophenol (675 g) and H$_2$O (5.0 L). Then 12N—HCl (100 mL) was added dropwise to the mixture between 85° C. and 95° C. After the completion of adding 12N—HCl, The powder of Fe (500 g) was added. After the reaction was completed, the filtration was extracted with EA (2 L×2) and the combined organic phase was washed with water and dried with anhydrous sodium sulfate. The solvent was removed and DCM (600 mL) was added to the slurry. After stirring, the appeared precipitate was filtered, washed and dried to give SM2-01 (393 g), yield: 72%.

NMR and LC-MS analyses were confirmed that SM2-01 could be reliably synthesized by two methods, the key trihalogenated aminophenol compound in the innovation of the present invention.

Example 2

Synthesis of Compound IIIb-01

The synthesis was carried out according to the method shown in General Synthesis method 1.

Step 1:

A mixture of SM1b-01 (2.52 g, 10 mmol), SM2-01 (2.34 g, 13 mmol), potassium t-butoxide (1.46 g, 13 mmol) and DMSO (20 mL) was stirred under nitrogen at 85° C. After the reaction was completed, the mixture was dropped into water (100 mL). The appeared precipitate was filtered and dried to give RM1-23 (3.28 g), yield: 83%.

Step 2:

To a mixture of RM1-23 (3.95 g, 10 mmol), DMF (20 mL) and pyridine (30 mmol) in a 100 mL flask, phenyl chloroformate (30 mmol) was added dropwise below 10° C. After the reaction was completed, the mixture was dropped into water (100 mL). The appeared precipitate was filtered and purified by column chromatography to obtain RM2-23 (3.45 g), yield: 67%.

Step 3:

A mixture of RM2-23 (5.15 g, 10 mmol), acetonitrile (50 mL) and SM3-01 (30 mmol) was stirred at 60° C. After the reaction was completed, the appeared precipitate was filtered and dried to obtain RM3-01 (2.91 g), yield: 61%.

Step 4:

A mixture of RM3-01 (4.78 g, 10 mmol), THF (10 mL), MeOH (10 mL) and sodium hydroxide (30 mmol) was stirred at 40° C. After the reaction was completed, pH was adjusted to about 6 by 3N—HCl. The appeared precipitate was filtered, washed and dried. RM4-01 (3.94 g) was obtained, yield: 85%.

Step 5:

To a mixture of RM4-01 (464 mg, 1.0 mmol), DMF (5 mL), HATU (1.3 mmol) and SM4-01 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-01 (386 mg), yield: 81%.

$^1$H-NMR for the compound IIIb-01 (DMSO, 400 MHz, +1.0 eq methane sulfonic acid) δ: 9.06-9.05 (d, 1H), 8.68 (s, 1H), 8.54 (m, 1H), 8.43 (s, 1H), 8.36-8.32 (dd, 1H), 7.69 (s, 1H), 7.48 (d, 1H), 7.33-7.31 (d, 1H), 4.09 (s, 3H), 2.85-2.84 (d, 3H), 2.61 (m, 1H), 2.39 (s, 3H), 0.70-0.69 (m, 2H), 0.46 (m, 2H). ESI-MS (M+H$^+$): m/z calculated: 477.1, founded: 477.2.

Example 3

Synthesis of Compound IIIb-02

The synthesis was carried out according to the method shown in General Synthesis method 1.

Step 1:

A mixture of SM1b-01 (2.52 g, 10 mmol), SM2-02 (2.12 g, 13 mmol), potassium t-butoxide (1.46 g, 13 mmol) and DMSO (20 mL) was stirred under nitrogen at 85° C. After the reaction was completed, the mixture was dropped into water. The appeared precipitate was filtered and dried to give RM1-24 (2.95 g), yield: 78%.

Step 2:

To a mixture of RM1-24 (3.78 g, 10 mmol), DMF (20 mL) and pyridine (30 mmol) in a 100 mL flask, phenyl chloroformate (30 mmol) was added dropwise below 10° C. After the reaction was completed, the mixture was dropped into water (100 mL). The appeared precipitate was filtered and purified by column chromatography to obtain RM2-24 (3.64 g), yield: 73%.

Step 3:

A mixture of RM2-24 (4.98 g, 10 mmol), acetonitrile (50 mL) and SM3-01 (30 mmol) was stirred at 60° C. After the reaction was completed, the appeared precipitate was filtered and dried to obtain RM3-02 (2.63 g), yield: 57%.

Step 4:

A mixture of RM3-02 (4.61 g, 10 mmol), THF (10 mL), MeOH (10 mL) and sodium hydroxide (30 mmol) was stirred at 40° C. After the reaction was completed, pH was adjusted to 6 by 3N—HCl. The appeared precipitate was filtered, washed and dried. RM4-02 (3.53 g) was obtained, yield: 79%.

Step 5:

To a mixture of RM4-02 (447 mg, 1.0 mmol), DMF (5 mL), HATU (1.3 mmol) and SM4-01 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-02 (308 mg), yield: 67%.

ESI-MS (M+H$^+$): m/z calculated: 461.1, founded: 461.2.

Example 4

Synthesis of Compound IIIb-03

The synthesis was carried out according to the method shown in General Synthesis method 1.

The synthesis method for the preparation of compound IIIb-03 is the same as in Example 2, where in the fifth step reaction: To a mixture of RM4-01 (464 mg, 1.0 mmol), DMF (5 mL), HATU (1.3 mmol) and SM4-02 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-03 (329 mg), yield: 67%.

ESI-MS (M+H$^+$): m/z calculated: 491.1, founded: 491.1.

Example 5

Synthesis of Compound IIIb-04

The synthesis was carried out according to the method shown in General Synthesis method 1.

The synthesis method for the preparation of compound IIIb-04 is the same as in Example 2, where in the fifth step reaction: To a mixture of RM4-01 (464 mg, 1.0 mmol), DMF (5 mL), HATU (1.3 mmol) and SM4-03 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-04 (345 mg), yield: 68%.

ESI-MS (M+H$^+$): m/z calculated: 505.1, founded: 505.0.

Example 6

Synthesis of Compound IIIb-05

The synthesis was carried out according to the method shown in General Synthesis method.

The synthesis method for the preparation of compound IIIb-05 is the same as in Example 2, where in the fifth step reaction: To a mixture of RM4-01 (464 mg, 1.0 mmol), DMF (5 mL), HATU (1.3 mmol) and SM4-11 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-05 (401 mg), yield: 77%.

$^1$H-NMR for the compound IIIb-05 (DMSO, 400 MHz, +1.0 eq methanesulfonic acid) δ: 8.97 (m, 1H), 8.78-8.75 (t, 1H), 8.63 (s, 1H), 8.41 (s, 1H), 8.36-8.32 (dd, 1H), 7.63 (s, 1H), 7.46-7.45 (d, 1H), 7.19 (m, 1H), 4.65-4.63 (t, 1H), 4.54-4.51 (t, 1H), 4.07 (s, 3H), 3.68-3.64 (t, 1H), 3.62-3.58 (t, 1H), 2.61 (m, 1H), 2.33 (m, 3H), 0.72-0.67 (m, 2H), 0.45 (m, 2H).
$^{19}$F-NMR for the compound IIIb-05 (DMSO, 377 MHz, +1.0 eq methanesulfonic acid) δ: −126.67 (s), −127.72 (s).
ESI-MS (M+H$^+$): m/z calculated: 521.1, founded: 521.2.

Example 7

Synthesis of Compound IIIb-06
Synthesis of Compound IIIb-06
The synthesis was carried out according to the method shown in General Synthesis method.
The synthesis method for the preparation of compound IIIb-06 is the same as in Example 2, where in the fifth step reaction: To a mixture of RM4-01 (464 mg, 1.0 mmol), DMF (5 mL), HATU (1.3 mmol) and SM4-04 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-06 (407 mg), yield: 80%.
ESI-MS (M+H$^+$): m/z calculated: 509.1, founded: 509.1.

Example 8

Synthesis of Compound IIIb-07
The synthesis was carried out according to the method shown in General Synthesis method.
The synthesis method for the preparation of compound IIIb-07 is the same as in Example 3, where in the fifth step reaction: To a mixture of RM4-02 (447 mg, 1.0 mmol), DMF (5 mL), HATU (1.3 mmol) and SM4-05 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-07 (424 mg), yield: 83%.
$^1$H-NMR for the compound IIIb-07 (DMSO, 400 MHz, +1.0 eq methanesulfonic acid) δ: 9.12-9.10 (d, 1H), 8.98-8.95 (t, 1H), 8.85 (s, 1H), 8.67 (s, 1H), 8.25-8.22 (m, 1H), 7.72 (s, 1H), 7.39-7.37 (d, 1H), 7.03 (m, 1H), 6.33-6.05 (m, 1H), 4.09 (s, 3H), 3.79-3.70 (m, 2H), 2.61 (m, 1H), 2.39 (s, 3H), 0.68-0.65 (m, 2H), 0.46-0.42 (m, 2H).
$^{19}$F-NMR for the compound IIIb-07 (DMSO, 377 MHz, +1.0 eq methanesulfonic acid) δ: −121.56 (s), −132.15 (s), −132.18 (s), −150.58 (s), −150.64 (s).
ESI-MS (M+H$^+$): m/z calculated: 511.1, founded: 511.1.

Example 9

Synthesis of Compound IIIb-08
The synthesis was carried out according to the method shown in General Synthesis method.
The synthesis method for the preparation of compound IIIb-08 is the same as in Example 2, where in the fifth step reaction: to a mixture of RM4-01 (464 mg, 1.0 mmol), DMF (5 mL), HATU (1.3 mmol) and SM4-05 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-08 (453 mg), yield: 86%.
$^1$H-NMR for the compound IIIb-08 (DMSO, 400 MHz) δ: 8.82-8.79 (t, J=6.0 Hz, 1H), 8.72-8.71 (d, J=5.3 Hz, 1H), 8.60 (s, 1H), 8.36 (s, 1H), 8.32-8.28 (dd, 1H), 7.59 (s, 1H), 7.43-7.42 (d, 1H), 6.78-6.77 (d, J=5.3 Hz, 1H), 6.33-6.05 (tt, 1H), 4.04 (s, 3H), 3.79-3.70 (m, 2H), 2.61 (m, 1H), 0.70-0.67 (m, 2H), 0.45 (m, 2H).
$^{19}$F-NMR for the compound IIIb-08 (DMSO, 377 MHz) δ: −121.62 (s), −127.11 (m), −127.88 (s).
ESI-MS (M+H$^+$): m/z calculated: 527.1, founded: 527.1.

Example 10

Synthesis of Compound IIIb-09
The synthesis was carried out according to the method shown in General Synthesis method.
The synthesis method for the preparation of compound IIIb-09 is the same as in Example 2, where in the fifth step reaction: to a mixture of RM4-01 (464 mg, 1.0 mmol), DMF (5 mL), HATU (1.3 mmol) and SM4-06 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-09 (441 mg), yield: 81%.
$^1$H-NMR for the compound IIIb-09 (DMSO, 400 MHz) δ: 9.04-9.01 (t, 1H), 8.73-8.72 (d, J=5.2 Hz, 1H), 8.53 (s, 1H), 8.35 (s, 1H), 8.32-8.28 (dd, 1H), 7.60 (s, 1H), 7.43 (d, 1H), 6.79-6.77 (d, J=5.2 Hz, 1H), 4.18-4.13 (m, 2H), 4.03 (s, 3H), 2.61 (m, 1H), 0.70-0.68 (m, 2H), 0.45 (m, 2H).
$^{19}$F-NMR for the compound IIIb-09 (DMSO, 377 MHz) δ: −70.29 (s), −127.07/−127.08 (d), −127.84 (s).
ESI-MS (M+H$^+$): m/z calculated: 545.1, founded: 545.1.

Example 11

Synthesis of Compound IIIb-10
The synthesis was carried out according to the method shown in General Synthesis method.
The synthesis method for the preparation of compound IIIb-10 is the same as in Example 2, where in the fifth step reaction: To a mixture of RM4-01 (464 mg, 1.0 mmol), DMF (5 mL), HATU (1.3 mmol) and SM4-07 (1.5 mmol) mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-10 (368 mg), yield: 69%.
ESI-MS (M+H$^+$): m/z calculated: 534.2, founded: 534.1.

Example 12

Synthesis of Compound IIIb-11
The synthesis was carried out according to the method shown in General Synthesis method. The synthesis method for the preparation of compound IIIb-11 is the same as in Example 3, where in the fifth step reaction: To a mixture of RM4-02 (447 mg, 1.0 mmol), DMF (5 mL), HATU (1.3 mmol) and SM4-08 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-11 (424 mg), yield: 87%.
ESI-MS (M+H$^+$): m/z calculated: 487.2, founded: 487.2.

Example 13

Synthesis of Compound IIIb-12

The synthesis was carried out according to the method shown in General Synthesis method. The synthesis method for the preparation of compound IIIb-12 is the same as in Example 2, where in the fifth step reaction: To a mixture of RM4-01 (464 mg, 1.0 mmol), DMF (5 mL), HATU (1.3 mmol) and SM4-08 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-12 (392 mg), yield: 78%.

ESI-MS (M+H$^+$): m/z calculated: 503.1, founded: 503.1.

Example 14

Synthesis of Compound IIIb-13

The synthesis was carried out according to the method shown in General Synthesis method. The synthesis method for the preparation of compound IIIb-13 is the same as in Example 2, where in the fifth step reaction: To a mixture of RM4-01 (464 mg, 1.0 mmol), DMF (5 mL), HATU (1.3 mmol) and SM4-09 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-13 (402 mg), yield: 74%.

ESI-MS (M+H$^+$): m/z calculated: 543.2, founded: 543.0.

Example 15

Synthesis of Compound IIIb-14

The synthesis was carried out according to the method shown in General Synthesis method. The synthesis method for the preparation of compound IIIb-14 is the same as in Example 2, where in the fifth step reaction: To a mixture of RM4-01 (464 mg, 1.0 mmol), DMF (5 mL), HATU (1.3 mmol) and SM4-10 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-14 (317 mg), yield: 63%.

ESI-MS (M+H$^+$): m/z calculated: 503.1, founded: 503.0.

Example 16

Synthesis of Compound IIIb-15

The synthesis was carried out according to the method shown in General Synthesis method. The synthesis method for the preparation of compound IIIb-15 is the same as in Example 3, where in the fifth step reaction: To a mixture of RM4-02 (447 mg, 1.0 mmol), DMF (5 mL), HATU (1.3 mmol) and SM4-12 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-15 (236 mg), yield: 48%.

ESI-MS (M+H$^+$): m/z calculated: 491.1, founded: 491.3.

Example 17

Synthesis of Compound IIIb-16

The synthesis was carried out according to the method shown in General Synthesis method. The synthesis method for the preparation of compound IIIb-16 is the same as in Example 2, where in the fifth step reaction: To a mixture of RM4-01 (464 mg, 1.0 mmol), DMF (5 mL), HATU (1.3 mmol) and SM4-12 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-16 (294 mg), yield: 58%.

ESI-MS (M+H$^+$): m/z calculated: 507.1, founded: 507.1.

Example 18

Synthesis of Compound IIIb-17

The synthesis was carried out according to the method shown in General Synthesis method. The synthesis method for the preparation of compound IIIb-17 is the same as in Example 2, where in the fifth step reaction: To a mixture of RM4-01 (464 mg, 1.0 mmol), DMF (5 mL), HATU (1.3 mmol) and SM4-13 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-17 (245 mg), yield: 47%.

ESI-MS (M+H$^+$): m/z calculated: 521.1, founded: 521.2.

Example 19

Synthesis of Compound IIIb-18

The synthesis was carried out according to the method shown in General Synthesis method. The synthesis method for the preparation of compound IIIb-18 is the same as in Example 2, where in the fifth step reaction: To a mixture of RM4-01 (464 mg, 1.0 mmol), DMF (5 mL), HATU (1.3 mmol) and SM4-14 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-18 (422 mg), yield: 81%.

$^1$H-NMR for the compound IIIb-18 (DMSO, 400 MHz) δ: 8.71-8.69 (d, J=5.2 Hz, 1H), 8.57 (s, 1H), 8.35 (s, 1H), 8.32-8.28 (dd, 1H), 8.26-8.24 (d, 1H), 7.56 (s, 1H), 7.43-7.42 (d, 1H), 6.76-6.75 (d, J=5.2 Hz, 1H), 4.85 (m, 1H), 4.03 (m, 4H), 3.45 (m, 1H), 3.42 (m, 1H), 2.60 (m, 1H), 1.18-1.16 (d, J=6.6 Hz, 3H), 0.70 (m, 2H), 0.45 (m, 2H).

$^{19}$F-NMR for the compound IIIb-18 (DMSO, 377 MHz) δ: −127.09/127.10 (d), −127.84 (s).

ESI-MS (M+H$^+$): m/z calculated: 521.1, founded: 521.2.

Example 20

Synthesis of Compound IIIb-19

The synthesis was carried out according to the method shown in General Synthesis method. The synthesis method for preparing compound IIIb-19 is the same as in Example 2, where in the fifth step reaction: To a mixture of RM4-01 (464 mg, 1.0 mmol), DMF (5 mL), HATU (1.3 mmol) and SM4-15 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-19 (305 mg), yield: 57%.

ESI-MS (M+H$^+$): m/z calculated: 535.1, founded: 535.2.

Example 21

Synthesis of Compound IIIb-20

The synthesis was carried out according to the method shown in General Synthesis method. The synthesis method for the preparation of compound IIIb-20 is the same as in Example 2, where in the fifth step reaction: To a mixture of RM4-01 (464 mg, 1.0 mmol), DMF (5 mL), HATU (1.3 mmol) and SM4-16 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-20 (242 mg), yield: 45%.

ESI-MS (M+H$^+$): m/z calculated: 537.1, founded: 537.2.

Example 22

Synthesis of Compound IIIb-21

The synthesis was carried out according to the method shown in General Synthesis method. The synthesis method for the preparation of compound IIIb-21 is the same as in Example 2, where in the fifth step reaction: To a mixture of RM4-01 (464 mg, 1.0 mmol), DMF (5 mL), HATU (1.3 mmol) and SM4-17 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-21 (295 mg), yield: 55%.

$^1$H-NMR for the compound IIIb-21 (DMSO, 400 MHz) δ: 8.72-8.70 (d, J=5.2 Hz, 1H), 8.69 (s, 1H), 8.51 (t, 1H), 8.35 (s, 1H), 8.32-8.28 (dd, 1H), 7.59 (s, 1H), 7.46 (d, 1H), 6.77 (d, J=5.2 Hz, 1H), 4.95 (d, 1H), 4.68 (t, 1H), 4.05 (s, 3H), 3.67-3.66 (m, 1H), 3.48 (m, 1H), 3.42-3.37 (m, 2H), 3.31-3.28 (m, 2H), 2.61 (m, 1H), 0.70-0.68 (m, 2H), 0.45 (m, 2H).

$^{19}$F-NMR for the compound IIIb-21 (DMSO, 377 MHz) δ: -127.10/127.11 (d), -127.86 (s).

ESI-MS (M+H$^+$): m/z calculated: 537.1, founded: 537.2.

Example 23

Synthesis of Compound IIIb-22

The synthesis was carried out according to the method shown in General Synthesis method. The synthesis method for the preparation of compound IIIb-22 is the same as in Example 2, where in the fifth step reaction: To a mixture of RM4-01 (464 mg, 1.0 mmol), DMF (5 mL), HATU (1.3 mmol) and SM4-18 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-22 (258 mg), yield: 48%.

$^1$H-NMR for the compound IIIb-22 (DMSO, 400 MHz) δ: 8.72-8.71 (d, J=5.3 Hz, 1H), 8.69 (s, 1H), 8.51 (t, 1H), 8.36 (s, 1H), 8.32-8.28 (dd, 1H), 7.59 (s, 1H), 7.46 (d, 1H), 6.77-6.76 (d, J=5.3 Hz, 1H), 4.95 (d, 1H), 4.68 (t, 1H), 4.05 (s, 3H), 3.67-3.66 (m, 1H), 3.48 (m, 1H), 3.42-3.37 (m, 2H), 3.31-3.28 (m, 2H), 2.61 (m, 1H), 0.70-0.68 (m, 2H), 0.45 (m, 2H).

$^{19}$F-NMR for the compound IIIb-22 (DMSO, 377 MHz) δ: -127.10/127.11 (d), -127.86 (s).

ESI-MS (M+H$^+$): m/z calculated: 537.1, founded: 537.2.

Example 24

Synthesis of Compound IIIb-23

The synthesis was carried out according to the method shown in General Synthesis method. The synthesis method for the preparation of compound IIIb-23 is the same as in Example 2, where in the fifth step reaction: To a mixture of RM4-01 (464 mg, 1.0 mmol), DMF (5 mL), HATU (1.3 mmol) and SM4-19 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-23 (219 mg), yield: 41%.

ESI-MS (M+H$^+$): m/z calculated: 533.1, founded: 533.2.

Example 25

Synthesis of Compound IIIb-24

The synthesis was carried out according to the method shown in General Synthesis method. The synthesis method for the preparation of compound IIIb-24 is the same as in Example 2, where in the fifth step reaction: To a mixture of RM4-01 (464 mg, 1.0 mmol), DMF (5 mL), HATU (1.3 mmol) and SM4-20 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-24 (296 mg), yield: 57%.

ESI-MS (M+H$^+$): m/z calculated: 519.1, founded: 519.2.

Example 26

Synthesis of Compound IIIb-25

The synthesis was carried out according to the method shown in General Synthesis method. The synthesis method for the preparation of compound IIIb-25 is the same as in Example 2, where in the fifth step reaction: To a mixture of RM4-01 (464 mg, 1.0 mmol), DMF (5 mL), HATU (1.3 mmol) and SM4-21 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-25 (277 mg), yield: 52%.

ESI-MS (M+H$^+$): m/z calculated: 533.1, founded: 533.2.

Example 27

Synthesis of Compound IIIb-26

The synthesis was carried out according to the method shown in General Synthesis method. The synthesis method for the preparation of compound IIIb-26 is the same as in Example 2, where in the fifth step reaction: To a mixture of RM4-01 (464 mg, 1.0 mmol), DMF (5 mL), HATU (1.3 mmol) and SM4-22 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-26 (314 mg), yield: 59%.

ESI-MS (M+H$^+$): m/z calculated: 533.1, founded: 533.0.

95

Example 28

Synthesis of Compound IIIb-27

The synthesis was carried out according to the method shown in General Synthesis method. Preparation of compound IIIb-27 was synthesized in the same way as in Example 2, where in the fifth step reaction: To a mixture of RM4-01 (464 mg, 1.0 mmol), DMF (5 mL), HATU (1.3 mmol) and SM4-23 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-27 (300 mg), yield: 55%.

ESI-MS (M+H$^+$): m/z calculated: 546.2, founded: 546.0.

Example 29

Synthesis of Compound IIIb-28

The synthesis was carried out according to the method shown in General Synthesis method 1. Preparation of compound IIIb-28 was synthesized in the same way as in Example 2, where in the fifth step reaction: To a mixture of RM4-01 (464 mg, 1.0 mmol), DMF (5 mL), HATU (1.3 mmol) and SM4-24 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-28 (465 mg), yield: 83%.

ESI-MS (M+H$^+$): m/z calculated: 560.2, founded: 560.0.

Example 30

Synthesis of Compound IIIb-29

The synthesis was carried out according to the method shown in General Synthesis method.

Step 1:

A mixture of SM1b-12 (2.19 g, 10 mmol), SM2-01 (2.34 g, 13 mmol), potassium t-butoxide (1.46 g, 13 mmol) and DMSO (20 mL) was stirred under nitrogen at 85° C. After the reaction was completed, the mixture was dropped into water (100 mL). The appeared precipitate was filtered and dried to give RM1-25 (2.10 g), yield: 58%.

Step 2:

To a mixture of RM1-25 (3.62 g, 10 mmol), DMF (20 mL) and pyridine (30 mmol) in a 100 mL flask, phenyl chloroformate (30 mmol) was added dropwise below 10° C. After the reaction was completed, the mixture was dropped into water (100 mL). The appeared precipitate was filtered and purified by column chromatography to obtain RM2-25 (4.10 g), yield: 85%.

Step 3:

A mixture of RM2-25 (482 mg, 1 mmol), acetonitrile (50 mL) and SM3-01 (3 mmol) was stirred at 60° C. After the reaction was completed, the appeared precipitate was filtered, washed and purified by column chromatography to obtain IIIb-29 (280 mg), yield: 63%.

ESI-MS (M+H$^+$): m/z calculated: 445.1, founded: 444.8.

Example 31

Synthesis of Compound IIIb-30

The synthesis was carried out according to the method shown in General Synthesis method.

96

Step 1:

A mixture of SM1b-12 (2.19 g, 10 mmol), SM2-11 (2.49 g, 13 mmol), potassium t-butoxide (1.46 g, 13 mmol) and DMSO (20 mL) was stirred under nitrogen at 85° C. After the reaction was completed, the mixture was dropped into water (100 mL). The appeared precipitate was filtered and dried to give RM1-26 (2.43 g), yield: 65%.

Step 2:

To a mixture of RM1-26 (3.74 g, 10 mmol), DMF (20 mL) and pyridine (30 mmol) in a 100 mL flask, phenyl chloroformate (30 mmol) was added dropwise below 10° C. After the reaction was completed, the mixture was dropped into water (100 mL). The appeared precipitate was filtered and purified by column chromatography to obtain RM2-26 (3.95 g), yield: 80%.

Step 3:

A mixture of RM2-26 (494 mg, 1 mmol), acetonitrile (10 mL) and SM3-01 (3 mmol) was stirred at 60° C. After the reaction was completed, the appeared precipitate was filtered, washed and purified by column chromatography to obtain IIIb-30 (274 mg), yield: 60%.

ESI-MS (M+H$^+$): m/z calculated: 457.1, founded: 457.0.

Example 32

Synthesis of Compound IIIb-31

The synthesis was carried out according to the method shown in General Synthesis method.

The synthesis method for the preparation of compound IIIb-31 is the same as in Example 2, where in the fifth step reaction: To a mixture of RM4-01 (464 mg, 1.0 mmol), DMF (5 mL), HATU (1.3 mmol) and SM4-25 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to abtain the solid (330 mg).

A mixture of the solid (330 mg, 0.5 mmol), THF (0.5 mL), MeOH (0.5 mL), H$_2$O (0.5 mL) and NaOH (80 mg) was stirred at 40° C. After the reaction was completed, pH was adjusted to 6 by 3N—HCl. The appeared precipitate was filtered, washed and dried to obtain IIIb-31 (290 mg), yield: 53%.

ESI-MS (M+H$^+$): m/z calculated: 547.1, founded: 547.2.

Example 33

Synthesis of Compound IIIb-32

The synthesis was carried out according to the method shown in General Synthesis method.

Preparation of compound IIIb-32 was synthesized in the same way as in Example 2, where in the fifth step reaction: To a mixture of RM4-01 (464 mg, 1.0 mmol), DMF (5 mL), HATU (1.3 mmol) and SM4-26 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-32 (259 mg), yield: 48%.

ESI-MS (M+H$^+$): m/z calculated: 539.1, founded: 538.9.

Example 34

Synthesis of Compound IIIb-33

Preparation of compound IIIb-33 was synthesized in the same way as the first four steps of Example 2.

Step 5:

To a mixture of RM4-01 (478 mg, 1.0 mmol), DMF (5 mL) and CDI (1.5 mmol) in a 50 mL flask, DIEA (3.0 mmol) was added dropwise at 20° C. The mixture was stirred for one hour. Additionally, SM4-27 (3.0 mmol) was added and stirred. After the reaction was completed, water (20 mL) was added to the reaction mixture. Then the precipitated deposit was filtered, washed and purified by column chromatography to abtain IIIb-33 (151 mg), yield: 28%.

ESI-MS (M+H$^+$): m/z calculated: 541.1, founded: 540.9.

Example 35

Synthesis of Compound IIIb-34

Preparation of compound IIIb-34 was synthesized in the same way as the first four steps of Example 2.

Step 5:

To a mixture of RM4-01 (478 mg, 1.0 mmol), DMF (5 mL) and CDI (1.5 mmol) in a 50 mL flask, DIEA (3.0 mmol) was added dropwise at 20° C. The mixture was stirred for one hour. Additionally, SM4-28 (3.0 mmol) was added and stirred. After the reaction was completed, water (20 mL) was added to the reaction mixture. Then the precipitated deposit was filtered, washed and purified by column chromatography to obtain IIIb-34 (130 mg), yield: 23%.

ESI-MS (M+H$^+$): m/z calculated: 567.1, founded: 567.0.

Example 36

Synthesis of Compound IIIb-35

The synthesis was carried out according to the method shown in General Synthesis method. Preparation of compound IIIb-35 was synthesized in the same way as in Example 2, where in the fifth step reaction: To a mixture of RM4-01 (464 mg, 1.0 mmol), DMF (5 mL), HATU (1.3 mmol) and SM4-29 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-35 (409 mg), yield: 73%.

ESI-MS (M+H$^+$): m/z calculated: 560.1, founded: 559.8.

Example 37

Synthesis of Compound IIIb-36

The synthesis was carried out according to the method shown in General Synthesis method. Preparation of compound IIIb-36 was synthesized in the same way as in Example 2, where in the fifth step reaction: To a mixture of RM4-01 (464 mg, 1.0 mmol), DMF (5 mL), HATU (1.3 mmol) and SM4-30 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-36 (387 mg), yield: 69%.

ESI-MS (M+H$^+$): m/z calculated: 560.1, founded: 559.8.

Example 38

Synthesis of Compound IIIb-37

The synthesis was carried out according to the method shown in General Synthesis method. Preparation of compound IIIb-37 was synthesized in the same way as in Example 2, where in the fifth step reaction: To a mixture of RM4-01 (464 mg, 1.0 mmol), DMF (5 mL), HATU (1.3 mmol) and SM4-31 (1.5 mmol) in a 100 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-37 (178 mg), yield: 31%.

ESI-MS (M+H$^+$): m/z calculated: 573.1, founded: 573.0.

Example 39

Synthesis of Compound IIIb-38

The synthesis was carried out according to the method shown in General Synthesis method. Preparation of compound IIIb-38 was synthesized in the same way as in Example 2, where in the fifth step reaction: To a mixture of RM4-01 (464 mg, 1.0 mmol), DMF (5 mL), HATU (1.3 mmol) and SM4-32 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-37 (167 mg), yield: 29%.

ESI-MS (M+H$^+$): m/z calculated: 575.1, founded: 575.0.

Example 40

Synthesis of Compound IIIb-39

The synthesis was carried out according to the method shown in General Synthesis method. Preparation of compound IIIb-39 was synthesized in the same way as in Example 2, where in the fifth step reaction: To a mixture of RM4-01 (464 mg, 1.0 mmol), DMF (5 mL), HATU (1.3 mmol) and SM4-33 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-39 (408 mg), yield: 73%.

ESI-MS (M+H$^+$): m/z calculated: 559.1, founded: 558.9.

Example 41

Synthesis of Compound IIIb-40

The synthesis was carried out according to the method shown in General Synthesis method. Preparation of compound IIIb-40 was synthesized in the same way as in Example 2, where in the fifth step reaction: To a mixture of RM4-01 (464 mg, 1.0 mmol), DMF (5 mL), HATU (1.3 mmol) and SM4-34 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-40 (400 mg), yield: 70%.

ESI-MS (M+H$^+$): m/z calculated: 573.1, founded: 572.9.

Example 42

Synthesis of Compound IIIb-41

The synthesis was carried out according to the method shown in General Synthesis method. Preparation of compound IIIb-41 was synthesized in the same way as in Example 2, where in the fifth step reaction: To a mixture of RM4-01 (464 mg, 1.0 mmol), DMF (5 mL), HATU (1.3 mmol) and SM4-35 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-41 (383 mg), yield: 67%.

ESI-MS (M+H$^+$): m/z calculated: 571.1, founded: 570.9.

Example 43

Synthesis of Compound IIIb-42

The synthesis was carried out according to the method shown in General Synthesis method. Preparation of compound IIIb-42 was synthesized in the same way as in Example 2, where in the fifth step reaction: To a mixture of RM4-01 (464 mg, 1.0 mmol), DMF (5 mL), HATU (1.3 mmol) and SM4-36 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-42 (334 mg), yield: 58%.

ESI-MS (M+H$^+$): m/z calculated: 575.1, founded: 574.9.

Example 44

Synthesis of Compound IIIb-43

The synthesis was carried out according to the method shown in General Synthesis method. The synthesis method for preparing compound IIIb-43 is the same as in Example 2, where in the fifth step reaction: To a mixture of RM4-01 (464 mg, 1.0 mmol), DMF (5 mL), HATU (1.3 mmol) and SM4-37 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-43 (224 mg), yield: 39%.

ESI-MS (M+H$^+$): m/z calculated: 575.1, founded: 575.2.

Example 45

Synthesis of Compound IIIb-44

The synthesis was carried out according to the method shown in General Synthesis method. Preparation of compound IIIb-44 was synthesized in the same way as in Example 2, where in the fifth step reaction: To a mixture of RM4-01 (464 mg, 1.0 mmol), DMF (5 mL), HATU (1.3 mmol) and SM4-38 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-44 (132 mg), yield: 27%.

ESI-MS (M+H$^+$): m/z calculated: 488.1, founded: 487.8.

Example 46

Synthesis of Compound IIIb-45

The synthesis was carried out according to the method shown in General Synthesis method. Preparation of compound IIIb-45 was synthesized in the same way as in Example 2, where in the fifth step reaction: To a mixture of RM4-01 (464 mg, 1.0 mmol), DMF (5 mL), HATU (1.3 mmol) and SM4-39 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-45 (236 mg), yield: 47%.

ESI-MS (M+H$^+$): m/z calculated: 502.1, founded: 501.9

Example 47

Synthesis of Compound IIIb-46

The synthesis was carried out according to the method shown in General Synthesis method. Preparation of compound IIIb-46 was synthesized in the same way as in Example 2, where in the fifth step reaction: To a mixture of RM4-01 (464 mg, 1.0 mmol), DMF (5 mL), HATU (1.3 mmol) and SM4-40 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-46 (289 mg), yield: 56%.

ESI-MS (M+H$^+$): m/z calculated: 516.1, founded: 515.9.

Example 48

Synthesis of Compound IIIb-47

The synthesis was carried out according to the method shown in General Synthesis method. Preparation of compound IIIb-47 was synthesized in the same way as in Example 2, where in the fifth step reaction: To a mixture of RM4-01 (464 mg, 1.0 mmol), DMF (5 mL), HATU (1.3 mmol) and SM4-41 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-47 (419 mg), yield: 79%.

ESI-MS (M+H$^+$): m/z calculated: 530.1, founded: 529.9.

Example 49

Synthesis of Compound IIIb-48

The synthesis was carried out according to the method shown in General Synthesis method. Preparation of compound IIIb-48 was synthesized in the same way as in Example 2, where in the fifth step reaction: To a mixture of RM4-01 (464 mg, 1.0 mmol), DMF (5 mL), HATU (1.3 mmol) and SM4-42 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-48 (322 mg), yield: 61%.

ESI-MS (M+H$^+$): m/z calculated: 528.1, founded: 527.9.

Example 50

Synthesis of Compound IIIb-49

The synthesis was carried out according to the method shown in General Synthesis method. Preparation of compound IIIb-49 was synthesized in the same way as in Example 2, where in the fifth step reaction: To a mixture of RM4-01 (464 mg, 1.0 mmol), DMF (5 mL), HATU (1.3 mmol) and SM4-43 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-49 (396 mg), yield: 73%.

ESI-MS (M+H$^+$): m/z calculated: 542.1, founded: 541.9.

Example 51

Synthesis of Compound IIIb-50

The synthesis was carried out according to the method shown in General Synthesis method. Preparation of compound IIIb-50 was synthesized in the same way as in Example 2, where in the fifth step reaction: To a mixture of RM4-01 (464 mg, 1.0 mmol), DMF (5 mL), HATU (1.3 mmol) and SM4-44 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-50 (356 mg), yield: 69%.

$^1$H-NMR for the compound IIIb-50 (DMSO, 400 MHz) δ: 8.78 (t, 1H), 8.72 (d, J=5.2 Hz, 1H), 8.62 (s, 1H), 8.35 (s, 1H), 8.32 (d, 1H), 7.59 (s, 1H), 7.43 (m, 1H), 6.77-6.76 (d, J=5.2 Hz, 1H), 4.05 (s, 3H), 3.60 (q, 2H), 2.83 (t, 2H), 2.61 (m, 1H), 0.70 (m, 2H), 0.45 (m, 2H).

$^{19}$F-NMR for the compound IIIb-50 (DMSO, 377 MHz) δ: −127.11 (s), −127.86 (s).

ESI-MS (M+H$^+$): m/z calculated: 516.1, founded: 515.9.

Example 52

Synthesis of Compound IIIb-51

The synthesis method for the preparation of compound IIIb-51 is the same as the previous four steps of Example 2.

Step 5: To a mixture of RM4-01 (464 mg, 1.0 mmol), DMF (5 mL), HATU (1.3 mmol) and SM4-45 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain the solid intermediate (280 mg).

A mixture of the above solid intermediate (280 mg), MeOH (0.5 mL), H$_2$O (1.5 mL) and 12N—HCl (0.5 mL) was stirred at 30° C. After the reaction was completed, pH was adjusted to about 10 by 3N NaOH solution. The appeared precipitate was filtered, washed and dried to obtain IIIb-51 (172 mg), yield: 34%.

ESI-MS (M+H$^+$): m/z calculated: 506.1, founded: 505.9.

Example 53

Synthesis of Compound IIIb-52

Preparation of compound IIIb-52 was synthesized in the same way as in Example 2, where in the fifth step reaction:

To a mixture of RM4-01 (464 mg, 1.0 mmol), DMF (5 mL), HATU (1.3 mmol) and SM4-46 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-52 (228 mg), yield: 43%.

ESI-MS (M+H$^+$): m/z calculated: 529.1, founded: 528.8.

Example 54

Synthesis of Compound IIIb-53

Preparation of compound IIIb-52 was synthesized in the same way as in Example 2, where in the fifth step reaction:

To a mixture of RM4-01 (464 mg, 1.0 mmol), DMF (5 mL), HATU (1.3 mmol) and SM4-47 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-53 (337 mg), yield: 62%.

ESI-MS (M+H$^+$): m/z calculated: 543.1, founded: 543.0.

Example 55

Synthesis of Compound IIIb-54

Preparation of compound IIIb-52 was synthesized in the same way as in Example 2, where in the fifth step reaction:

To a mixture of RM4-01 (464 mg, 1.0 mmol), DMF (5 mL), HATU (1.3 mmol) and SM4-48 (1.5 mmol) in a 50 mL flask, DIEA (3.0 mmol) was added dropwise at 20° C. After the reaction was completed, water (20 mL) was added to the reaction mixture. Then the appeared precipitate was filtered, washed and purified by column chromatography to obtain IIIb-54 (358 mg), yield: 66%.

ESI-MS (M+H$^+$): m/z calculated: 543.1, founded: 543.0.

Example 56

Synthesis of Compound IIIb-55

The synthesis was carried out according to the General Synthesis method.

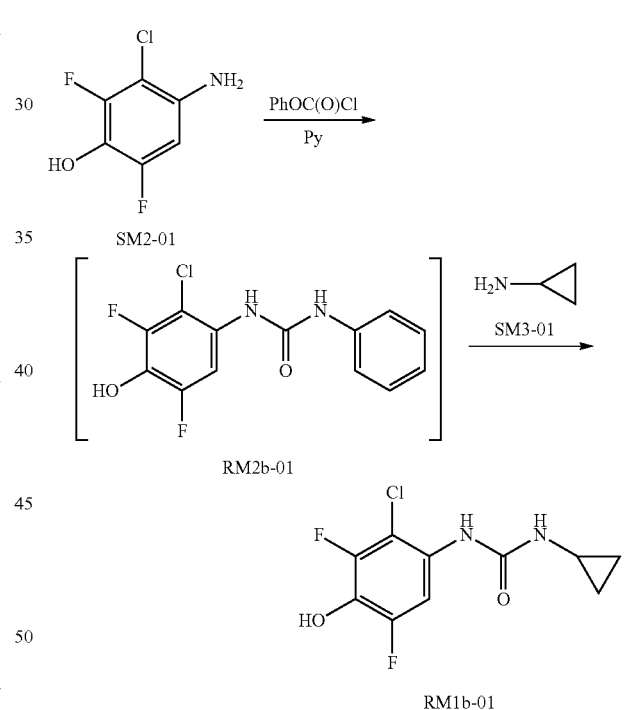

(1). Preparation of phenyl (2-chloro-3,5-difluoro-4-hydroxyphenyl)carbamate

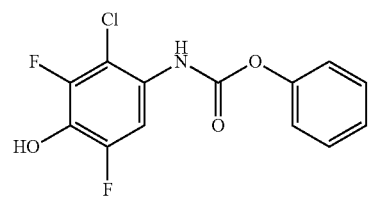

A mixture of SM2-01 (100 g, 0.56 mol), pyridine (58 g, 0.73 mol) and DMF (1 L) was s stirred in the ice bath. Phenyl chloroformate (96 g, 0.61 mol) was added dropwise below 10° C. After the reaction was completed, the reaction was to the next step directly.

$^1$H-NMR for RM2b-01, (DMSO, 400 MHz) δ: 10.71 (s, 1H), 9.78 (s, 1H), 7.44-7.36 (m, 3H), 7.27-7.19 (m, 3H). $^{19}$F-NMR Spectrum (DMSO, 377 MHz) δ: −131.38/−131.42 (d), −132.79/−132.81 (d).

(2). Preparation of 3-chloro-4-(3-cyclopropylureido)-2,6-difluorophenolate

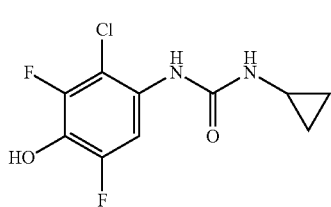 [SMILES: O=C(Nc1cc(F)c(O)c(F)c1Cl)NC1CC1]

RM1b-01

After dissolving phenyl (2-chloro-3,5-difluoro-4-hydroxyphenyl) carbamate in DMF (800 mL), cyclopropylamine (127 g, 2.24 mol) was added dropwise below 10° C., and the mixture was stirred at room temperature. After the reaction was completed, acetonitrile (2 L) was added and stirred. Then the appeared precipitate was filtered and washed with ethyl acetate (300 mL) to obtain cyclopropanaminium 3-chloro-4-(3-cyclopropylureido)-2,6-difluoro phenolate (143 g).

6N—HCl (80 mL) was added dropwise to a mixture of cyclopropanaminium 3-chloro-4-(3-cyclopropylureido)-2,6-difluorophenolate (143 g) and MeOH (700 mL). The mixture was stirred until fully soluble, and then water (3.0 L) was added. Then the appeared precipitate was filtered, washed with water (1000 mL) and dried to obtain RM1b-01 (117 g), yield: 80%.

$^1$H-NMR for the RM1b-01 (DMSO, 400 MHz) δ: 10.13 (s, 1H), 7.90 (s, 1H), 7.86-7.82 (dd, 1H), 7.11 (d, 1H), 2.56 (m, 1H), 0.67-0.62 (m, 2H), 0.43-0.39 (m, 2H). $^{13}$C-NMR for the RM1b-01 (100 MHz, DMSO) δ: 155.47 (s), 151.82 (m), 149.74 (m), 129.04 (m), 128.87-128.67 (m), 105.54 (m), 103.54 (m), 22.27 (s), 6.19 (s). $^{19}$F-NMR for the RM1b-01 (DMSO, 377 MHz) δ: −132.09 (m).

ESI-MS (M+H$^+$): m/z calculated: 263.0, founded: 263.1.

(3). Synthesis of Compound IIIb-55

A mixture of SM1b-02 (269 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-55 (312 mg), yield: 63%.

ESI-MS (M+H$^+$): m/z calculated: 495.1, founded: 494.9.

Example 57

Synthesis of Compound IIIb-56

The synthesis was carried out according to the General Synthesis method. Preparation of compound IIIb-56 was synthesized in the same way as in Example 56, where in the third reaction step as follow:

A mixture of SM1b-03 (287 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-56 (323 mg), yield: 60%.

$^1$H-NMR for the compound IIIb-56 (400 MHz, DMSO+ 1.0 eq methanesulfonic acid) δ: 8.95-8.94 (d, J=6.0 Hz, 1H), 8.66 (s, 1H), 8.44 (s, 1H), 8.30-8.27 (d, J=13.2 Hz, 1H), 7.90 (s, 1H), 7.80 (s, 1H), 7.76 (s, 1H), 7.55 (s, 1H), 7.17-7.16 (m, 1H), 6.68-6.41 (m, 1H), 4.68-4.61 (m, 2H), 2.58 (m, 1H), 2.33 (s, 3H), 0.64 (m, 2H), 0.41 (m, 2H).

$^{19}$F-NMR for the compound IIIb-56 (377 MHz, DMSO+ 1.0 eq methanesulfonic acid) δ: −125.60 (m), −125.75 (m), −126.62 (s), −127.65 (m).

ESI-MS (M+H$^+$): m/z calculated: 513.1, founded: 512.8.

Example 58

Synthesis of Compound IIIb-57

The synthesis was carried out according to the General Synthesis method. Preparation of compound IIIb-57 was synthesized in the same way as in Example 56, where in the third reaction step as follow:

A mixture of SM1b-04 (305 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-57 (276 mg), yield: 52%.

ESI-MS (M+H$^+$): m/z calculated: 531.1, founded: 530.8.

Example 59

Synthesis of Compound IIIb-58

The synthesis was carried out according to the General Synthesis method. Preparation of compound IIIb-58 was synthesized in the same way as in Example 56, where in the third reaction step as follow:

A mixture of SM1b-05 (262 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-58 (259 mg), yield: 53%.

ESI-MS (M+H$^+$): m/z calculated: 488.1, founded: 487.8.

Example 60

Synthesis of Compound IIIb-59

Preparation of compound IIIb-59 was synthesized in the same way as in Example 56, where in the third reaction step as follow:

A mixture of SM1b-06 (294 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-59 (354 mg), yield: 68%.

ESI-MS (M+H$^+$): m/z calculated: 520.1, founded: 519.9.

Example 61

Synthesis of Compound IIIb-60

Preparation of compound IIIb-60 was synthesized in the same way as in Example 56, where in the third reaction step as follow:

A mixture of SM1b-07 (267 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-60 (192 mg), yield: 38%.

$^1$H-NMR for the compound IIIb-60 (400 MHz, DMSO+1.0 eq methanesulfonic acid) δ: 9.00-8.99 (d, J=6.4 Hz, 1H), 8.81 (s, 1H), 8.38 (s, 1H), 8.32 (s, 1H), 7.96 (s, 1H), 7.94 (m, 1H), 7.90 (s, 1H), 7.70 (s, 1H), 7.43-7.42 (m, 1H), 7.25-7.23 (d, J=6.4 Hz, 1H), 4.34-4.32 (t, J=4.4 Hz, 2H), 3.86-3.84 (t, J=4.4 Hz, 2H), 2.57 (m, 1H), 2.34 (s, 3H), 0.64 (m, 2H), 0.40 (m, 2H).

$^{19}$F-NMR for the compound IIIb-60 (377 MHz, DMSO+1.0 eq methanesulfonic acid) δ: −126.54 (s), −127.58 (m)

ESI-MS (M+H$^+$): m/z calculated: 493.1, founded: 492.9.

Example 62

Synthesis of Compound IIIb-61

Preparation of compound IIIb-61 was synthesized in the same way as in Example 56, where in the third reaction step as follow:

A mixture of SM1b-08 (392 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give the compound (530 mg).

A mixture of the compound (530 mg), 12N—HCl (5 mL) in MeOH (3 mL) was stirred. After the reaction was completed, the mixture was dropped into water (10 mL) and pH was adjusted to 10 by adding 3N—NaOH solution. The appeared precipitate was filtered, washed and purified by column chromatography to give IIIb-61 (233 mg), yield: 45%.

ESI-MS (M+H$^+$): m/z calculated: 518.1, founded: 517.9.

Example 63

Synthesis of Compound IIIb-62

Preparation of compound IIIb-62 was synthesized in the same way as in Example 56, where in the third reaction step as follow:

A mixture of SM1b-09 (293 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-62 (305 mg), yield: 59%.

ESI-MS (M+H$^+$): m/z calculated: 519.1, founded: 518.9.

Example 64

Synthesis of Compound IIIb-63

Preparation of compound IIIb-63 was synthesized in the same way as in Example 56, where in the third reaction step as follow:

A mixture of SM1b-10 (293 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-63 (274 mg), yield: 53%.

ESI-MS (M+H$^+$): m/z calculated: 519.1, founded: 518.9.

Example 65

Synthesis of Compound IIIb-64

Preparation of compound IIIb-64 was synthesized in the same way as in Example 56, where in the third reaction step as follow:

A mixture of SM1b-11 (291 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-64 (331 mg), yield: 64%.

ESI-MS (M+H$^+$): m/z calculated: 517.1, founded: 516.9.

Example 66

Synthesis of Compound IIIb-65

Preparation of compound IIIb-65 was synthesized in the same way as in Example 56, where in the third reaction step as follow:

A mixture of SM1b-16 (291 mg, 1 mmol), RM1b-01 (342 mg, 1.3 mmol) potassium t-butoxide (146 mg, 1.3 mmol) and DMSO (3 mL) was stirred at 65° C. After the reaction was completed, the mixture was dropped into water (30 mL). The appeared precipitate was filtered, washed and purified by column chromatography to give IIIb-65 (286 mg), yield: 57%.

ESI-MS (M+H$^+$): m/z calculated: 502.1, founded: 501.9.

Example 67

Synthesis of Compound IIIb-08 (Synthesis Method 2)

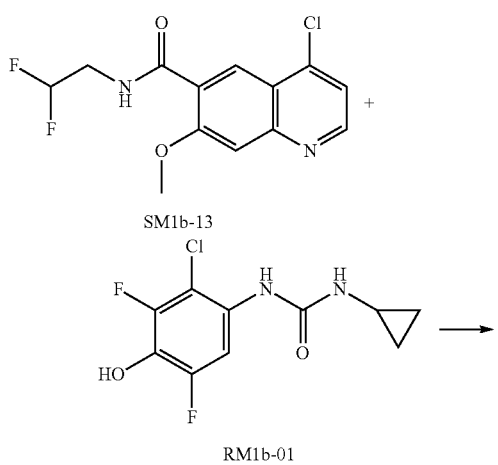

-continued

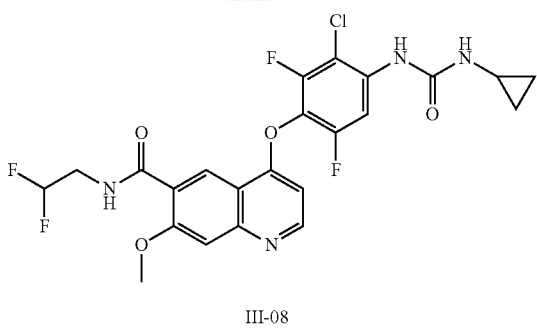

III-08

A mixture of SM1b-13 (10.0 g, 33 mmol), RM1b-01 (11.3 g, 43 mmol), potassium t-butoxide (4.8 g, 43 mmol) and DMSO (100 mL) was stirred at 65° C. After the reaction was completed, the mixture was dropped into ice water (100 mL). The appeared precipitate was filtered, washed and dried to give IIIb-08 (13.0 g), yield: 75%.

Example 68

Synthesis of Compound IIIb-50 (Synthesis Method 2)

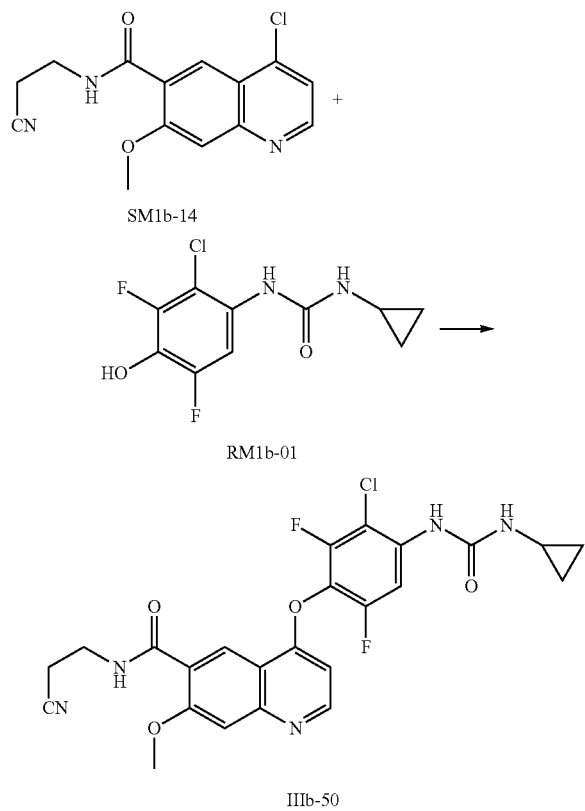

A mixture of SM1b-14 (10.0 g, 35 mmol), RM1b-01 (11.8 g, 45 mmol), potassium t-butoxide (4.8 g, 45 mmol) and DMSO (100 mL) was stirred at 65° C. After the reaction was completed, the mixture was dropped into ice water (100 mL). The appeared precipitate was filtered, washed and dried to give IIIb-50 (12.8 g), yield: 71%.

Example 69: The Pharmacodynamics Experiments of Tumor Inhibition In Vitro

The compound prepared by the present invention can be screened for its effect on target inhibition of several tumor cell lines including pancreatic cancer (BXPC3), lung cancer (A549), renal cancer (Caki-1), liver cancer (Hep3B 2.1-7), gastric cancer (SNU16), cervical cancer (Hela), prostatic cancer (PC-3), and leukemia cell line (K562) by the following preclinical in vitro inhibition assays. And further to screen better new anti-cancer drugs by measuring the inhibitory activity of more than five RTK targets such as VEGFR1, VEGFR 2, VEGFR 3, FGFR2, RET, etc. The efficacy of the new drug is then finally confirmed by clinical trials. Other methods are also apparent to those with general skills in the field.

This embodiment investigates the proliferation inhibitory effect of compounds (IIIb-01~IIIb-65) on tumor cells.

1. On the first day of the cell spreading experiment, 96-well cell culture plates (Corning 3917 plates) were evenly spread with 100 ul per well containing 5000 cells (e.g.: e.g.: pancreatic cancer (BXPC3), lung cancer (A549), renal cancer (Caki-1), liver cancer (Hep3B 2.1-7), gastric cancer (SNU16), cervical cancer cell line (Hela), leukemia cell line (K562), etc.), and then the plates were placed in a cell culture incubator.

2. On the second day of compound spiking experiment, prepare compounds, 10 concentration points of each compound to be tested and positive reference drug, dilute in culture medium with a 1:3 concentration gradient, and replicate the wells. Add 5 ul of compound to be tested or positive reference drug to the cell plate, the final concentration of compound to be tested is up to 10 uM, the final concentration of positive reference drug is up to 3 uM, and the concentration of DMSO is controlled below 0.2%, then place the cell plate in the cell incubator and incubate for 72 hours.

3. On the fifth day, 72 hours after treatment, CTG reagent (Promega G7573) was prepared according to the reagent instructions, and the configured CTG reagent and the cell plates were simultaneously placed at room temperature for 30 minutes for thermal equilibration. Then 50 ul of CTG reagent was added to each well of the cell plate, and the plate was mixed by low-speed shaking and placed at room temperature for 20 minutes and stored away from light. The cell culture plate was then placed on a plate reader (Envision or Viewlux) to record the data and analyze it to calculate the proliferation inhibition rate. The compound concentration corresponding to the 50% inhibition rate in the curve is the $IC_{50}$ for the proliferation inhibition of this compound on the tumor cell line.

Experiments for the Evaluation of Five Kinases Inhibitory Activities ($IC_{50}$)

In this experiment, the inhibitory effects of small molecule inhibitors on 17 kinases were examined by using fluorescent microfluidic mobility shift assay (Mobility-Shift Assay).

1. Buffer configuration: 50 mM HEPES, pH 7.5, 0.00015% Brij-35.

2. Compounds were configured in 100% DMSO in a concentration gradient and diluted with buffer to 10% DMSO, and added to 384-well plates. Compounds starting at 500 nM are prepared in 100% DMSO to 25 µM and diluted in a gradient of 10 concentrations, then diluted 10-fold in buffer to make an intermediate dilution of the compound containing 10% DMSO and transferred 5 µl to a 384-well plate.

3. The kinase was diluted to optimal concentration with the following buffers: 50 mM HEPES, pH 7.5, 0.00015% Brij-35, 2 mM DTT (final concentration of enzyme reaction: VEGFR-1 (FLT1): 2 nM; VEGFR-2 (KDR): 1.2 nM; VEGFR-3 (FLT4): 1.5 nM; FGFR1: 2 nM); FGFR2: 9 nM; FGFR3: 8 nM; FGFR4: 10 nM; PDGFRα: 3.5 nM; c-MET: 10 nM; RET: 7 nM; EGFR: 6 nM). Transfer 10 µl into a 384-well plate and incubate with the compounds for 10 min.
4. The substrate was diluted to the optimum concentration with the following buffer: 50 mM HEPES, pH 7.5, 0.00015% Brij-35. where the final concentration of the reaction was as follows:

VEGFR1 (FLT1): 3 µM Peptide30 (5-FAM-KKKKEE-IYFFF-CONH$_2$), 278 µM ATP, 10 mM MgCl$_2$;

VEGFR2 (KDR): 3 µM Peptide22(5-FAM-EEP-LYWSFPAKKK-CONH$_2$), 92 µM ATP, 10 mM MgCl$_2$;

VEGFR3 (FLT4): 3 µM Peptide30 (5-FAM-KKKKEE-IYFFF-CONH$_2$), 84 µM ATP, 10 mM MgCl$_2$;

FGFR2: 3 µM Peptide22(5-FAM-EEPLYWSFPAKKK-CONH$_2$), 1.9 µM ATP, 10 mM MgCl$_2$;

RET: 3 µM Peptide22(5-FAM-EEPLYWSFPAKKK-CONH$_2$), 23 µM ATP, 10 mM MgCl$_2$ 5. Read the conversion rate with Caliper Reader and calculate the conversion rate as suppression, formula Percent inhIcition=(max−conversion)/(max−min)*100.
6. Calculate the IC$_{50}$ formula Y=Bottom+(Top−Bottom)/(1+(IC$_{50}$/X)^HillSlope) by fitting it with XL-fit 5.4.0.8 software.

The hERG (potassium channel) is an important parameter in the safety of compounds involved in new drug studies. hERG mutations are highly expressed in the heart and are a major component of the rapid repolarization current (IKr) in the third phase of the myocardial action potential. hERG mutations cause a loss of function that is often associated with some inherited long QT syndromes (LQTS) and increase the risk of severe ventricular arrhythmias and torsional tachycardia is increased. The side effects caused by inhibition of potassium (K+) channels are one of the main reasons for the failure and scattering of new drug studies in recent years, and a compound with an in vitro inhibitory effect of hERG with an IC$_{50}$<30 µM may have the above mentioned pitfalls and risks. Therefore, in vitro inhibition of hERG channels (IC$_{50}$) evaluation has been recommended by the International Conference on Harmonization of Drug Registries as part of preclinical safety evaluation (ICHS7B Expert Working Group, '02).

Experimental Evaluation of the In Vitro Inhibitory Effect (IC$_{50}$) of hERG

Stabilized cells were dropped onto circular slides and placed in a culture dish with a cell density below 50% and incubated overnight. Cells for experiments are transferred to a bath of approximately 1 ml embedded in an inverted microscope stage and perfused with extracellular fluid at a rate of 2.7 ml/min. The experiment can be started after 5 minutes of stabilization. Membrane currents were recorded using a HEKA EPC-10 membrane clamp amplifier and a PATCHMASTER acquisition system (HEKA Instruments Inc., D—67466 Lambrecht, Pfalz, Germany). All experiments were performed at room temperature (22~24° C.). A P-97 microelectrode puller (Sutter Instrument Company, One Digital Drive, Novato, Calif. 94949) was used to straighten the electrodes (BF150-110-10) in the experiments. The electrode had an inner diameter of 1-1.5 mm and an inlet resistance of 2-4 MΩ when filled with internal fluid. hERG potassium channels were electrophysiologically stimulated by first clamping the membrane voltage at −80 mV, giving the cells a continuous 2 s, +20 mV voltage stimulation to activate the hERG potassium channels, and then repolarizing to −50 mV for 5 s to generate an outward tail current with a stimulation frequency of every 15 s. Current values are the peak tail currents.

Channel currents were recorded in whole-cell recording mode in the experiments. First, the extracellular fluid (approximately 2 mL per minute) was perfused and recorded continuously, and the current was stabilized (Run-Down less than 5% for 5 minutes), at which point the peak tail current was the control current value. Next, the extracellular fluid containing the drug to be tested was instilled and recorded continuously until the inhibitory effect of the drug on the hERG current reached a steady state, at which point the peak tail current was the post-drug current value. The criterion for steady state was determined by the coincidence of the three most recent consecutive current recording lines. After reaching steady state, if the hERG current returned to or approached the size before the drug was added after washout with extracellular fluid, the test could be continued with other concentrations or drugs. 30 µM Quinidine (Quinidine) was used as a positive control in the experiment to ensure that the cells used responded normally.

Some of the preferred compounds of formula IIIb and others (e.g., IIIb-06, IIIb-08, IIIb-09, IIIb-21, IIIb-45, IIIb-50, IIIb-55, IIIb-56, IIIb-57, IIIb-58, IIIb-60, IIIb-61, IIIb-65) inhibit various tumor cell lines [e.g., pancreatic cancer (BXPC3), lung cancer (A549), renal cancer (Caki-1), liver cancer (Hep3B 2.1-7), gastric cancer (SNU16), cervical cancer (Hela), prostatic cancer (PC-3) and leukemia (K562)] and tyrosine kinase (e.g., VEGFR1, VEGFR2 (KDR), VEGFR3, FGFR2, RET, etc.) activities, the test results are listed in Table 7, Table 8, and Table 9 below.

The range of activity (IC$_{50}$) of each compound to inhibit pancreatic cancer cell line (BXPC3) is labeled as "A" for <5.0 uM, "B" for 5.0-10.0 uM, and "C" for >10.0 uM. as "C".

The range of activity (IC$_{50}$) of each compound to inhibit lung cancer cell line (A549) is labeled "A" for <2.5 uM, "B" for 2.5-5.0 uM, and "C" for >5.0 uM. "C".

The active effect range (IC$_{50}$) of each compound to inhibit kidney cancer cell line (Caki-1) is labeled as "A" for <2.5 uM, "B" for activity range 2.5-5.0 uM, and "C" for activity range >5.0 uM. "C".

The range of activity (IC$_{50}$) of each compound in inhibiting hepatocellular carcinoma cell line (Hep3B 2.1-7) is labeled as "A" for <2.5 uM, "B" for 2.5-5.0 uM, and "C" for >5.0 uM. The range of activity (IC$_{50}$) of each compound in inhibiting gastric cancer cell line (SNU16) is labeled as "A" for <5.0 uM, "B" for 5.0-10.0 uM, and "B" for "B" and activity range >10.0 uM is labeled as "C".

The active effect range (IC$_{50}$) of each compound to inhibit cervical cancer cell lines (Hela) is labeled as "A" for <5.0 uM, "B" for activity range 5.0-10 uM, and "C" for activity range >10 uM. "C".

The active effect range (IC$_{50}$) of each compound to inhibit leukemia cell line (K562) is labeled as "A" for <5.0 uM, "B" for activity range 5.0-10 uM, and "C" for activity range >10 uM. "C".

The active effect range (IC$_{50}$) of each compound to inhibit leukemia cell line (PC-3) is labeled as "A" for <5.0 uM, "B" for activity range 5.0-10 uM, and "C" for activity range >10 uM. "C".

TABLE 7

Results of inhibitory activity assays of three cell lines for some preferred IIIb compounds

| Samples | BXPC3 (pancreatic cancer) | A549 (lung cancer) | Caki-1 (renal cancer) |
|---|---|---|---|
| IIIb-01 | C | C | C |
| IIIb-02 | C | C | C |
| IIIb-03 | C | C | C |
| IIIb-04 | C | C | C |
| IIIb-05 | C | C | C |
| IIIb-06 | C | B | B |
| IIIb-07 | C | C | C |
| IIIb-08 | A | A | A |
| IIIb-09 | A | A | A |
| IIIb-10 | C | C | C |
| IIIb-11 | A | A | A |
| IIIb-12 | C | C | C |
| IIIb-13 | C | C | C |
| IIIb-14 | C | C | C |
| IIIb-15 | C | C | C |
| IIIb-16 |   |   |   |
| IIIb-17 | C | C | C |
| IIIb-18 | C | C | C |
| IIIb-19 | C | C | C |
| IIIb-20 | C | C | C |
| IIIb-21 | B | A | A |
| IIIb-22 | C | B | B |
| IIIb-23 | C | C | C |
| IIIb-24 | C | C | C |
| IIIb-25 | C | C | C |
| IIIb-26 | A | A | A |
| IIIb-27 | C | C | C |
| IIIb-28 | C | C | C |
| IIIb-29 | C | C | C |
| IIIb-30 | C | C | C |
| IIIb-41 | C | C | C |
| IIIb-42 | C | C | C |
| IIIb-45 | A | A | A |
| IIIb-46 | C | C | C |
| IIIb-47 | C | C | C |
| IIIb-48 | C | C | C |
| IIIb-49 | C | C | C |
| IIIb-50 | A | A | A |
| IIIb-51 | C | C | C |
| IIIb-52 | C | C | C |
| IIIb-53 | C | C | C |
| IIIb-54 | C | C | C |
| IIIb-55 | A | A | A |
| IIIb-56 | A | A | A |
| IIIb-57 | A | A | A |
| IIIb-58 | A | A | A |
| IIIb-59 | C | C | C |
| IIIb-60 | A | A | A |
| IIIb-61 | A | A | A |
| IIIb-65 | A | A | A |
| Sorafenib | C | C | C |
| Regorafenib | C | C | C |
| Lenvatinib | C | C | C |

TABLE 8

Results of some preferred IIIb compounds in inhibiting five cell lines of hepatocellular carcinoma, gastric carcinoma, cervical carcinoma, leukemia, and PC-3

| Samples | Hep3B 2.1-7 | SUN16 | Hela | K562 | PC-3 |
|---|---|---|---|---|---|
| IIIb-06 | B | C | A | B | C |
| IIIb-08 | A | A | A | A | B |
| IIIb-09 | A | A | A | A | C |
| IIIb-21 | B | C | C | B | C |
| IIIb-45 | A | A | A | A | B |
| IIIb-50 | A | A | A | A | B |
| IIIb-55 | A | A | A | A | B |
| IIIb-56 | A | A | A | A | B |
| IIIb-57 | A | A | A | A | B |
| IIIb-58 | A | A | A | A | B |
| IIIb-60 | A | A | A | A | B |
| IIIb-61 | A | A | A | A | B |
| IIIb-65 | A | A | A | A | B |
| Sorafenib | C | C | C | C | C |
| Regorafenib | C | B | C | C | C |
| Lenvatinib | C | B | C | B | C |

The results of the activities of some preferred compounds of Formula IIIb for inhibiting RTK targets such as VEGFR1-3, FGFR2, and RET, respectively, are presented in Table 8 below; wherein the activity effect range ($IC_{50}$) of each compound for inhibiting various tyrosine kinases VEGFR1, KDR (VEGFR2), and VEGFR3 at <5 nM is labeled as "A", "B" for the activity range of 5-10 nM, and "C" for the activity range >10 nM; the activity effect range ($IC_{50}$) of each compound to inhibit various tyrosine kinases FGFR2 is labeled as "A" for <50 nM, "B" for 50-100 nM, and "C" for >100 nM; each compound inhibited various tyrosine kinase RET activity effect range ($IC_{50}$) in <5 nM labeled as "A", activity range of 5-10 nM labeled as "B", activity range >10 nM labeled as "C".

TABLE 9

Results of inhibition of five tyrosine kinase activities for some preferred IIIb compounds

| Samples | VEGFR1 | KDR | VEGFR3 | FGFR2 | RET |
|---|---|---|---|---|---|
| IIIb-08 | A | A | A | A | A |
| IIIb-09 | B | A | A | B | B |
| IIIb-21 | A | A | A | B | B |
| IIIb-45 | A | A | A | A | A |
| IIIb-50 | A | A | A | A | A |
| IIIb-55 | A | A | A | A | B |
| IIIb-56 | A | A | A | A | A |
| IIIb-57 | A | A | A | A | A |
| IIIb-58 | A | A | A | A | A |
| IIIb-60 | A | A | A | A | A |
| IIIb-61 | A | A | A | A | A |
| IIIb-65 | A | A | A | A | A |
| Sorafenib | C | C | C | C | C |
| Regorafenib | C | C | C | B | C |
| Lenvatinib | B | B | A | B | B |

TABLE 10

Results of hERG inhibition effect assay for t some preferred IIIb compounds

|   | Compound | hERG ($IC_{50}$, uM) |
|---|---|---|
| 1 | IIIb-06 | 18.7 |
| 2 | IIIb-08 | >30 |
| 3 | IIIb-09 | >30 |
| 4 | IIIb-45 | >30 |
| 5 | IIIb-50 | >30 |
| 6 | IIIb-55 | >30 |
| 7 | IIIb-56 | >30 |
| 8 | IIIb-57 | >30 |
| 9 | IIIb-58 | >30 |
| 10 | IIIb-60 | >30 |

TABLE 10-continued

Results of hERG inhibition effect assay
for t some preferred IIIb compounds

| | Compound | hERG (IC$_{50}$, uM) |
|---|---|---|
| 11 | IIIb-61 | >30 |
| 12 | IIIb-65 | >30 |
| 13 | Sorafenib | >10 |
| 14 | Regorafenib | 27 |
| 15 | Lenvatinib | 11.9 |

From the results of various tests in Tables 7, 8, 9 and 10 above, it can be found that the compounds listed in the above tables "IIIb-08, IIIb-09, IIIb-45, IIIb-50, IIIb-55, IIIb-56, IIIb-57, IIIb-58, IIIb-60, IIIb-61, IIIb-65" of the present invention have better inhibitory effects on various tumor cell lines and tyrosine kinases than those already on the market, and their inhibitory activities and safety parameters such as hERG>30 uM are significantly better than those of the three urea referenced drugs, namely lenvatinib, regorafenib and sorafenib, which have been marketed clinically.

Example 70: Compound Toxicity Screening Test

In order to test the toxicity of the new compounds "IIIb-08, IIIb-09, IIIb-45, IIIb-50, IIIb-55, IIIb-56, IIIb-57, IIIb-58, IIIb-60, IIIb-61, IIIb-65", which are the more active and preferred compounds in Tables 7-9 above, the MTD toxicity test (150 mg/kg, QD) was conducted in rats, and no abnormalities such as death occurred during 14 consecutive days of administration. The autopsy results of the rats did not reveal any abnormal changes in the heart, liver, lungs, kidneys, stomach, intestines and other organs in the body, and the compounds tested were generally considered safe and non-toxic within the appropriate doses.

These preferred compounds (e.g., IIIb-08, IIIb-09, IIIb-45, IIIb-50, IIIb-55, IIIb-56, IIIb-57, IIIb-58, IIIb-60, IIIb-61, IIIb-65) are currently being used to inhibit tumor suppression in nude mice subcutaneously transplanted with pancreatic cancer cell line (BXPC3), gastric cancer cell line (SNU16), liver cancer cell line (Hep3B 2.1-7) and other tumor suppressive effects have been observed in vivo, the tumor suppression rate of subcutaneous tumors in nude mice could reach 80-110% within 3-4 weeks. The results show that these preferred compounds have better efficacy in antitumor activity. Therefore, the preferred compounds "IIIb-08, IIIb-09, IIIb-45, IIIb-50, IIIb-55, IIIb-56, IIIb-57, IIIb-58, IIIb-60, IIIb-61, IIIb-65" designed and synthesized by the present invention not only have better inhibitory activity, but also have better safety and drug-forming properties, which are valuable for further preclinical studies such as pharmacotoxicology and clinical trials.

In summary, the compounds "IIIb-08, IIIb-09, IIIb-45, IIIb-50, IIIb-55, IIIb-56, IIIb-57, IIIb-58, IIIb-60, IIIb-61, IIIb-65" found in the multi-targeted antitumor innovative drug study not only have better inhibitory activity, but also have better safety in the MTD toxicity test in rats (150 mg/kg, QD), with no abnormalities such as death during 14 consecutive days of dosing. The safety profile is better (better than the reference drug "lenvatinib" with a publicly reported MTD of 40 mg/kg), and the results regarding inhibitory activity and safety are better than those of similar control drugs such as lenvatinib, which are currently known.

In general, the terms used in the claims should not be considered as limiting the claims to the specific embodiments disclosed in this specification and claims, but rather as including all possible embodiments and other chemically reasonable variations that follow the full scope of the listed claims equivalent. Accordingly, the claims are not limited by this disclosure.

What is claimed is:

1. A compound represented by formula IIIb, or a stereoisomer, tautomer, deuterate, pharmacologically acceptable salt, or hydrate thereof:

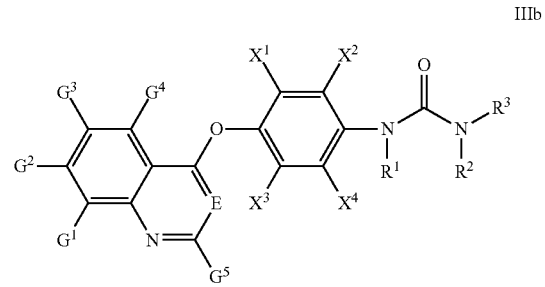

IIIb wherein:
E is a nitrogen (N) or CH;
$G^1$ is independently selected from H, deuterium (D), halogen, cyano, $C_{1-20}$ alkyl, $C_{1-20}$ alkoxy, or $C_{1-20}$ alkylamino group;
$G^2$ is independently selected from halogen, cyano, $C_{1-20}$ alkylamino, $C_{2-20}$ hydroxyalkylideneamino, $C_{3-20}$ hydroxycycloalalkylideneamino, $C_{1-20}$ cyanoalkylideneamino, $C_{4-20}$ cyanocycloalalkylideneamino, $C_{1-20}$ aminoalkylideneamino, $C_{3-20}$ aminocycloalkylideneamino, $C_{1-20}$ carboxyalkylideneamino, $C_{4-20}$ carboxycycloalalkylideneamino, 3-6 members heterocyclic-amino group, or —OR$^6$, wherein R$^6$ is independently selected from H, deuterium (D), $C_{1-20}$ alkyl, $C_{1-20}$ haloalkyl, $C_{1-20}$ cyanoalkyl, $C_{4-20}$ cyanocycloalalkylidene, $C_{2-20}$ hydroxyalkylidene, $C_{3-20}$ hydroxycycloalkylidene, $C_{1-20}$ aminoalkylidene, $C_{3-20}$ aminocycloalkylidene, $C_{2-20}$ carboxyalkylidene, $C_{4-20}$ carboxycycloalalkylidene, $C_{3-6}$ cycloalkylidene, $C_{3-6}$ aminocycloalkylidene, $C_{1-20}$ amino($C_{3-20}$cycloalkyl)alkylidene, 3-6 members heterocycloalkyl, or 3-6 members heterocycloalkylidene group.
$G^3$ is independently selected from cyano, —C(O)OR, —C(O)NH$_2$, —C(O)ND$_2$, $C_{1-20}$ alkoxy, $C_{1-20}$ alkylamino, or a —C(O)NR$^4$R$^5$ group: wherein R is H, or $C_{1-20}$ alkyl, R$^4$ and R$^5$ are each independently selected from H, deuterium (D), $C_{1-20}$ alkyl, $C_{1-20}$ haloalkyl, $C_{1-20}$ cyanoalkylidene, $C_{4-20}$ cyanocycloalalkylidene, $C_{2-20}$ hydroxyalkylidene, $C_{3-20}$ hydroxycycloalkylidene, $C_{2-20}$ aminoalkylidene, $C_{3-20}$ aminocycloalkylidene, $C_{2-20}$ carboxyalkylidene, $C_{4-20}$ carboxycycloalalkylidene, $C_{3-20}$ cycloalkenyl, $C_{3-20}$ cycloalkyl, 3-6 members heterocyclic, 3-6 members heterocyclic alkylidene, $C_{6-20}$ aryl, $C_{3-20}$ heterocyclic aryl, $C_{1-20}$ alkyl sulfonyl, $C_{3-20}$ cycloalkyl sulfonyl, or $C_{2-20}$ heterocycloalkyl sulfonyl group; or R$^4$ and R$^5$ may be linked each other to form a $C_{2-20}$ heterocyclic group or a $C_{3-20}$ heterocyclic aryl group containing 3-8 members of 1-3 heteroatoms; or may be linked each other to form $C_9$-$C_{20}$ fused alkylaryl or $C_8$-$C_{20}$ aryl group, G⁴ and G⁵ are each independently selected from H, deuterium (D), halogen, cyano, $C_{1-20}$ alkyl, $C_{1-20}$ alkoxy, or $C_{1-20}$ alkylamino goup;

$R^1$ is each independently selected from H, deuterium (D), $C_{1-20}$ alkyl, $C_{3-20}$ cycloalkyl, or $C_{3-20}$ deuterated cycloalkyl group;

$R^2$ and $R^3$ are each independently selected from H, deuterium (D), $C_{1-20}$ alkyl, $C_{3-20}$ cycloalkyl, $C_{3-20}$ deuterated cycloalkyl, or a 3-6 membered heterocyclic group;

$X^1$, $X^2$ and $X^3$ are each independently selected from halogen, cyano, amino, $C_{1-20}$ alkoxy, or $C_{1-20}$ alkyl amino group;

$X^4$ is each independently selected from H, deuterium (D), halogen, cyano, amino, $C_{1-20}$ alkoxy, or $C_{1-20}$ alkylamino group.

2. The compound according to claim 1, wherein E is a nitrogen (N) or CH;

$G^1$ is independently selected from H, deuterium (D), halogen, cyano, $C_{1-12}$ alkyl, $C_{1-12}$ alkoxy, or $C_{1-}$ alkylamino group;

$G^2$ is independently selected from halogen, cyano, $C_{1-12}$ alkylamino, $C_{2-12}$ hydroxyalkylideneamino, $C_{3-12}$ hydroxycycloalkylideneamino, $C_{1-12}$ cyanoalkylideneamino, $C_{4-12}$ cyanocycloalkylideneamino, $C_{1-12}$ aminoalkylideneamino, $C_{3-12}$ aminocycloalkylideneamino, $C_{1-12}$ carboxyalkylideneamino, $C_{4-12}$ carboxycycloalkylideneamino, 3-6 members heterocyclic-amino group, or —OR⁶, wherein R⁶ is independently selected from H, deuterium (D), $C_{1-12}$ alkyl, $C_{1-12}$ haloalkyl, $C_{1-12}$ cyanoalkyl, $C_{4-12}$ cyanocycloalkylidene, $C_{2-12}$ hydroxyalkylidene, $C_{3-12}$ hydroxycycloalkylidene, $C_{1-12}$ aminoalkylidene, $C_{3-12}$ aminocycloalkylidene, $C_{2-12}$ carboxyalkylidene, $C_{4-12}$ carboxycycloalkylidene, $C_{3-6}$ cycloalkylidene, $C_{3-6}$ aminocycloalkylidene, $C_{1-12}$ amino($C_{3-12}$cycloalkyl)alkylidene, 3-6 members heterocycloalkyl, or 3-6 members heterocycloalkylidene group;

$G^3$ is independently selected from cyano, —C(O)OR, —C(O)NH₂, —C(O)ND₂, $C_{1-12}$ alkoxy, $C_{1-12}$ alkylamino, or a —C(O)NR⁴R⁵ group: wherein R is H, or $C_{1-12}$ alkyl, $R^4$ and $R^5$ are each independently selected from H, deuterium (D), $C_{1-12}$ alkyl, $C_{1-12}$ haloalkyl, $C_{1-12}$ cyanoalkylidene, $C_{4-12}$ cyanocycloalkylidene, $C_{2-12}$ hydroxyalkylidene, $C_{3-12}$ hydroxycycloalkylidene, $C_{2-12}$ aminoalkylidene, $C_{3-12}$ aminocycloalkylidene, $C_{2-12}$ carboxyalkylidene, $C_{4-12}$ carboxycycloalkylidene, $C_{3-12}$ cycloalkenyl, $C_{3-12}$ cycloalkyl, 3-6 members heterocyclic, 3-6 members heterocyclic alkylidene, $C_{6-12}$ aryl, $C_{3-12}$ heterocyclic aryl, $C_{1-12}$ alkyl sulfonyl, $C_{3-12}$ cycloalkyl sulfonyl, or $C_{2-12}$ heterocycloalkyl sulfonyl group; or $R^4$ and $R^5$ may be linked to each other to form a $C_{2-12}$ heterocyclic group or a $C_{3-12}$ heterocyclic aryl group containing 3-8 members of 1-3 heteroatoms; or may be linked to each other to form $C_9$-$C_{20}$ fused alkylaryl or $C_8$-$C_{20}$ aryl group, $G^4$ and $G^5$ are each independently selected from H, deuterium (D), halogen, cyano, $C_{1-12}$ alkyl, $C_{1-12}$ alkoxy, or $C_{1-12}$ alkylamino group;

$R^1$ is each independently selected from H, deuterium (D), $C_{1-12}$ alkyl, $C_{3-12}$ cycloalkyl, or $C_{3-12}$ deuterated cycloalkyl group;

$R^2$ and $R^3$ are each independently selected from H, deuterium (D), $C_{1-12}$ alkyl, $C_{3-12}$ cycloalkyl, $C_{3-12}$ deuterated cycloalkyl, or a 3-6 membered heterocyclic group;

$X^1$, $X^2$ and $X^3$ are each independently selected from halogen, cyano, amino, $C_{1-12}$ alkoxy, or $C_{1-12}$ alkyl amino group;

$X^4$ is each independently selected from H, deuterium (D), halogen, cyano, amino, $C_{1-12}$ alkoxy, or $C_{1-12}$ alkylamino group.

3. The compound according to claim 2, wherein

E is a nitrogen (N) or CH;

$G^1$ is independently selected from H, deuterium (D), halogen, cyano, $C_{1-6}$ alkyl, $C_{1-6}$ alkoxy, or $C_{1-6}$ alkylamino group;

$G^2$ is independently selected from halogen, cyano, $C_{1-6}$ alkylamino, $C_{2-6}$ hydroxyalkylideneamino, $C_{3-6}$ hydroxycycloalkylideneamino, $C_{1-6}$ cyanoalkylideneamino, $C_{4-6}$ cyanocycloalkylideneamino, $C_{1-6}$ aminoalkylideneamino, $C_{3-6}$ aminocycloalkylideneamino, $C_{1-6}$ carboxyalkylideneamino, $C_{4-6}$ carboxycycloalkylideneamino, 3-6 members heterocyclic-amino group, or —OR⁶, wherein R⁶ is independently selected from H, deuterium (D), $C_{1-6}$ alkyl, $C_{1-6}$ haloalkyl, $C_{1-6}$ cyanoalkyl, $C_{4-6}$ cyanocycloalkylidene, $C_{2-6}$ hydroxyalkylidene, $C_{3-6}$ hydroxycycloalkylidene, $C_{1-6}$ aminoalkylidene, $C_{3-6}$ aminocycloalkylidene, $C_{2-6}$ carboxyalkylidene, $C_{4-6}$ carboxycycloalkylidene, $C_{3-6}$ cycloalkylidene, $C_{3-6}$ aminocycloalkylidene, $C_{1-6}$ amino($C_{3-6}$ cycloalkyl)alkylidene, 3-6 members heterocycloalkyl, or 3-6 members heterocycloalkylidene group;

$G^3$ is independently selected from cyano, —C(O)OR, —C(O)NH₂, —C(O)ND₂, $C_{1-≠}$alkoxy, $C_{1-6}$ alkylamino, or a —C(O)NR⁴R⁵ group: wherein R is H, or $C_{1-6}$ alkyl, $R^4$ and $R^5$ are each independently selected from H, deuterium (D), $C_{1-6}$ alkyl, $C_{1-6}$ haloalkyl, $C_{1-6}$ cyanoalkylidene, $C_{4-6}$ cyanocycloalkylidene $C_{2-6}$ hydroxyalkylidene, $C_{3-6}$ hydroxycycloalkylidene, $C_{2-6}$ aminoalkylidene, $C_{3-6}$ aminocycloalkylidene, $C_{2-6}$ carboxyalkylidene, $C_{4-6}$ carboxycycloalkylidene, $C_{3-6}$ cycloalkenyl, $C_{3-6}$ cycloalkyl, 3-6 members heterocyclic, 3-6 members heterocyclic alkylidene, $C_{6-10}$ aryl, $C_{3-6}$ heterocyclic aryl, $C_{1-6}$ alkyl sulfonyl, $C_{3-6}$ cycloalkyl sulfonyl, or $C_{2-6}$ heterocycloalkyl sulfonyl group; or $R^4$ and $R^5$ may be linked to each other to form a $C_{2-6}$ heterocyclic group or a $C_{3-6}$ heterocyclic aryl group containing 3-8 members of 1-3 heteroatoms; or may be linked to each other to form $C_9$-$C_{20}$ fused alkylaryl or $C_8$-$C_{20}$ aryl group, $G^4$ and $G^5$ are each independently selected from H, deuterium (D), halogen, cyano, $C_{1-6}$ alkyl, $C_{1-6}$ alkoxy, or $C_{1-6}$ alkylamino group;

$R^1$ is each independently selected from H, deuterium (D), $C_{1-6}$ alkyl, $C_{3-6}$ cycloalkyl, or $C_{3-6}$ deuterated cycloalkyl group;

$R^2$ and $R^3$ are each independently selected from H, deuterium (D), $C_{1-6}$ alkyl, $C_{3-6}$ cycloalkyl, $C_{3-6}$ deuterated cycloalkyl, or a 3-6 membered heterocyclic group;

$X^1$, $X^2$ and $X^3$ are each independently selected from halogen, cyano, amino, $C_{1-6}$ alkoxy, or $C_{1-6}$ alkyl amino group;

$X^4$ is each independently selected from H, deuterium (D), halogen, cyano, amino, $C_{1-6}$ alkoxy, or $C_{1-6}$ alkylamino group.

4. The compound according to claim 3, wherein

E is CH;

$G^1$ is H;

$G^2$ is —OR6, wherein $R^6$ is independently selected from H, deuterium (D), $C_{1-6}$ alkyl, $C_{1-6}$ haloalkyl, $C_{1-6}$ cyanoalkylidene, $C_{4-6}$ cyanocycloalkylidene, $C_{2-6}$ hydroxyalkylidene, $C_{3-6}$ hydroxycycloalkylidene, $C_{2-6}$ aminoalkylidene, $C_{3-6}$ aminocycloalkylidene, $C_{2-6}$ carboxyalkylidene, $C_{4-6}$ carboxycycloalkylidene, $C_{3-6}$ cycloalkyl, $C_{3-6}$ aminocycloalkylidene, $C_{1-6}$ amino($C_{3-6}$cycloalkyl)alkylidene, 3-6 members heterocycloalkyl, or 3-6 members heterocycloalkylidene group;

$G^3$ is independently selected from C(O)OR, C(O)NH$_2$, or a C(O)NR$^4$R$^5$ group, wherein, R is H, or $C_{1-6}$ alkyl, R$^4$ and R$^5$ are each independently selected from H, $C_{1-6}$ alkyl, $C_{1-6}$ haloalkyl, $C_{1-6}$ cyanoalkylidene, $C_{4-6}$ cyanoalkylidene, $C_{2-6}$ hydroxyalkylidene, $C_{2-6}$ aminoalkylidene, $C_{3-6}$ cycloalkyl, 3-6 members heterocyclic, 3-6 members heterocyclic alkylidene, $C_{3-6}$ heterocyclic aryl, $C_{1-6}$ alkyl sulfonyl, $C_{3-6}$ cycloalkyl sulfonyl, or $C_{2-6}$ heterocycloalkyl sulfonyl group; or R$^4$ and R$^5$ are interconnected into a heterocyclic group or a heterocyclic aryl, of 3-8 members containing 1-3 heteroatoms;

$G^4$ and $G^5$ are each independently selected from H;

$R^1$ is H;

$R^2$ and $R^3$ are each independently selected from H, or $C_{3-6}$ cycloalkyl group;

$X^1$, $X^2$ and $X^3$ are each independently selected from halogen;

$X^4$ is H.

5. The compound according to claim 4, which is represented by one of the following structures:

IIIb-08

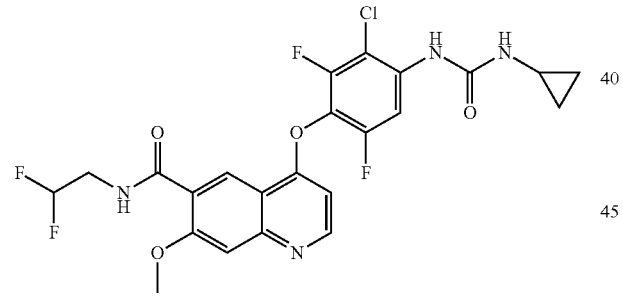

IIIb-09

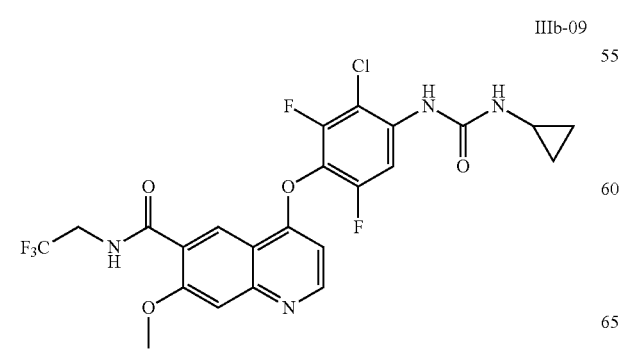

-continued

IIIb-45

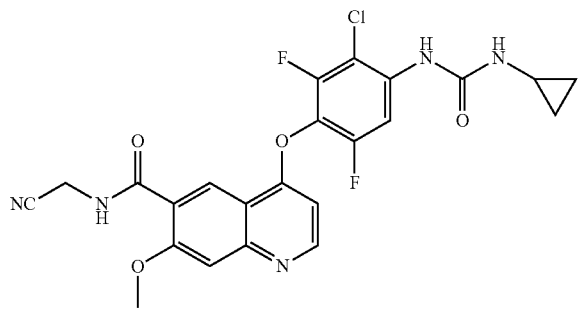 [SMILES: COc1cc2nccc(Oc3c(F)cc(NC(=O)NC4CC4)c(Cl)c3F)c2cc1C(=O)NCC(F)(F)F]

IIIb-50

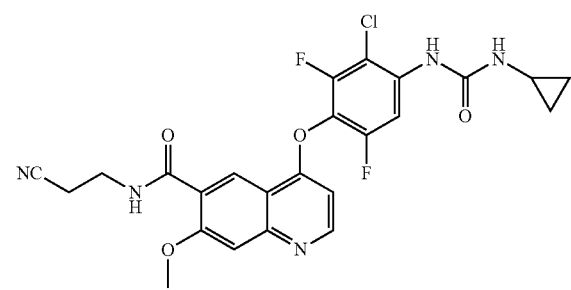 [SMILES: COc1cc2nccc(Oc3c(F)cc(NC(=O)NC4CC4)c(Cl)c3F)c2cc1C(=O)NCC(O)C(F)(F)F]

IIIb-55

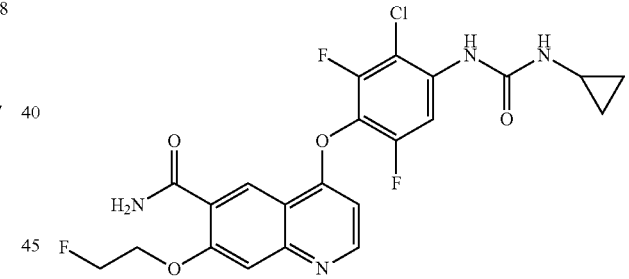

IIIb-56

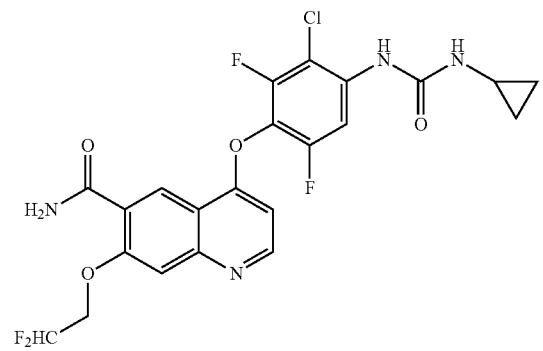

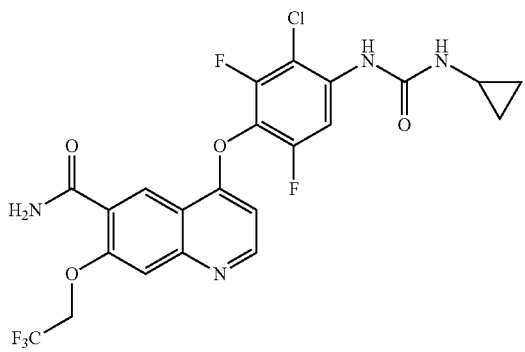 [SMILES: NC(=O)c1cc2c(Oc3c(F)cc(NC(=O)NC4CC4)c(Cl)c3F)ccnc2cc1OCC(F)(F)F]

IIIb-57

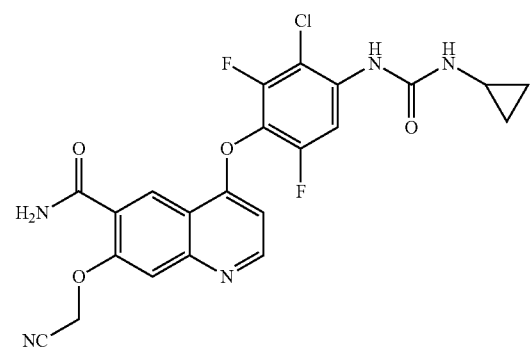 [SMILES: N#CCOc1cc2nccc(Oc3c(F)cc(NC(=O)NC4CC4)c(Cl)c3F)c2cc1C(N)=O]

IIIb-58

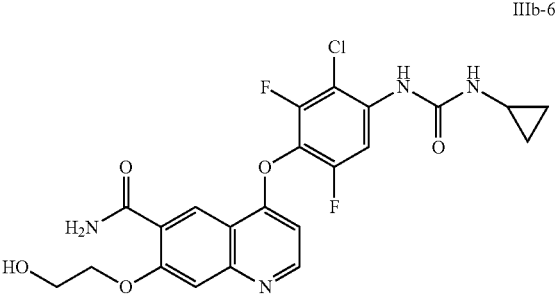

IIIb-60

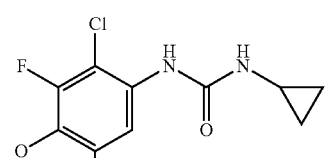

IIIb-61

IIIb-65

6. A pharmaceutical composition comprising the compound according to claim 1 and a pharmaceutically acceptable carrier.

7. A composition comprising at least one compound according to claim 1 and at least one tyrosine kinase (RTK) inhibitor.

8. A method of treating cancer, comprising administering an effective amount of the compound according to claim 1 to a subject in need thereof, wherein the treated cancer is selected from the group consisting of pancreatic cancer, lung cancer, renal cancer, liver cancer, gastric cancer, cervical cancer, and leukemia.

* * * * *